US012758261B2

(12) United States Patent
Fischer et al.

(10) Patent No.: US 12,758,261 B2
(45) Date of Patent: Oct. 13, 2026

(54) VENTING SURGICAL CANNULA FOR PROVIDING GASES TO A PATIENT

(71) Applicant: FISHER & PAYKEL HEALTHCARE LIMITED, Auckland (NZ)

(72) Inventors: Christian Francis Fischer, Auckland (NZ); Richard John Boyes, Auckland (NZ); Abigail Sharmini Rajen Arulandu, Auckland (NZ); Benjamin Elliot Hardinge Pegman, Auckland (NZ); Zane Paul Gell, Auckland (NZ); Katie-Ann Jane Buckels, Auckland (NZ); Zach Jonathan Warner, Auckland (NZ); Charlotte Grace Laus, Auckland (NZ); Vincent Verdoold, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 585 days.

(21) Appl. No.: 17/268,904

(22) PCT Filed: Aug. 16, 2019

(86) PCT No.: PCT/NZ2019/050099
§ 371 (c)(1),
(2) Date: Feb. 16, 2021

(87) PCT Pub. No.: WO2020/036497
PCT Pub. Date: Feb. 20, 2020

(65) Prior Publication Data

US 2021/0267639 A1 Sep. 2, 2021

Related U.S. Application Data

(60) Provisional application No. 62/719,572, filed on Aug. 17, 2018.

(51) Int. Cl.
*A61B 17/34* (2006.01)
*A61M 13/00* (2006.01)
*A61M 25/00* (2006.01)

(52) U.S. Cl.
CPC ....... *A61B 17/3474* (2013.01); *A61M 13/003* (2013.01); *A61B 2218/008* (2013.01);
(Continued)

(58) Field of Classification Search
CPC .......... A61B 17/3474; A61B 2218/008; A61B 17/3421; A61M 13/003; A61M 25/0032;
(Continued)

(56) References Cited

U.S. PATENT DOCUMENTS 6,592,543 B1 * 7/2003 Wortrich ................ A61B 18/00 604/35
8,128,590 B2 * 3/2012 Albrecht ............ A61B 17/3474 604/23
(Continued)

FOREIGN PATENT DOCUMENTS

CN 102264309 A 11/2011
CN 105962997 A 9/2016
(Continued)

OTHER PUBLICATIONS

International Search Report for International Patent Application No. PCT/NZ2019/050099, dated Nov. 28, 2019 in 11 pages.
(Continued)

*Primary Examiner* — Kami A Bosworth
*Assistant Examiner* — Avery Smale
(74) *Attorney, Agent, or Firm* — Knobbe, Martens, Olson & Bear, LLP

(57) ABSTRACT

A surgical cannula for providing insufflation gases to a surgical cavity of a patient (such as the pneumoperitoneum), allowing insertion of medical instruments into the surgical
(Continued)

cavity through the surgical cannula, and venting gases from the surgical cavity to an outside environment can include venting features including filters to more safely reduce an amount of undesirable materials such as smoke from reaching the outside environment.

20 Claims, 43 Drawing Sheets

(52) U.S. Cl.
CPC . *A61M 25/0032* (2013.01); *A61M 2025/0039* (2013.01); *A61M 2205/75* (2013.01)

(58) Field of Classification Search
CPC ...... A61M 2025/0039; A61M 2205/75; A61M 39/02; A61M 2039/0205; A61M 39/0247; A61M 2039/0264; A61M 2039/027; A61M 2039/0276; A61M 2039/0279; A61M 13/00; A61M 13/006
See application file for complete search history.

(56) References Cited

U.S. PATENT DOCUMENTS

| | | | | |
|---|---|---|---|---|
| 8,551,049 | B2 | 10/2013 | Ott et al. | |
| 8,551,050 | B2 | 10/2013 | Ott et al. | |
| 8,585,646 | B2 | 11/2013 | Lloyd et al. | |
| 9,295,490 | B2 | 3/2016 | Stearns et al. | |
| 2002/0128603 | A1* | 9/2002 | Booth | A61B 17/3421 604/164.01 |
| 2004/0167478 | A1 | 8/2004 | Mooney et al. | |
| 2010/0185057 | A1 | 7/2010 | Stearns et al. | |
| 2011/0125084 | A1 | 5/2011 | Stearns et al. | |
| 2012/0165610 | A1 | 6/2012 | Poll et al. | |
| 2013/0233318 | A1 | 9/2013 | Graham et al. | |
| 2016/0158468 | A1 | 6/2016 | Tang et al. | |
| 2016/0228671 | A1 | 8/2016 | Jackson et al. | |
| 2017/0007295 | A1* | 1/2017 | Geisz | A61B 17/3421 |
| 2017/0028159 | A1 | 2/2017 | Ghalib et al. | |
| 2017/0319268 | A1 | 11/2017 | Akagane | |
| 2018/0228510 | A1* | 8/2018 | Holsten | B01D 46/0097 |

FOREIGN PATENT DOCUMENTS

| | | | | |
|---|---|---|---|---|
| CN | 106456929 A | | 2/2017 | |
| CN | 106943657 A | | 7/2017 | |
| EP | 2 279 704 A1 | | 2/2011 | |
| FR | 2705555 A1 | * | 12/1994 | A61M 13/003 |
| JP | 2005245772 A | * | 9/2005 | |
| WO | WO 2016/140039 A1 | | 9/2016 | |
| WO | WO 2017/122188 A9 | | 7/2017 | |

OTHER PUBLICATIONS

Written Opinion for International Patent Application No. PCT/NZ2019/050099, dated Nov. 28, 2019 in 9 pages.

* cited by examiner

VENTING SURGICAL CANNULA FOR PROVIDING GASES TO A PATIENT

INCORPORATION BY REFERENCE TO ANY PRIORITY APPLICATIONS

The present application is a 371 of International Patent Application No. PCT/NZ2019/050099, filed on Aug. 16, 2019, which claims priority benefit of U.S. Provisional Application Ser. No. 62/719,572, filed on Aug. 17, 2018, the disclosures of each of which are hereby incorporated by reference in their entireties.

FIELD OF THE DISCLOSURE

The present disclosure relates in some aspects to humidifier systems and components of humidifier systems configured to supply gases to a patient, in particular during a medical procedure.

BACKGROUND

Various medical procedures require the provision of gases, typically carbon dioxide, to a patient during the medical procedure. For example, two general categories of medical procedures often require providing gases to a patient. These include closed type medical procedures and open type medical procedures.

In closed type medical procedures, an insufflator is arranged to deliver gases to a body cavity of the patient to inflate the body cavity and/or to resist collapse of the body cavity during the medical procedure. Examples of such medical procedures include laparoscopy and endoscopy, although an insufflator may be used with any other type of medical procedure as required. Endoscopic procedures enable a medical practitioner to visualize a body cavity by inserting an endoscope or the like through one or more natural openings, small puncture(s), or incision(s) to generate an image of the body cavity. In laparoscopy procedures, a medical practitioner typically inserts a surgical instrument through one or more natural openings, small puncture(s), or incision(s) to perform a surgical procedure in the body cavity. In some cases an initial endoscopic procedure may be carried out to assess the body cavity, and then a subsequent laparoscopy carried out to operate on the body cavity. Such procedures are widely used, for example, on the peritoneal cavity, or during a thoracoscopy, colonoscopy, gastroscopy or bronchoscopy.

In open type medical procedures, for example, open surgeries, gases are used to fill a surgical cavity, with excess gases spilling outward from the opening. The gases can also be used to provide a layer of gases over exposed internal body parts where there is no discernible cavity. For these procedures, rather than serving to inflate a cavity, the gases can be used to prevent or reduce desiccation and infection by covering exposed internal body parts with a layer of heated, humidified, sterile gases.

An apparatus for delivering gases during these medical procedures can include an insufflator arranged to be connected to a remote source of pressurized gases, for example, a gases supply system in a hospital. The apparatus can be operative to control the pressure and/or flow of the gases from the gases source to a level suitable for delivery into the body cavity, usually via a cannula or needle connected to the apparatus and inserted into the body cavity, or via a diffuser arranged to diffuse gases over and into the wound or surgical cavity.

The internal body temperature of a human patient is typically around 37° C. It can be desirable to match the temperature of the gases delivered from the apparatus as closely as possible to the typical human body temperature. It can also be desirable to deliver gases above or below internal body temperature, such as, for example, 1° C., 2° C., 3° C., 4° C., 5° C., 6° C., 7° C., 8° C., 9° C., 10° C., or 15° C. above or below internal body temperature for example, or ranges including any two of the foregoing values. It can also be desirable to deliver gases at a desired fixed or variable humidity and/or a desired fixed or variable gas temperature. The gases at the desired gas temperature and/or humidity (which may be also referred to herein as standard) can be dry cold gas, dry hot gas, humidified cold gas, or humidified hot gas for example. Further, the gases delivered into the patient's body can be relatively dry, which can cause damage to the body cavity, including cell death or adhesions. In many cases, a humidifier is operatively coupled to the insufflator. A controller of the apparatus can energize a heater of the humidifier located in the gases flow path to deliver humidification fluid (e.g., water) vapor to the gases stream prior to entering the patient's body cavity.

The humidified gas can be delivered to the patient via further tubing which may also be heated. The insufflator and humidifier can be located in separate housings that are connected together via suitable tubing and/or electrical connections, or located in a common housing arranged to be connected to a remote gas supply via suitable tubing.

SUMMARY

During laparoscopic surgery, there will generally be some form of electrosurgery, electrocautery, laser cutting or cauterising, or other types of energy to cause cutting or coagulation within the surgical cavity, e.g., the pneumoperitoneum for certain abdominal surgeries. This produces surgical smoke which can increase in concentration over time in the sealed and pressurised surgical cavity, e.g., peritoneum, especially when there are no significant gas leaks or suction/irrigation. The smoke plume rises and can block vision. Further the smoke plume may contact or deposit particles on the scope. The smoke plume contacting the scope can also cause fogging or condensation on the scope. In other words, a high concentration of smoke in the pneumoperitoneum, and in the field of vision can severely impede the optical clarity when viewing the space inside the peritoneum through a lens inserted through a trocar. The trocar can include a cannula and obturator. Without the use of venting or suction, surgeons generally have no option but to release an amount of the gas from inside the pneumoperitoneum through deflation, then re-insufflation, which can be inconvenient and cause undesirably increased operating room and anesthesia time. Therefore, it can be useful to vent out smoke plumes and smoke concentration, which can prevent or at least reduce condensation and/or fogging. Condensation can occur on various surfaces on a medical instrument. When condensation forms on a viewing surface of a medical instrument, this is observed as a fogging effect which manifests as an impairment of visibility through a lens or any other viewing surface of a medical instrument (such as, for example, a mirror or transparent or translucent window). When condensation forms on various surfaces of a medical instrument, the condensation can coalesce into water droplets. This can occur directly on the viewing surface or other surfaces which can then migrate to or be deposited on the viewing surface. Accordingly, as used herein condensation and/or fogging means condensation generally and in some instances, specifically with respect to condensation on a viewing surface (i.e. fogging).

In some configurations, systems and methods as disclosed herein can advantageously vent gas (and smoke plumes created during electrosurgery, electrocautery, laser cutting or cauterising, or other types of energy) from inside the pneumoperitoneum which achieves at least two advantages: it can dilute the smoke concentration inside the pneumoperitoneum to improve visibility, and it can also ensure a constant flow of $CO_2$ form the insufflator which creates an airflow of "clean" $CO_2$ gas across/over the viewing area which carries or pushes away smoke that is hindering vision in the area between the lens and operating area. The venting flow rate may be related to the delivered flow rate. In one example the venting rate (i.e. venting flow rate) may be set to achieve a specified pressure within the surgical site. Explained another way, the venting rate is such that a surgical cavity is maintained at a predetermined pressure rate. In some embodiments, venting flow rate may be a predetermined flow rate. For example, the flow rate may be set by the user. The venting element used may be constructed or tuned to achieve the predetermined flow rate. However, there can be a trade-off when venting in terms of negatively affecting stability and pressure of the pneumoperitoneum.

In some configurations, systems and methods can advantageously filter to remove harmful chemicals & bio-particles from the gas being vented into the operation room. A growing concern in surgical environments is hazards to surgical staff (and patients) from the smoke produced during electrosurgery, electrocautery, laser cutting or cauterising, or other types of energy. Research indicates that surgical smoke can contribute to cancers or other health issues, and contains many chemicals and bio-particles that can be hazardous for human inhalation. Therefore, it can be advantageous in some cases to include an integrated smoke filter, or capacity to have the filter as a removable attachment on the venting outlet. Standards to govern the filtering of surgical smoke in operating theatres are still being created and implemented around the world; the strictest of these standards specifies filtering of particles down to ~0.1-0.2 microns, at 99.999% efficiency. In some embodiments, a filter could include a ULPA filter which filters down to 0.12 microns or less at 99.9995% or greater efficiency can be used, potentially in addition to a carbon filter stage to remove odors. Both the filter and removal of smoke can be combined in a number of different ways.

The present disclosure provides examples of a cannula with one, two, or more lumens configured for venting of gases, including smoke from a surgical cavity that can remedy the aforementioned problems and/or other problems. The cannula can be single use (disposable) or reusable. Alternatively, parts of the cannula can be single use (disposable) or reusable. The cannula may be made of materials that are biocompatible and/or sterilizable. In the present disclosure, features of the different examples of venting cannulas can be incorporated into or combined with one another.

In some aspects, disclosed herein is a surgical cannula for providing insufflation gases to a surgical cavity and venting gases from the surgical cavity, the cannula including a cannula upper housing, and an elongate shaft extending from the cannula upper housing. The cannula upper housing and elongate shaft comprise a first lumen comprising an inlet and an outlet. The cannula upper housing and elongate shaft comprise a first lumen comprising a first lumen inlet and a first lumen outlet. The first lumen is configured to receive insufflation gases from an inlet in the cannula upper housing and deliver the insufflation gases from an outlet proximate a distal end of the elongate shaft and into the surgical cavity. The first lumen inlet is in fluid communication with a source of the insufflation gases. The cannula upper housing and elongate shaft comprise a second lumen comprising an inlet and an outlet. The cannula upper housing and elongate shaft comprise a second lumen comprising a second lumen inlet and a second lumen outlet. The second lumen can be configured to receive gases through the second lumen inlet from the surgical cavity and vent the gases through the second lumen outlet outside the surgical cavity. The second lumen is in fluid communication with a venting element operably connected to the surgical cannula.

In some configurations the first lumen and second lumen is at least partially nested, or fully with respect to each other; or concentric with respect to each other.

In some configurations the first lumen is radially offset with respect to the second lumen or the second lumen is radially offset with respect to the first lumen.

In some configurations the second lumen includes a diameter that is greater than, less than, or equal to a diameter of the first lumen.

In some configurations the venting element is configured to provide passive venting created by a pressure differential with respect to the surgical cavity.

In some configurations the inlet of the first lumen is configured to connect with an outlet of a gases source. In some configurations the first lumen inlet is configured to connect with a gases source outlet.

In some configurations the first lumen or the second lumen includes one or more positioning ribs configured to locate and/or retain the other of the first lumen or the second lumen, such as at least 2, 3, or more positioning ribs.

In some configurations the positioning ribs are integrally formed with an inner wall of the first lumen or the second lumen.

In some configurations the first lumen comprises a cross-sectional area that is larger than, smaller than, or equal to a cross-sectional area of the second lumen.

In some configurations the second lumen comprises one of a semi-circular, crescent, or arcuate profile.

In some configurations the first lumen comprises a circular profile.

In some configurations the second lumen comprises a helical shape at least partially circumscribing the first lumen.

In some configurations the first lumen is configured to house a medical instrument therethrough.

In some configurations a cannula further comprises a third lumen configured to house a medical instrument therethrough.

In some configurations a cannula also includes one or more filters in fluid communication with the second lumen.

In some configurations the filter is contained within the venting element removably coupled to the cannula upper housing.

In some configurations the venting element is removably coupled to the cannula upper housing via a clip.

In some configurations the filter is integrally formed with the cannula upper housing and/or second lumen.

In some configurations the filter is positioned within the cannula upper housing.

In some configurations the filter is operably connected to a conduit connected to the proximal end of the cannula upper housing.

In some configurations the outlet of the second lumen is angled with respect to a longitudinal axis of the cannula upper housing. In some configurations the second lumen outlet is angled with respect to a longitudinal axis of the cannula upper housing.

In some configurations the outlet angle of the second lumen is about 45 degrees. In some configurations the angle of the second lumen outlet is about 45 degrees.

In some configurations the cannula also includes a seal configured to seal against a medical instrument, the seal located in the cannula upper housing and aligned with respect to at least one of the first lumen and the second lumen.

In some configurations the seal is a duck-billed seal or a flap seal.

In some configurations, disclosed herein is a surgical cannula for providing insufflation gases to a surgical cavity and venting gases from the surgical cavity, the cannula comprising: a cannula upper housing; and an elongate shaft extending from the cannula upper housing. The cannula upper housing and elongate shaft comprise a lumen configured to receive insufflation gases from an inlet in the cannula upper housing and deliver the insufflation gases proximate a distal end of the elongate shaft and into the surgical cavity. A lumen inlet is in fluid communication with a source of the insufflation gases. The lumen is also configured to receive gases from the surgical cavity and vent the gases from the surgical cavity outside the surgical cavity. The cannula also includes a venting element in fluid communication with the lumen. The venting element further includes a filter configured to filter the gases from the surgical cavity before the gases from the surgical cavity are vented out of the surgical cannula.

In some configurations the venting element is integrated into the cannula upper housing, and/or the lumen.

In some configurations the lumen includes a wall extending partially axially along the lumen, the wall configured to divide the lumen into a first passage configured to deliver insufflation gases to the surgical cavity and a second passage configured to vent gases from the surgical cavity.

In some configurations the first passage is concentric with the second passage; offset from the second passage; and/or fluidly isolated from the second passage.

In some configurations the venting element is removably attached to the cannula upper housing.

In some configurations the venting element further comprises a first locking mechanism configured to lock the venting element to a second complementary locking mechanism on the cannula upper housing.

In some configurations the first locking mechanism creates a seal between the venting element and the cannula upper housing when the first locking mechanism is locked to the second locking mechanism.

In some configurations the venting element also includes at least one venting aperture, the filter positioned adjacent the venting aperture and configured such that gases from the surgical cavity pass through the filter and out the at least one venting aperture.

In some configurations the cannula also includes a plurality of venting apertures, and the venting of gases from the surgical cavity occurs passively due to a pressure differential between the surgical cavity and ambient air.

In some configurations the venting element also includes a venting valve, e.g., a solenoid valve.

In some configurations the venting element also includes one or more sensors, the one or more sensors configured to sense at least one of temperature, pressure, and humidity.

In some configurations the venting element also includes an integrated heating element configured to heat a portion of the filter and prevent condensation with the filter.

In some configurations the venting element also includes a fin extending into the cannula upper housing and positioned adjacent a gas inlet port to guide flow of insufflation gases from the gas inlet port.

In some configurations also disclosed herein is a surgical cannula for providing insufflation gases to a surgical cavity and venting gases from the surgical cavity, the cannula comprising a cannula upper housing; an elongate shaft extending from the cannula upper housing; and a first filter and a second filter in fluid communication with the second lumen, the second filter spaced distally apart from the first filter. The cannula upper housing and elongate shaft can comprise a first lumen comprising an inlet and an outlet. The cannula upper housing and elongate shaft can include a first lumen comprising a first lumen inlet and a first lumen outlet. The first lumen can be configured to receive insufflation gases from an inlet in the cannula upper housing and deliver the insufflation gases from an outlet proximate a distal end of the elongate shaft and into the surgical cavity. The first lumen inlet is in fluid communication with a source of the insufflation gases. The cannula upper housing and elongate shaft can comprise a second lumen comprising an inlet and an outlet. The cannula upper housing and elongate shaft can include a second lumen comprising a second lumen inlet and a second lumen outlet. The second lumen can be configured to receive gases through the second lumen inlet from the surgical cavity and vent the gases through the second lumen outlet outside the surgical cavity. The second lumen is in fluid communication with a venting element operably connected to the surgical cannula. The first filter is contained within the venting element removably coupled to the cannula upper housing.

In some configurations the second filter is positioned distal to the first filter, and comprise a sidewall gases venting exit port.

In some configurations the second filter is also be positioned within the cannula upper housing.

In some configurations disclosed herein is a cannula for providing insufflation gases to a surgical cavity and venting gases from the surgical cavity. The cannula can include a cannula upper housing; and an elongate shaft extending from the cannula upper housing. The cannula upper housing and elongate shaft comprise a first lumen comprising an inlet and an outlet, the first lumen configured to receive insufflation gases from an inlet in the cannula upper housing and deliver the insufflation gases from an outlet proximate a distal end of the elongate shaft and into the surgical cavity. The first lumen inlet is in fluid communication with a source of the insufflation gases. The cannula upper housing and elongate shaft comprise a second lumen comprising an inlet and an outlet, the second lumen configured to receive gases through the second lumen inlet from the surgical cavity and vent the gases through the second lumen outlet. The second lumen is in fluid communication with a venting element operably connected to the surgical cannula. The cannula further comprises a blower unit in fluid communication with the second lumen, the blower unit comprising a fan and a blower drive unit, the blower unit configured to suction the gases from the surgical cavity into the second lumen. The cannula can further comprise or be connected to one or more suction units configured to suction the gases from the surgical cavity into the second lumen. The cannula can further comprise or be connected to a humidifier or a heater configured to humidify or heat the gases being delivered to the first lumen.

In some configurations the blower drive unit comprises a magnetic circular ring.

In some configurations also disclosed herein is a multi-cannula surgical cannula system for providing insufflation gases to a surgical cavity and recirculating filtered insufflation gases back into the surgical cavity. The cannula system includes a first cannula comprising a first lumen configured to house a first medical instrument therethrough and a second lumen, a blower unit in fluid communication with the second lumen, and at least one filter in fluid communication with the second lumen, the blower unit comprising a fan and a blower drive unit, the blower unit configured to suction the gases from the surgical cavity into the second lumen, the second lumen configured to receive the suctioned gases from the surgical cavity; and a second cannula comprising a first lumen configured to house a second medical instrument therethrough and a second lumen, the second lumen of the second cannula configured to be in fluid communication with the second lumen of the first cannula via a conduit, the second lumen of the second cannula configured to recirculate the filtered insufflation gases back into the surgical cavity.

In some configurations at least one of the first cannula and the second cannula further comprises insufflation gas inlets connectable to a source of insufflation gases.

In some configurations also disclosed herein is a surgical cannula system for providing insufflation gases to a surgical cavity and recirculating filtered insufflation gases back into the surgical cavity. The cannula system includes a cannula comprising a first lumen configured to house a first medical instrument therethrough and a second lumen, a blower unit in fluid communication with the second lumen, and at least one filter in fluid communication with the second lumen, the blower unit comprising a fan and a blower drive unit, the blower unit configured to suction the gases from the surgical cavity into the second lumen, the second lumen configured to receive the suctioned gases from the surgical cavity. The cannula further comprises a third lumen in communication with the second lumen of the first cannula via at the at least one filter, the third lumen configured to recirculate the filtered insufflation gases back into the surgical cavity. The cannula can further include insufflation gas inlets connectable to a source of insufflation gases.

In some configurations also disclosed herein is a surgical cannula for providing insufflation gases to a surgical cavity and venting gases from the surgical cavity. The cannula includes a cannula upper housing; and an elongate shaft extending from the cannula upper housing. The cannula upper housing and elongate shaft comprises a first lumen comprising an inlet and an outlet. The cannula upper housing and elongate shaft can comprise a first lumen comprising a first lumen inlet and a first lumen outlet. The first lumen can be configured to receive insufflation gases from an inlet in the cannula upper housing and deliver the insufflation gases from an outlet proximate a distal end of the elongate shaft and into the surgical cavity. The first lumen inlet is in fluid communication with a source of the insufflation gases. The cannula upper housing and elongate shaft comprises a second lumen comprising an inlet and an outlet. The cannula upper housing and elongate shaft can include a second lumen comprising a second lumen inlet and a second lumen outlet. The second lumen can be configured to receive gases through the second lumen inlet from the surgical cavity and vent the gases through the second lumen outlet. The second lumen is in fluid communication with a venting element operably connected to the surgical cannula. The cannula further comprises a control operably connected to a seal proximate the second lumen outlet. The control has an inactivated state and an activated state, and the control in an activated state causes the seal to open, allowing venting of the gases through the second lumen outlet.

In some configurations the control could include a button.

In some configurations also disclosed herein is a surgical cannula for providing insufflation gases to a surgical cavity and venting gases from the surgical cavity. The cannula includes a cannula upper housing; and an elongate shaft extending from the cannula upper housing. The cannula upper housing and elongate shaft comprises a first lumen comprising an inlet and an outlet. The cannula upper housing and elongate shaft can include a first lumen comprising a first lumen inlet and a first lumen outlet. The first lumen can be configured to receive insufflation gases from an inlet in the cannula upper housing and deliver the insufflation gases from an outlet proximate a distal end of the elongate shaft and into the surgical cavity. The first lumen inlet is configured to be in fluid communication via a first conduit with a first source of the insufflation gases and via a second conduit to a second source of the insufflation gases. The cannula upper housing and elongate shaft comprises a second lumen comprising an inlet and an outlet. The cannula upper housing and elongate shaft comprise a second lumen comprising a second lumen inlet and a second lumen outlet. The second lumen can be configured to receive gases through the second lumen inlet from the surgical cavity and vent the gases through the second lumen outlet. The second lumen is in fluid communication with a venting element operably connected to the surgical cannula. The second source of insufflation gases is a high-pressure insufflation gases source configured to be sufficient to create a pressure differential sufficient to cause smoke from the surgical cavity to be suctioned into the second lumen via a Venturi effect.

In some configurations, the cannula includes one or more heating elements disposed within the cannula.

In some configurations the heating elements are positioned within and extend some distance along the lumen that delivers gases and/or the venting pathway.

In some configurations the heating element may be disposed in the shaft and may also be in thermal communication with the venting element. The heating element is used to prevent condensation and/or fogging in the venting cannula.

In some configurations further disclosed herein is a surgical cannula for providing insufflation gases to a surgical cavity and venting gases from the surgical cavity. The cannula includes a cannula upper housing; and an elongate shaft extending from the cannula upper housing. The cannula upper housing and elongate shaft comprises a first lumen comprising an inlet and an outlet. The cannula upper housing and elongate shaft can include a first lumen comprising a first lumen inlet and a first lumen outlet. The first lumen can be configured to receive insufflation gases from an inlet in the cannula upper housing and deliver the insufflation gases from an outlet proximate a distal end of the elongate shaft and into the surgical cavity, and the first lumen inlet is in fluid communication with a source of the insufflation gases. The cannula upper housing and elongate shaft comprises a second lumen comprising an inlet and a plurality of outlets. The cannula upper housing and elongate shaft comprise a second lumen comprising a second lumen inlet and a plurality of second lumen outlets. The second lumen can be configured to receive gases through the second lumen inlet from the surgical cavity and vent the gases through the second lumen outlet. The second lumen can be configured to receive gases through the second lumen inlet from the surgical cavity and vent the gases through the plurality of second lumen outlets The second lumen is in fluid communication with a venting element operably connected to the surgical cannula. The cannula upper housing is configured to be connected to a rotatable proximal cap comprising threads and a plurality of circumferentially-oriented slots, the slots configured to block or at least partially allow venting from the plurality of outlets of the second lumen upon rotation of the rotatable cap to control a venting rate of the gases. The cannula upper housing is configured to be connected to a rotatable proximal cap comprising threads and a plurality of circumferentially-oriented slots, the slots configured to block or at least partially allow venting from the plurality of second lumen outlets upon rotation of the rotatable cap to control a venting rate of the gases.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure. In some cases, a "slice" has been shown for clarity purposes for some sectional and cross-sectional views of a three dimensional cannula. A person reasonably skilled in the art would be able to appreciate that these figures illustrate a slice of a three dimensional cannula. In some cases, the projection surfaces have not been shown for clarity. For example, projecting hole surfaces have not been shown in some views.

FIG. 25C is a cross-sectional view through line 25C-25C of FIG. 25A.

DETAILED DESCRIPTION

Although certain embodiments and examples are described below, those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described below.

Example Medical Gases Delivery Systems

Gases can be introduced to a surgical cavity, such as the peritoneal cavity via a cannula inserted through an incision made in patient's body for example (such as the abdominal wall for example). The cannula can be coupled to an insufflator. The gases flow from the insufflator can be increased to inflate the surgical cavity (such as to maintain a pneumoperitoneum, which is a cavity filled with gas within the abdomen, for example). The introduced gases can inflate the surgical cavity. A medical instrument can be inserted through the cannula into the inflated surgical cavity. The medical instrument may be a surgical instrument. For example, an endoscope can be inserted into the cavity and visibility in the cavity can be assisted by insertion of fluids, including gases, such as air or carbon dioxide for example, or liquids. After initial insufflation and insertion of the instrument (such as a laparoscope for example) through the primary cannula, additional cannulas can be placed in the surgical cavity under laparoscopic observation. At the end of the operating procedure, all instruments and cannulas are removed from the surgical cavity, the gases or liquids are expelled, and each incision is closed. For thoracoscopy, colonoscopy, sigmoidoscopy, gastroscopy, bronchoscopy, and/or others, the same or substantially similar procedure for introducing gases to a surgical cavity can be followed. The quantity and flow of gases or liquids can be controlled by the clinician performing the examination and/or automatically by the surgical system. The surgical system may be an insufflation system. The insufflator may deliver intermittent or continuous flow. The insufflator can control flow to ensure that the pressure in the surgical cavity is maintained at or around a predetermined range. The pressure allows for the pneumo cavity to be inflated to a predetermined amount.

Figure 1:
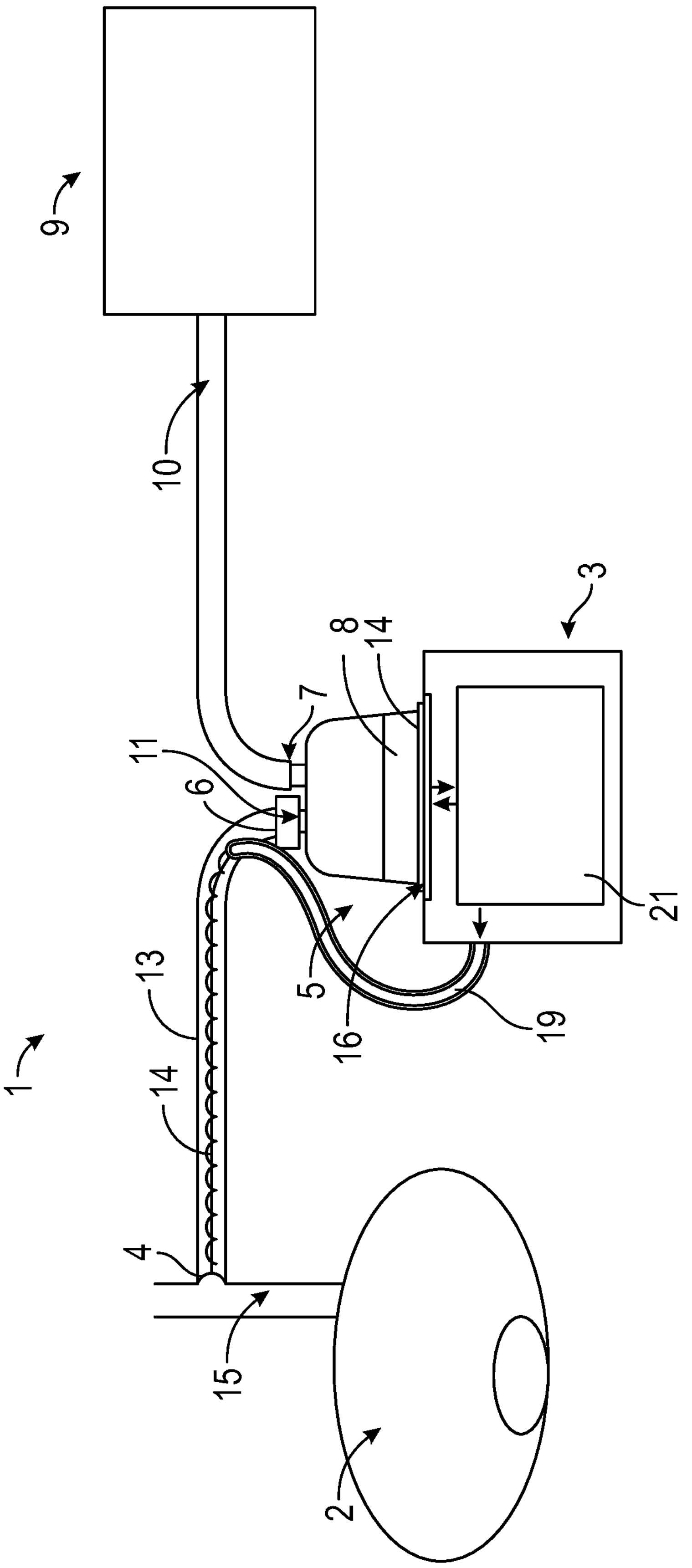
FIG. 1 illustrates schematically an example medical gases delivery apparatus in use in surgery.
Figure 2:
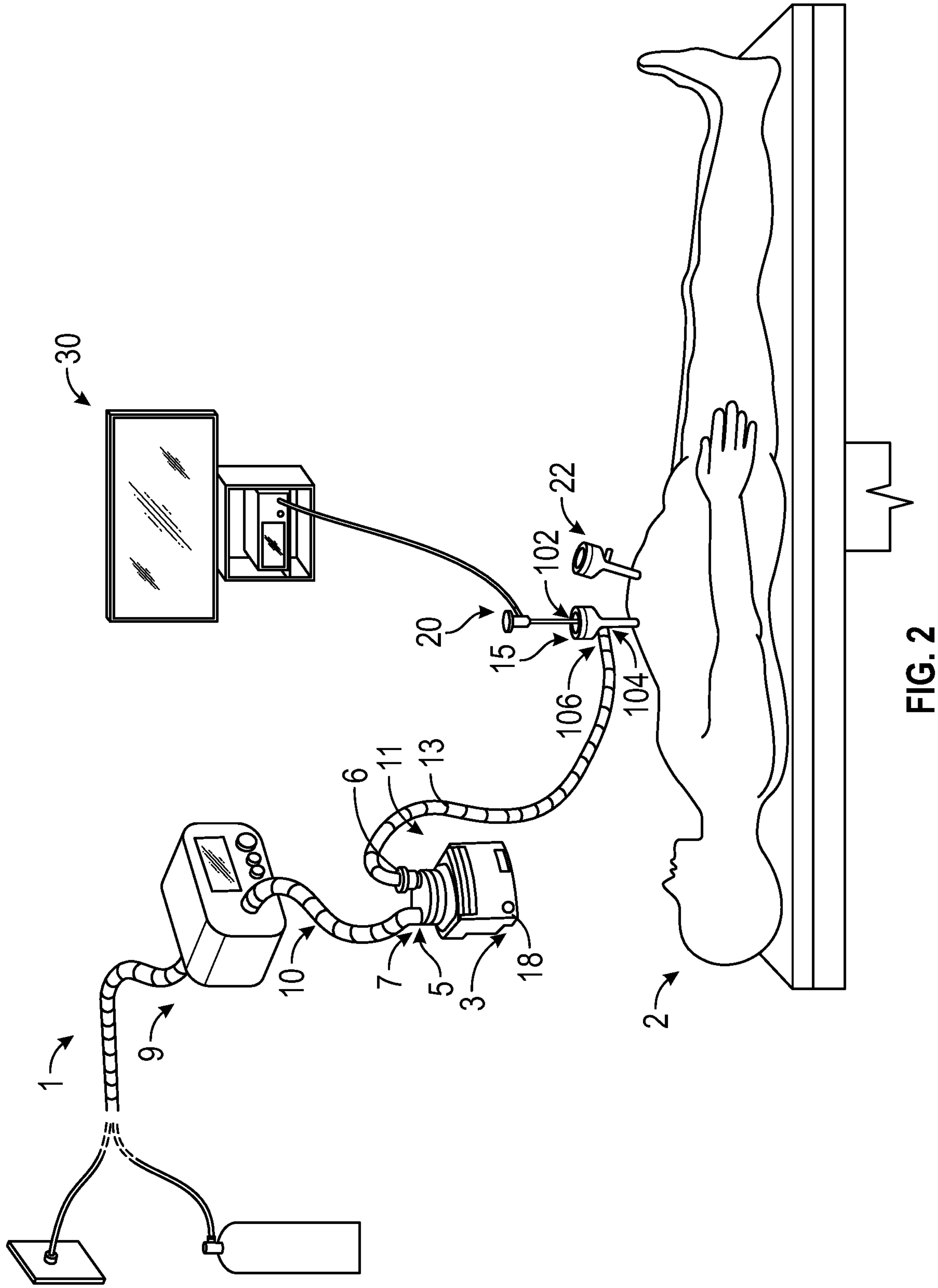
FIG. 2 illustrates schematically an example medical gases delivery apparatus in use in surgery.

FIGS. 1 and 2 illustrate schematically using an example surgical system 1 during a medical procedure. Features of FIGS. 1 and 2 can be incorporated into each other. The same features have the same reference numerals in FIGS. 1 and 2. As shown in FIG. 1, the patient 2 can have a cannula 15 inserted within a cavity of the patient 2 (for example, an abdomen of the patient 2 in the case of a laparoscopic surgery), as previously described.

As shown in FIGS. 1 and 2, the cannula 15 can be connected to a gases delivery conduit 13 (for example, via a Luer lock connector 4). The cannula 15 can be used to deliver gases into a surgical site, such as within the cavity of the patient 2 for example. The cannula 15 can include one or more passages to introduce gases and/or one or more surgical instruments 20 into the surgical cavity. The surgical instrument can be a scope, electrocautery tool, or any other instrument. The surgical instrument 20 can be coupled to an imaging device 30, which can have a screen. The imaging device 30 can be part of a surgical system, which can include a plurality of surgical tools and/or apparatuses. The surgical system may be a surgical stack.

The system can also optionally include a venting cannula 22, which can have substantially the same features as the cannula 15. The venting cannula may include a valve that allows venting. The valve can be automatically controlled by a controller associated with the gases source (i.e. insufflator) or by a controller in the humidifier. A controller may be associated with both the gases source (e.g., insufflator) and the humidifier. The controller associated with the gases source and/or the humidifier may be external from the gases source and/or the humidifier. The controller may also be positioned internally within the cannula. The valve can also be manually actuated (for example, by turning a tap by hand or by a foot pedal, or otherwise). The venting cannula 22 can be coupled to a filtration system to filter out smoke and the like. The venting cannula 22 can also alternatively be coupled to a recirculation system that is configured to recirculate the gases from the surgical cavity back to the insufflator for re-delivery into the surgical cavity. The gases can be filtered and/or dehumidified prior to being returned to the insufflator.

The gases delivery conduit 13 can be made of a flexible plastic and can be connected to a humidifier chamber 5. The humidifier chamber 5 can optionally or preferably be in serial connection to a gases supply 9 via a further conduit 10. The gases supply or gases source can be an insufflator, bottled gases, or a wall gases source. The gases supply 9 can provide the gases without humidification and/or heating. A filter 6 can be connected downstream of the humidifier's outlet 11. The filter 6 can also be located along the further conduit 10, or at an inlet of the cannula 15. The filter 6 can be configured to filter out pathogens and particulate matter in order to reduce infection or contamination of the surgical site from the humidifier or gases source. The gases supply can provide a continuous or intermittent flow of gases. The further conduit 10 can also preferably be made of flexible plastic tubing.

The gases supply 9 can provide one or more insufflation gases, such as carbon dioxide for example, to the humidifier chamber 5. The gases can be humidified as they are passed through the humidifier chamber 5, which can contain a volume of humidification fluid 8, such as water for example. The gases can also be humidified in a humidifier chamber 5 that is heated or non-heated.

A humidifier that incorporates the humidifier chamber 5 can be any type of humidifier. The humidifier chamber 5 can include plastic formed chamber having a metal or otherwise conductive base 14 sealed thereto. The base can be in contact with the heater plate 16 during use. The volume of humidification fluid 8 (for example, water) contained in the chamber 5 can be heated by a heater plate 16, which can be under the control of a controller or control means 21 of the humidifier. The volume of humidification fluid 8 within the chamber 5 can be heated such that it evaporates, mixing humidification fluid vapor with the gases flowing through the chamber 5 to heat and humidify the gases.

The controller or control means 21 can be housed in a humidifier base unit 3, which can also house the heater plate 16. The heater plate 16 can have an electric heating element therein or in thermal contact therewith. One or more insulation layers can be located between in the heater plate 16 and the heater element. The heater element can be a base element (or a former) with a wire wound around the base element. The wire can be a nichrome wire (or a nickel-chrome wire). The heater element can also include a multi-layer substrate with heating tracks electrodeposited thereon or etched therein. The controller or control means 21 can include electronic circuitry, which can include a microprocessor for controlling the supply of energy to the heating element. The humidifier base unit 3 and/or the heater plate 16 can be removably engageable with the humidifier chamber 5. The humidifier chamber 5 can also alternatively or additionally include an integral heater.

The heater plate 16 can include a temperature sensor, such as a temperature transducer for example or otherwise, which can be in electrical connection with the controller 21. The heater plate temperature sensor can be located within the humidifier base unit 3. The controller 21 can monitor the temperature of the heater plate 16, which can approximate a temperature of the humidification fluid 8. The humidification fluid may be water.

A temperature sensor can also be located at the or near the outlet 11 to monitor a temperature of the humidified gases leaving the humidifier chamber 5 from the outlet 11. The temperature sensor can also be connected to the controller 21 (for example, with a cable or wirelessly). Additional sensors can also optionally be incorporated, for example, for sensing characteristics of the gases (such as temperature, humidity, flow, for example, or others) at a patient end of the gases delivery conduit 13.

The gases can exit out through the humidifier's outlet 11 and into the gases delivery conduit 13. The gases can move through the gases delivery conduit 13 into the surgical cavity of the patient 2 via the cannula 15, thereby inflating and maintaining the pressure within the cavity. Preferably, the gases leaving the outlet 11 of the humidifier chamber 5 can have a relative humidity of up to 100%, for example the relative humidity can be 100%. As the gases travel along the gases delivery conduit 13, further condensation and/or fogging can occur so that humidification fluid vapor can condense on a wall of the gases delivery conduit 13. The humidification fluid may be water. Further condensation and/or fogging can have undesirable effects, such as detrimentally reducing the fluid content of the gases delivered to the patient for example. In order to reduce and/or minimize the occurrence of condensation and/or fogging within the gases delivery conduit 13, a heater wire 14 can be provided within, throughout, or around the gases delivery conduit 13. The heater wire 14 can be electronically connected to the humidifier base unit 3, for example by an electrical cable 19 to power the heater wire. In some embodiments, other heating elements could be included in addition or alternatively, e.g., a conductive ink, or a flexible PCB. Optionally, the heating element can include an inductive heating element. Optionally, the heating element can include a chemical heating element, for example, but not limited to silica beads. Optionally, the cannula can be pre-heated prior to insertion.

The heater wire 14 can include an insulated copper alloy resistance wire, other types of resistance wire, or other heater element, and/or be made of any other appropriate material. The heater wire can be a straight wire or a helically wound element. An electrical circuit including the heater wire 14 can be located within walls of the gases delivery tube 13. The gases delivery tube 13 can be a spiral wound tube. Alternatively, the gases delivery tube 13 can include a non-helical or straight tube. Optionally, the gases delivery tube 13 can be corrugated or non-corrugated. The heater wire 14 can be spirally wound around an insulating core of the gases delivery conduit 13. The insulating coating around the heater wire 14 can include a thermoplastics material which, when heated to a predetermined temperature, can enter a state in which its shape can be altered and the new shape can be substantially elastically retained upon cooling. The heater wire 14 can be wound in a single or double helix. Measurements by the temperature sensor and/or the additional sensor(s) at the patient end of the conduit 13 can provide feedback to the controller 21 so that the controller 21 can optionally energize the heater wire to increases and/or maintain the temperature of the gases within the gases delivery conduit 13 (for example, between approximately 35° C. and 45° C.) so that the gases delivered to the patient at the desired temperature, which can be at or close to 37° C. or above or below the internal body temperature (for example, approximately 5, 10, or 15 degrees above or below 37° C.). Alternatively or additionally the system can include additional sensors configured to measure one or more parameters, e.g., ambient temperature and ambient humidity sensors; and/or flow sensors, and/or pressure sensors configured to determine flow rate or pressure of flow or determine the pressure within a cavity or in the tube. Additionally or alternatively the system may also include additional sensors. The sensors can be located upstream, downstream, and/or within the humidifier. The sensors may be configured to determine a parameter of the insufflation gases or one or more parameters of the patient/surgical cavity. Each of the sensors can provide feedback information to one or more controllers which in turn can provide closed loop feedback to keep humidity, temperature, flow, pressure, or other parameters within desired parameters, e.g., a preset range.

The controller or control means 21 can, for example, include the microprocessor or logic circuit with associated memory or storage means, which can hold a software program. When executed by the control means 21, the software can control the operation of the surgical system 1 in accordance with instructions set in the software and/or in response to external inputs. The surgical system may be an insufflation system. For example, the controller or control means 21 can be provided with input from the heater plate 16 so that the controller or control means 21 can be provided with information on the temperature and/or power usage of the heater plate 16. The controller or control means 21 can be provided with inputs of temperature of the gases flow. For example, the temperature sensor can provide input to indicate the temperature of the humidified gases flow as the gases leave the outlet 11 of the humidifier chamber 5. A flow sensor can also be provided in the same position as or near the temperature sensor or at other appropriate location within the surgical system 1. The controller 21 can control a flow controller which regulates the flow rate of gases through the system 1. The flow controller may be a flow regulator. The controller can include a flow inducer and/or inhibiter such as a motorized fan for example. Valves and/or vents can additionally or alternatively be used to control the gases flow rate.

A patient input 18 located on the humidifier base unit 3 can allow a user (such as a surgeon or nurse for example) to set a desired gases temperature and/or gases humidity level to be delivered. Other functions can also optionally be controlled by the user input 18, such as control of the heating delivered by the heater wire 14 for example. The controller 21 can control the system 1, and in particular to control the flow rate, temperature, and/or humidity of gas delivered to the patient, to be appropriate for the type of medical procedure for which the system 1 is being used.

The humidifier base unit 3 can also include a display for displaying to the user the characteristics of the gas flow being delivered to the patient 2.

Although not shown, the humidifier can also optionally be a passover or bypass humidifier, which can include the chamber with a volume of water or any other type of humidification fluid, but may not include a heater plate for heating the humidification fluid. The chamber can be in fluid communication with the gases supply such that the insufflation gases are humidified by humidification fluid vapor wicked from the volume of humidification fluid as the insufflation gases pass over the volume of humidification fluid.

When in use, the humidifiers described above can be located outside an "operating sterile zone" and/or adjacent the insufflator. As a result, the medical personnel would not be required to touch the humidifier when moving the cannula during the operation to maneuver the medical instruments within the surgical cavity. The humidifier may not need to be sterilized to the same extent as the medical instruments. Furthermore, the humidifier being located outside the "operating sterile zone" can reduce obstructions to the medical personnel during the operating procedure that may restrict movements of the medical personnel and/or the medical instruments in the already crowded space.

Examples of Venting Cannulas

During laparoscopic surgery, there will generally be some form of electrosurgery, electrocautery, laser cutting or cauterising, or other types of energy to cause cutting or coagulation within the insufflated cavity. This produces surgical smoke which can increase in concentration over time in the sealed and pressurised peritoneum or other cavity, especially when there are no significant gas leaks or suction/irrigation. During these operations/procedures there is often also a smoke plume that is generated. The smoke plume can engulf the scope or move across the scope and restrict vision of the surgeon. Clearing the smoke as well as clearing the smoke plumes help in improving optical clarity during surgery. This makes surgery safer, faster and more efficient. A high concentration of smoke in the insufflated cavity, and in the field of vision can severely impede the optical clarity when viewing the space inside the peritoneum through a lens inserted through a trocar. The lens can be connected to a camera positioned, for example, outside of the surgical cavity. Without the use of venting or suction, surgeons generally have no option but to release all the gas from inside the pneumoperitoneum through deflation, then re-insufflation.

The present disclosure provide examples of a cannula, which can be used as the cannula 15 disclosed herein, and which includes venting and filtering features to increase the optical clarity of a surgical cavity without requiring additional components or tools, or a time-intensive deflation and re-insufflation procedure as noted above. The example venting cannulas disclosed herein can be implemented into existing surgical systems without requiring customized and/or more expensive surgical systems. The surgical systems may be insufflation systems. The example venting cannulas disclosed herein can therefore improve optical clarity of the lens and/or maintain a clear field of vision, which can aid in minimizing operation time and post-operation complications including but not limited to pain, and/or can make it easier for the medical personnel, such as the surgeon for example, in navigating the scope during the medical procedure. Cannulas 22 such as described above can be utilized as or modified for use as a venting cannula. In some embodiments, a cannula with venting passages and gas delivery passages can be advantageous because it provides a single device that can be used to deliver gases and vent out smoke and other gases from the pneumo, thereby helping to maintain a clear field of vision.

In some embodiments, a surgical cannula includes a housing, an elongate shaft extending from the housing, and at least one lumen within the elongate shaft. The cannula can include gripping features to grip against the surgical cavity. The housing can include one or more seals/valves disposed adjacent an instrument opening. The seals/valves are configured to seal against an instrument inserted through the instrument opening. A gases inlet is disposed on the housing or the shaft. The gases inlet can be in fluid communication with the lumen and receives gases from either a humidifier or an insufflator. The surgical cannula may include other features such as external seals for example and may include either a flat (e.g., square) tip or an angled (e.g., beveled) tip. Any number of venting features as disclosed elsewhere herein can be incorporated into cannulas as described.

In some embodiments, the example venting cannulas can have any of the features of the cannula 15. For example, the venting cannula can have a cannula upper housing 102 connected to an elongate shaft 104. The elongate shaft 104 can optionally have a pointed end such that the cannula can function as a trocar for easier insertion of the cannula 100 into the surgical cavity. The cannula upper housing 102 can have a greater cross-sectional dimension than the elongate shaft 104 for easier insertion of the medical instruments. As shown in FIG. 2, the cannula upper housing 102 can have generally a funnel shape, with a cross-sectional dimension (for example, diameter) decreasing from a location further from the elongate shaft 104 to a location closer to the elongate shaft 104. A gases inlet 106 can be located on the cannula upper housing 102. The cannula upper housing 102 can include a cavity. The elongate shaft 104 can include a hollow passage. The cavity and the hollow passage can be in fluid communication. The venting cannula can include a heating element releasably coupled to (for example, via a sleeve) or integrated into the venting cannula (for example, in at least a portion of the cannula upper housing 102 and/or a portion of the elongate shaft 104). The venting cannula can include a venting element that includes a filter that is removably coupled to or integrated with the cannula. The heating element can be arranged to be in contact with or extends through the filter.

A surgical system for supplying insufflation gases to a surgical cavity, such as any surgical systems (for example, insufflation systems) disclosed above, can incorporate any of the example venting cannulas disclosed herein. As described above, the system can include a gases supply configured to provide the insufflation gases, a humidifier in fluid communication with the gases supply and configured to humidify the insufflation gases received from the gases supply, and a gases delivery tube extending between and in fluid communication with the humidifier and the cannula, respectively. The gases delivery tube can also be in electrical communication with the humidifier and the cannula, respectively. When the system is in use, the gases delivery tube can direct the insufflation gases into the surgical cannula and can also direct an electrical current from the humidifier to the heating element within the cannula. A heating element can be configured to transfer heat to the insufflation gases passing through the cannula, and/or a portion of the medical instrument inserted into and/or removed from the cannula, to raise the temperature of the gases and/or the instrument to so as to reduce condensation and/or fogging. The temperature of the insufflation gases and/or the instrument can be increased above a dew point to prevent condensation of the gases and/or reduce condensation (and/or remove by evaporation condensation already formed) on the medical instrument. Condensation can also occur without external heat or humidification. For example, condensation can result from the inherent temperature (body heat) and humidity (body moisture) of the surgical cavity, and/or from the temperature and humidity of an insufflation fluid. The temperature of the insufflation gases and/or the instrument can be increased above a dew point to prevent condensation on the medical instrument as a result of the insufflation gases and/or surgical cavity.

As described herein, a proximal direction with respect to a cannula generally can refer to the top end of the cannula upper housing, while a distal direction with respect to a cannula generally can refer to the bottom end of the cannula shaft configured to be the first section of the cannula inserted into the surgical cavity.

More detailed examples of the venting cannulas are described below. As described herein, a proximal direction with respect to a medical instrument generally can refer to the top end of the medical instrument body, while a distal direction with respect to a medical instrument generally can refer to the bottom end of the medical instrument body configured to be the first section of the medical instrument inserted into the cannula and/or surgical cavity. Reference numerals of the same or substantially the same features may share the same last two digits.

Examples of a Venting Cannula

Figure 3A:
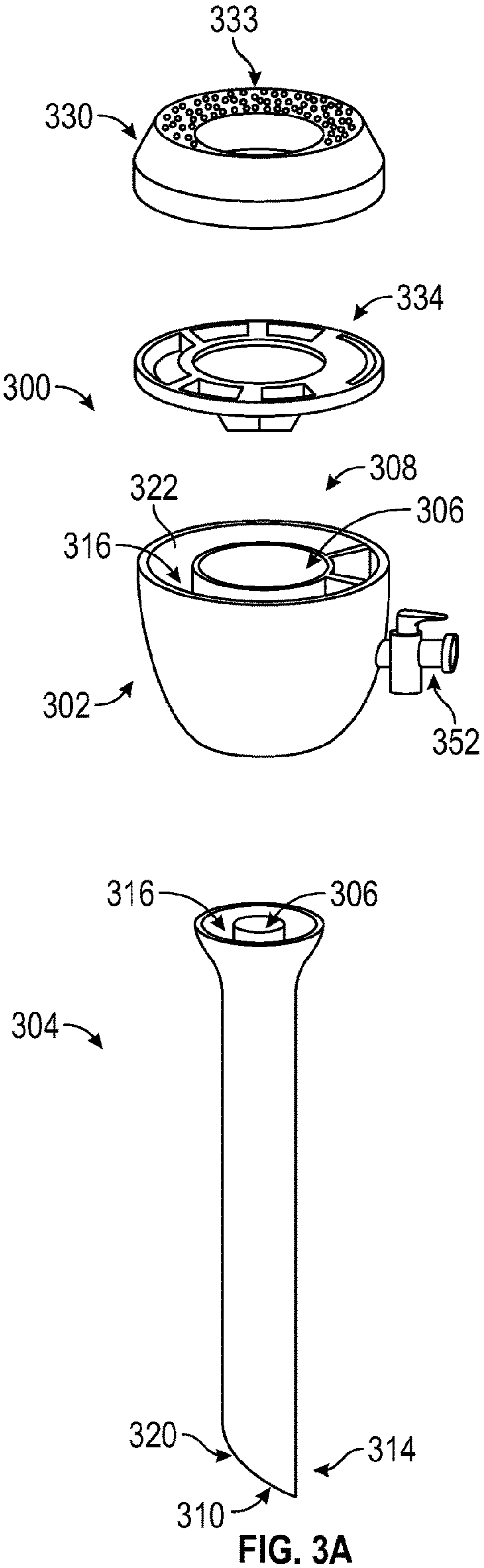
FIGS. 3A-3B illustrate perspective and longitudinal sectional exploded views of a double concentric lumen cannula including a removable filter and seal.

FIG. 3A is an exploded perspective view of a cannula including a removable or integrated filter and seal, according to some embodiments. The cannula 300 can include a cannula upper housing 302 and an elongate shaft 304 extending, e.g., distally from the cannula upper housing 302. The cannula upper housing 302 and elongate shaft 304 can both comprise a first lumen 306 (e.g., continuous between cannula upper housing 302 and elongate shaft 304) comprising an inlet 308 and an outlet 310. The first lumen 306 can be configured to receive insufflation gases delivered from a gas entry port 352 in the cannula upper housing 302 and deliver the insufflation gases through an outlet 310 proximate a distal end 314 of the elongate shaft 302 and into a surgical cavity. The first lumen inlet 306 can be in fluid communication with a source of the insufflation gases via the gas entry port 352. The cannula upper housing 302 and the elongate shaft 304 can also include a second lumen 316 comprising an inlet 320 and an outlet 322, the second lumen 316 configured to receive gases through the second lumen inlet 320 from the surgical cavity and vent and optionally filter the gases through the second lumen outlet 322 outside the surgical cavity. In other words, one lumen (e.g., the first lumen 306) can deliver fresh insufflation gases in a first direction, such as into a surgical cavity for example, while another lumen (e.g., the second lumen 316) can deliver gases, smoke, and other "waste" gases in a second, opposite direction, such as out of the surgical cavity for example.

Still referring to FIG. 3A, in some embodiments as shown the cannula 300 can include a double concentric lumen geometry, where one of the lumens is nested within another lumen. In some embodiments, the first lumen 306 can be nested partially or completely within the second lumen 316 as illustrated. In some embodiments, the second lumen 316 could have a larger diameter and/or cross-sectional area than a diameter of the first lumen 306 as shown, or a smaller or the same diameter and/or cross-sectional area in other embodiments. In some embodiments, the diameter of the second lumen can be between about 5% and about 90% of the diameter of the first lumen. In some embodiments, the first lumen and second lumen can have larger diameter zones proximally in the cannula upper housing 302 and smaller diameter zones distally in the elongate shaft 304 as shown, or substantially constant diameters throughout in other embodiments.

The second lumen 316 can be in fluid communication with a seal housing 330 that can include an instrument opening 333, a filter operably connected to the cannula 300, such as integrally formed or removably attachable (e.g. via a clip or other mechanism) to a proximal end of the cannula upper housing 302 for example. In some embodiments, the seal housing 330 forms, or is operably attached to the proximal-most portion of the cannula 300. A first seal 331 can also be present and integrally formed or removably attachable to the seal housing 330. The first seal 331 could be a duck-billed seal, flaps made of silicone or other appropriate material, or other type of seal. The filter may be coupled to an additional material, such as a desiccant material (e.g., silica) for example which can act to reduce the vapor content and increase the longevity and effectiveness of the filter. A retaining ring 334 could also optionally be present, such as in between the cannula upper housing 302 and the seal housing 330 for example.

Figure 3B:
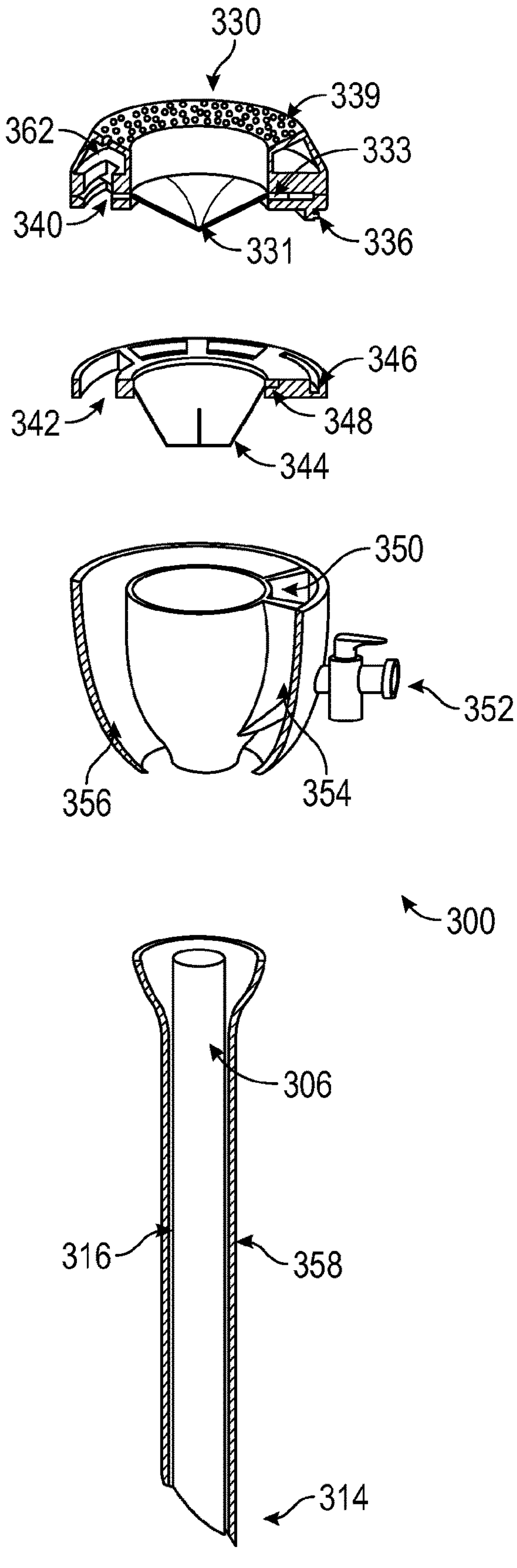
Figure 3C:
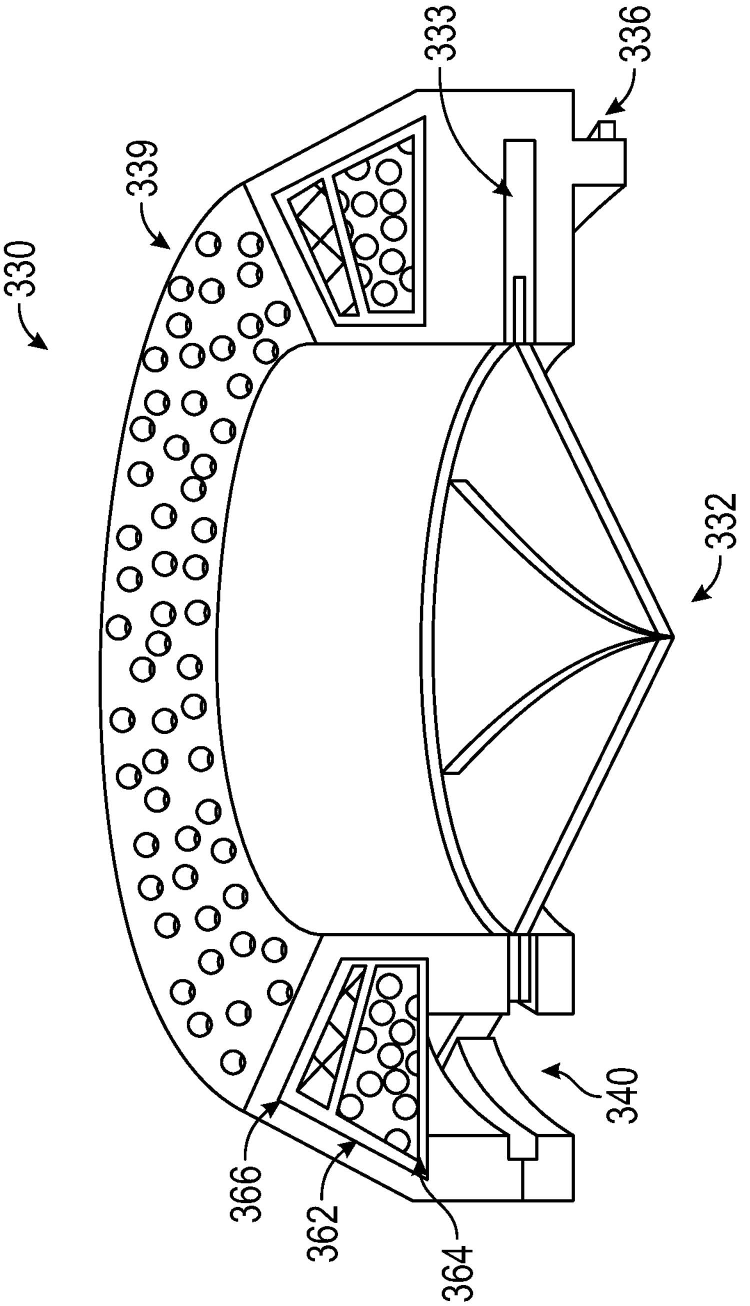
FIG. 3C illustrates a cross sectional view of the seal housing.

FIG. 3B illustrates a cross-sectional view of the exploded view embodiment of the cannula 300 of FIG. 3A. FIG. 3C illustrates a cross sectional view of the seal housing 330 with an additional material, as described below. Illustrated is the first lumen 306 and second lumen 316 as previously described. The outer lumen (e.g., second lumen 316) can include positioning or guide ribs 358 placed around the first lumen 306 and configured to be placed around the first lumen 306 to secure the position of the first lumen 306. In some embodiments, about or at least about 1, 2, 3, 4, 5, 6, 7, 8, or more guide ribs 358 can be present. If a plurality of guide ribs 358 are present, they can be spaced apart and sufficiently thin to ensure that gas venting flow is not disrupted. In some embodiments, the ribs 358 can have a thickness that is less than about 25%, 20%, 15%, 10%, 5%, or less of the inner diameter of the respective lumen containing the ribs 358, or ranges including any two of the foregoing values. In some embodiments, the guide ribs 358 are integrally formed with an inner wall of the second lumen 316, or otherwise attached.

The cannula upper housing 302 can include a gas entry port 352 fluidly connected to the first lumen 306 via gas entry channel 354, and a solid wall can be present to isolate the second lumen 316 from the first lumen 306 and ensure that no or substantially no leaking or mixing occurs between fresh insufflation gases and waste gases collected from the surgical cavity.

The gas entry port 352 can include a valve or other mechanism to control gas intake. The gas entry channel 354 can be sealed proximally by a section 350 that can be ultrasonically welded, bonded, or otherwise attached to the cannula upper housing 302. The second lumen 316 can include one, two or more seals leading to a seal housing 330 that can include one or more filters. The gases from the surgical cavity can pass through channel 356 that can be a proximal portion of the second lumen 316. Seal housing 330 can in some embodiments form the proximal-most end of the cannula 300. The seal housing 330 could have an arcuate, e.g., ring-like shape as shown or other geometries, and include venting slots 340 configured to allow the gases from the surgical cavity to reach the filter and be vented. Also illustrated is a pocket 362 configured to house one, two, or more gas filters. The filters could be, for example, carbon filters, high-efficiency particulate air (HEPA) filters, and/or ultra-low particulate air (ULPA) filters, and be between the venting slots 340 and venting apertures 339 configured to allow the filtered gases from the surgical cavity to escape into the outside environment. The filters can include multiple filter elements that can be positioned in series. For example, ULPA filters and carbon filters can be positioned in series, for example. FIG. 3C illustrates the pocket 362 configured to house an additional material 364, such as a desiccant material (e.g., silica) for example, with the one or more gas filters 366. Also illustrated is first seal 332 for medical instruments (e.g., endoscopes and other tools) to be placed therethrough, which can be centrally located in some embodiments and placed within a proximal section of a lumen, such as first lumen 306 for example. The seal 331 can be overmoulded in a component 333 made of hard plastic, silicone, rubber, or another desired material, or otherwise attached to a peripheral portion of the seal housing 330. A locking mechanism 336 can connect the seal housing 330 including the filters to a complementary locking mechanism 346 on the retaining ring 334, which includes second seal 344 configured to fit medical instruments therethrough. The locking mechanisms 336, 346 could include complementary flanges, clips, retainers, press-fit surfaces, threads, and the like. The retaining ring 334 can also include venting slots 342 configured to allow gases from the surgical cavity to reach the filter and then be vented into the environment. In some embodiments, the seal housing 330 and the retaining ring 334 can be permanently rather than removably coupled together, or integrally formed in some cases.

Figure 4:
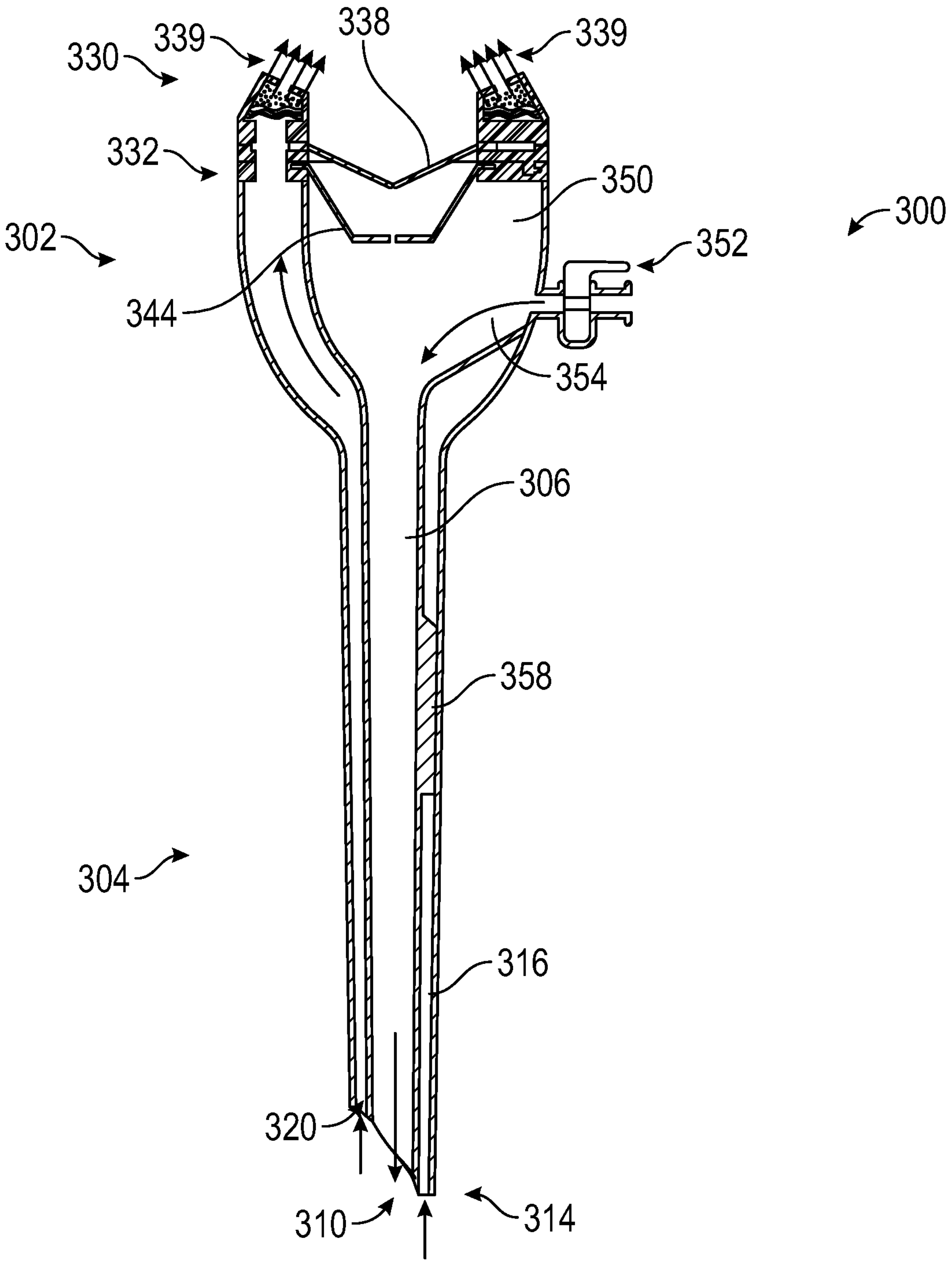
FIG. 4 illustrates a non-exploded cross-sectional view of the venting cannula embodiment including double concentric lumens as illustrated in FIGS. 3A and 3B.

FIG. 4 illustrates a non-exploded cross-sectional view of the venting cannula embodiment 300 including double concentric lumens as illustrated in FIGS. 3A and 3B. As shown, insufflation gases can enter the cannula 300 via gas entry port 352 and into the first (e.g., central) lumen 306 in the direction of arrows, and through the outlet 310 at the distal end 314 of the elongate shaft of the cannula 300 into the surgical cavity. Gases from the surgical cavity can flow in the opposite direction, entering the second (e.g., outer) lumen 316 of the cannula 300, flowing proximally through the cannula 300, through filter in seal housing 330, and out venting apertures 339 into the environment.

Figure 5A:
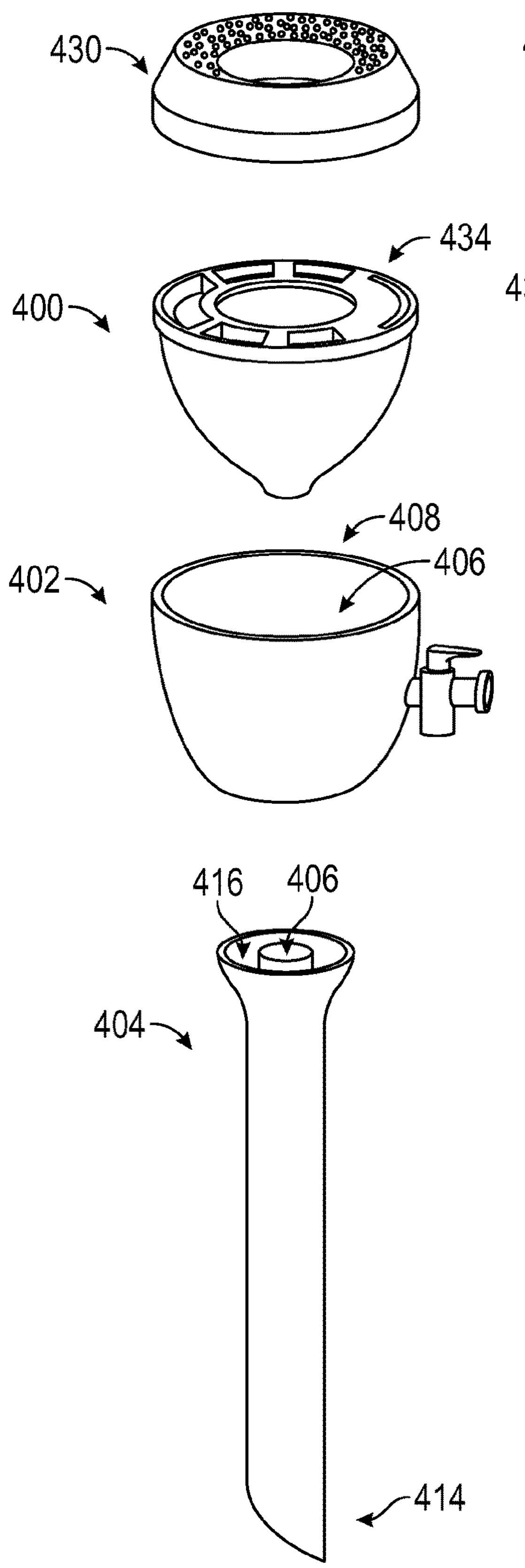
FIG. 5A is an exploded view of another embodiment of a cannula including a venting element including a removable filter and seal.
Figure 5B:
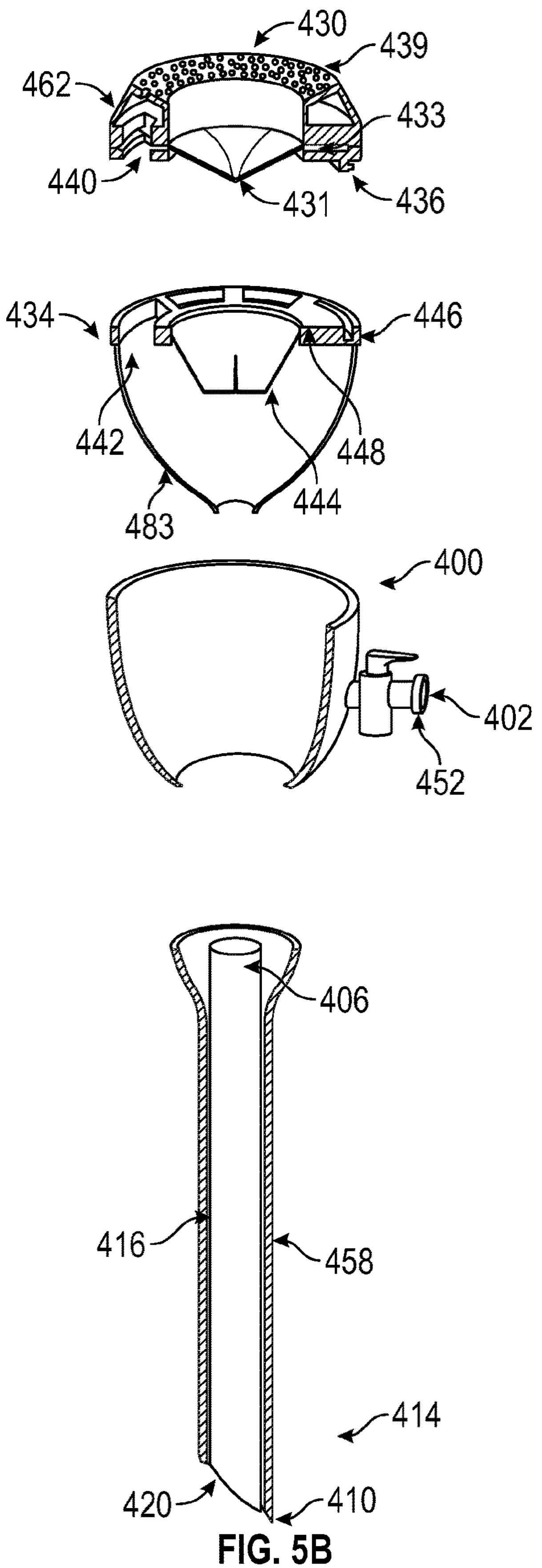
FIG. 5B illustrates cross-sectional view of the exploded view embodiment of the cannula 400 of FIG. 5A.

FIG. 5A is an exploded view of another embodiment of a cannula 400 including a seal housing 430 including a removable or integrated filter and seal 431. Multiple filters can be disposed, e.g., in series within the seal housing 430, such as multiple-stage filters for example. FIG. 5B illustrates cross-sectional view of the exploded view embodiment of the cannula 400 of FIG. 5A. Cannula 400 can incorporate any of the features of cannula 300 except that the function of the first and second lumens can be reversed in some embodiments. In some embodiments as shown, the first (e.g., central) lumen 406 is configured to receive gases through the first lumen inlet 420 from the surgical cavity (in contrast to sending gases into the surgical cavity as with FIGS. 3A-4) and vent the gases through the venting apertures 439 in the seal housing 430 outside the surgical cavity, while the second lumen 416 can be configured to receive insufflation gases delivered from a gas entry port 452 in the cannula upper housing 402 and deliver the insufflation gases from an outlet 410 proximate a distal end 414 of the elongate shaft 404 and into a surgical cavity. The second lumen 416 can be in fluid communication with a source of the insufflation gases, such as gas entry port 452 that can include a valve as previously described for example. The first lumen 406 can be removably or permanently attached, such as ultrasonically welded at 483 for example to the retaining ring 434. Also illustrated are venting slots 440, pocket 462 configured to house gas filters, seal 438 for medical instruments, seal overmoulded component 433, locking mechanism 436 for connecting the seal housing 430 to a complementary locking mechanism 446 on the secondary seal 444 with venting slots 442 that can all be as previously described.

Figure 6:
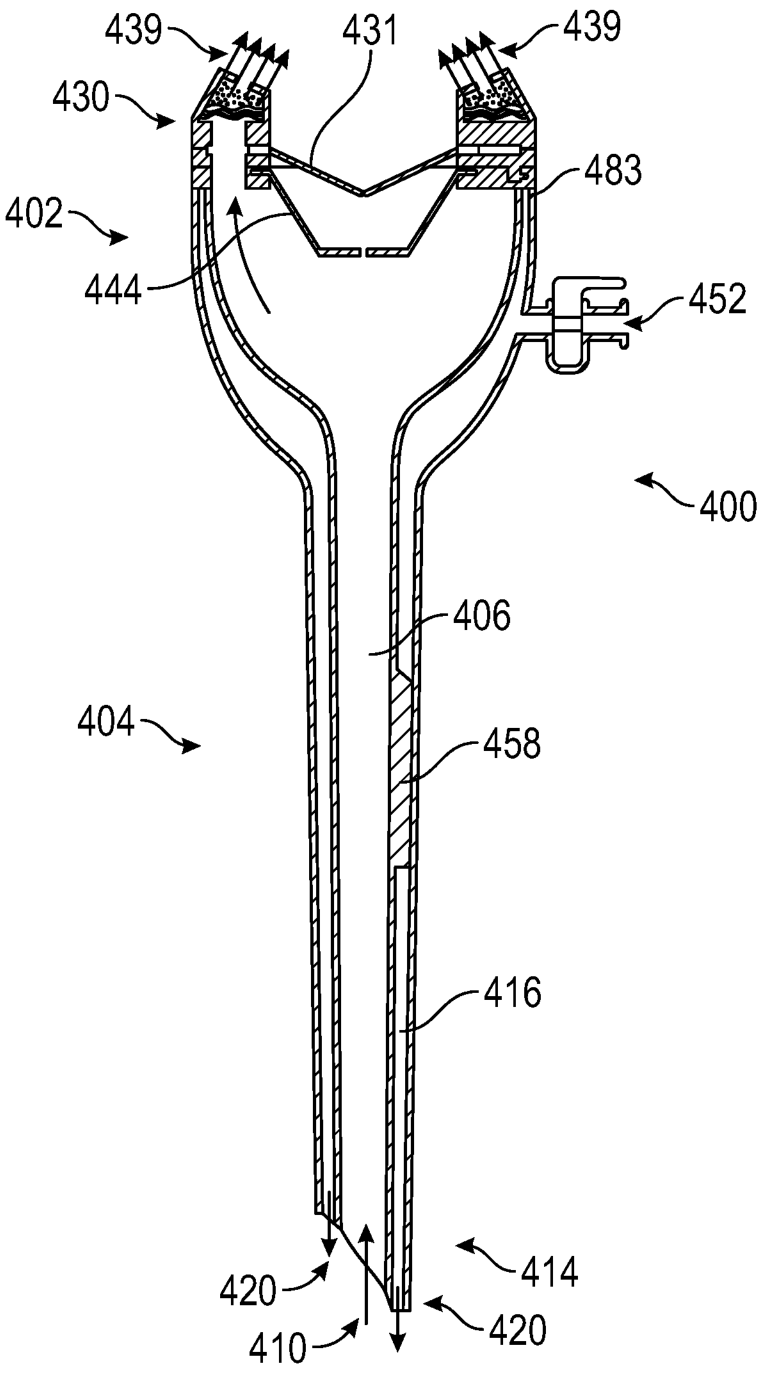
FIG. 6 illustrates a transverse cross-sectional view of the cannula of FIGS. 5A-5B.

FIG. 6 illustrates a non-exploded cross-sectional view of the venting cannula embodiment including double concentric lumens as illustrated in FIGS. 5A and 5B. As shown, insufflation gases can enter the cannula 400 via gas entry port 452 and into the second (e.g., outer) lumen 416 in the direction of arrows, and through the outlet 410 at the distal end 414 of the elongate shaft of the cannula 400 into the surgical cavity. Gases from the surgical cavity can enter the first (e.g., central) lumen 406 of the cannula 400, flowing proximally through the cannula 400, through filter in seal housing 430, and out venting apertures 439 into the environment. The first lumen 406 can be removably or permanently attached, such as ultrasonically welded at 483 for example to the retaining ring 434 as previously described. The seal housing 430 can be permanently or removably connected (e.g., by being clipped together) to the retaining ring 434. The seal housing 430 can also be permanently or removably connected to another part of the cannula 400.

Figure 6A:
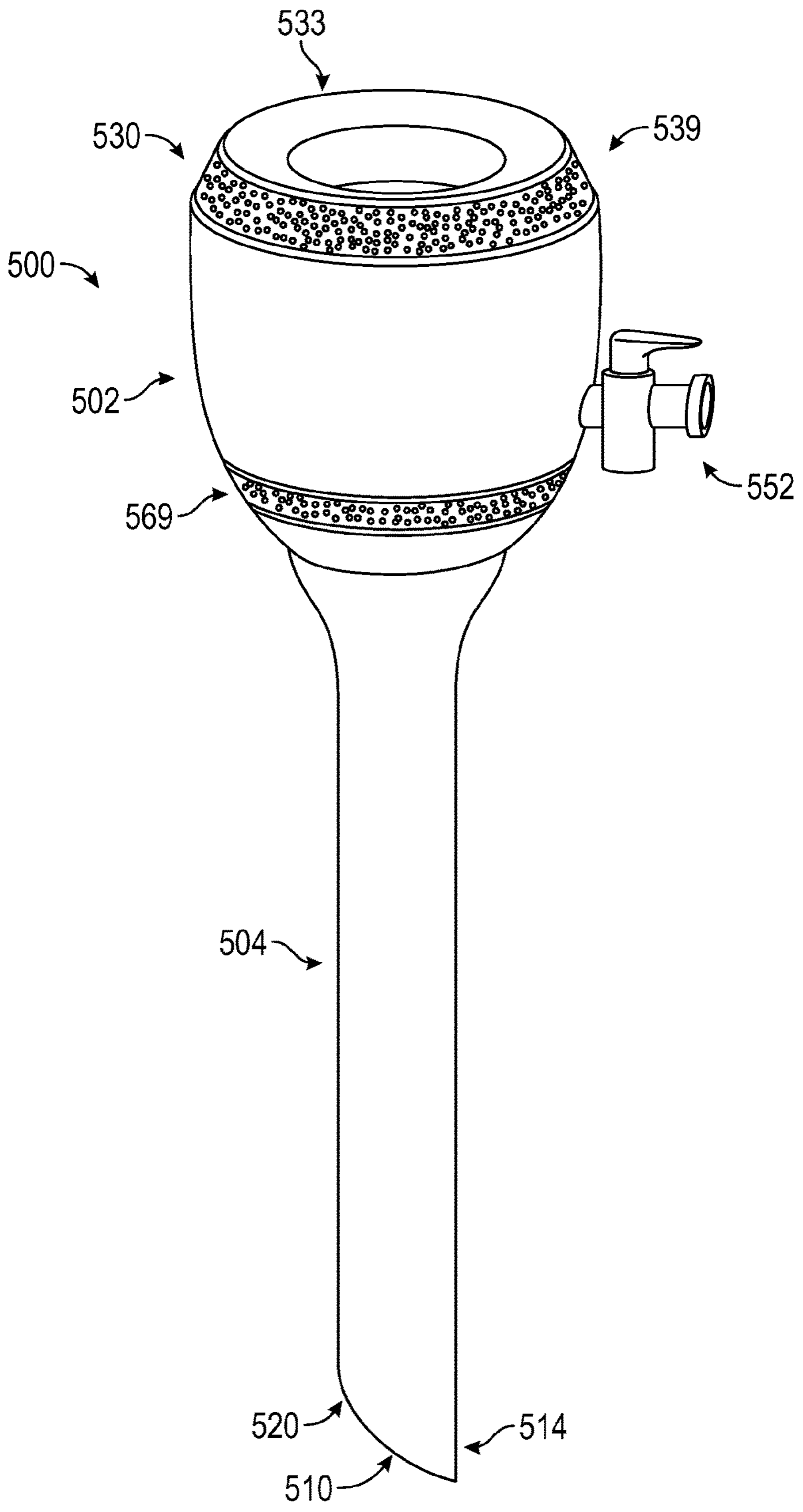
FIG. 6A is an isometric view of another embodiment of a cannula that can include multiple spaced apart filter elements.
Figure 6B:
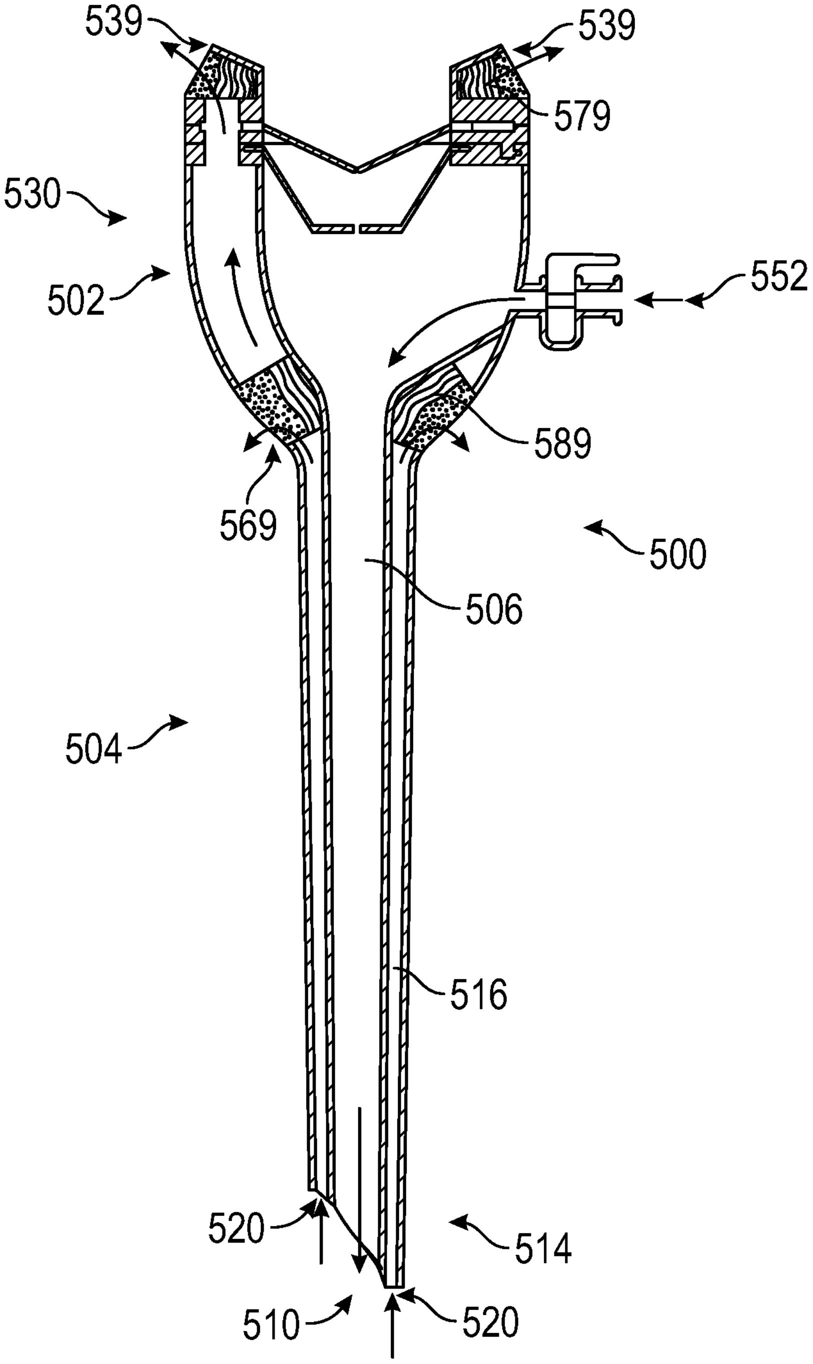
FIG. 6B is a longitudinal cross-sectional view of the embodiment of FIG. 6A.

FIG. 6A is an isometric view of another embodiment of a cannula 500 that can be similar to that of, and include any number of features as illustrated in FIGS. 5A-6 above, except that the cannula 500 includes multiple spaced apart filter elements. A first filter can be placed within the seal housing 530 as previously described, after which gases can be vented through a first set of venting apertures 539 in the seal housing 530 and outside of the surgical cavity. A second filter can be placed more proximally, such as in the upper cannula housing 502 for example, also including a second set of venting apertures 569 to allow for venting at a more proximal location. The first filter could be a different type of filter than the second filter. For example one filter could be a carbon filter, while the other filter could be a ULPA filter. Also illustrated is gas entry port 552, instrument opening 533, cannula elongate shaft 504, outlet 510 proximate a distal end 514 of the elongate shaft 504 of the cannula 500, and first lumen inlet 520 as previously described. FIG. 6B is a longitudinal cross-sectional view of the embodiment of FIG. 6A, also illustrating first filter 579 and spaced apart second filter 589, as well as outer lumen 516 and inner lumen 506 that can be as previously described.

Figure 7A:
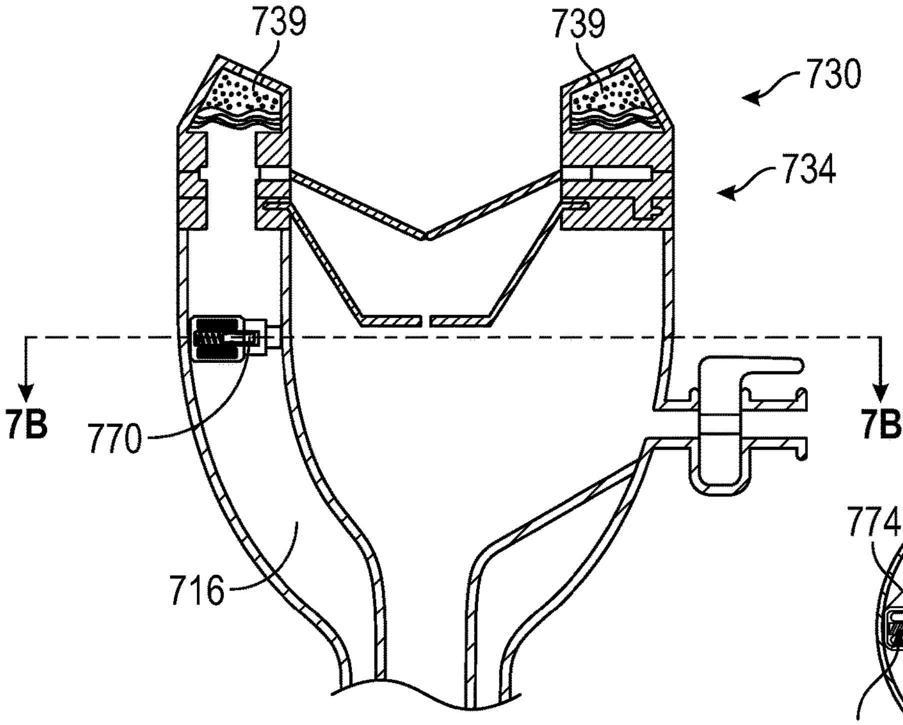
FIG. 7A illustrates the proximal end of a cannula including venting element with venting apertures.
Figure 7B:
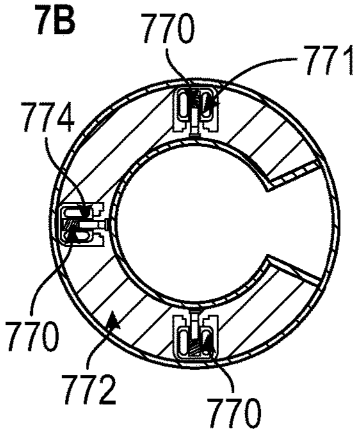
FIG. 7B is a cross-section through line 7B-7B of FIG. 7A.

In some embodiments, a venting cannula can include one, two or more valves in order to control venting into the environment (e.g., the operating room suite). FIG. 7A illustrates the proximal end of a cannula including the seal housing 730 with venting apertures 739, and operably connected to retaining ring 734 as previously described. The valves 770 can be present in the flow path of the lumen configured to vent gas from the surgical cavity, e.g., second or outer lumen 716 prior to reaching the seal housing 730 with venting apertures 739. FIG. 7B is a cross-section through line 7B-7B of FIG. 7A, illustrating a plurality of spaced apart valves 770. The valves can be configured in order to control the venting rate, e.g., the rate of gases being vented out of the cannula. The venting rate can be controlled to a predetermined rate such that smoke is cleared, smoke plumes are cleared from the surgical cavity. The solenoid valves may be controlled by a controller, e.g. a controller in a humidifier or a controller in the insufflator. The valves 770 could be, for example, solenoid valves, or other types of valves some of which are described elsewhere herein. Each valve 770 can be positioned in the flow path of the lumen configured to vent the gases, e.g., the second, e.g., outer lumen 716, and each include small venting apertures 771 controlled by the valve 770 to allow gases to subsequently pass through the filter. A solid plate 772 can hold the valves 770 in place by enclosing each of the valves 770 within their own housing 774. The plate 772 can be gas-impermeable and also be configured to act as a seal such that gases can only pass through the valves 770 in order to be vented.

Figure 7C:
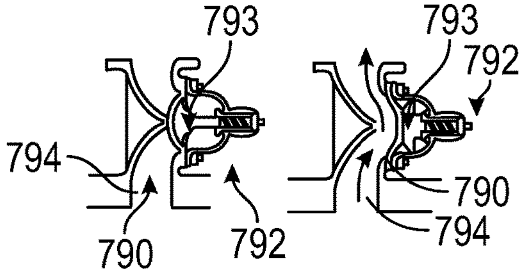
FIGS. 7C-7E illustrate various embodiments of venting valves can be utilized in connection with a venting cannula.

FIG. 7C illustrates another embodiment of a valve that can be a diaphragm pressure relief valve 792 positioned across the flow path 794 of the lumen. The valve 792 can have an initial closed state held by the pressure bias of a spring 793 as shown in the left side of FIG. 7C. A flexible seal 790 that can be made of a plastic or similar component can open (e.g., moving back toward the valve 792 as illustrated) when a pressure greater than the spring biasing pressure is applied by gases flowing within the flow path 794, thus moving the valve 792 into an open configuration as shown in the right side of FIG. 7C.

Figure 7D:
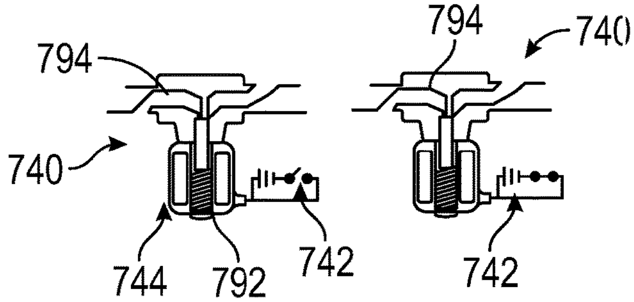

FIG. 7D illustrates another embodiment illustrating a solenoid valve 740. Similar to FIG. 7C the biasing force of a spring 793 can maintain the valve 740 in a closed state, as shown in the left side of FIG. 7D. A switch 742 is open when a circuit is off and the valve is closed. The switch 742 can be actuated (e.g., electrically) to open the valve 740, allowing gases to flow across the valve 410 and the flow path 794 as shown in the right side of FIG. 7D.

In some embodiments, a valve may be passive or active. Passive valves, e.g., spring valves or umbrella valves, are configured to vent at a predetermined pressure. The venting pressure corresponds to a pressure that can be used to maintain a constant pressure in the surgical cavity and provide a desired venting rate. Active valves are preferably actively controlled to achieve a constant pressure in the surgical cavity and vent smoke and smoke plumes and gases at a predetermined rate to achieve optical clarity. The passive openings, e.g. multiple openings or flow restricted openings, can be configured, e.g., shaped and structured to provide a desired venting rate.

Figure 7E:
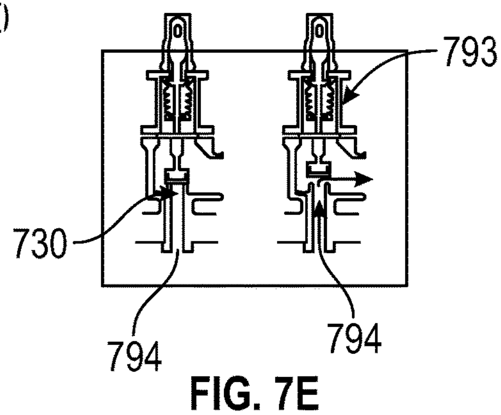

FIG. 7E illustrates another embodiment illustrating a pressure relief valve 730. As shown in the left hand side of FIG. 7E the biasing force of a spring 793 can exert a force sufficient to maintain the valve 730 in a closed position. As shown in the right hand side of FIG. 7E, when a pressure greater than the spring pressure is applied by gases flowing within the flow path 794, the valve 730 can move into an open configuration.

Figure 8A:
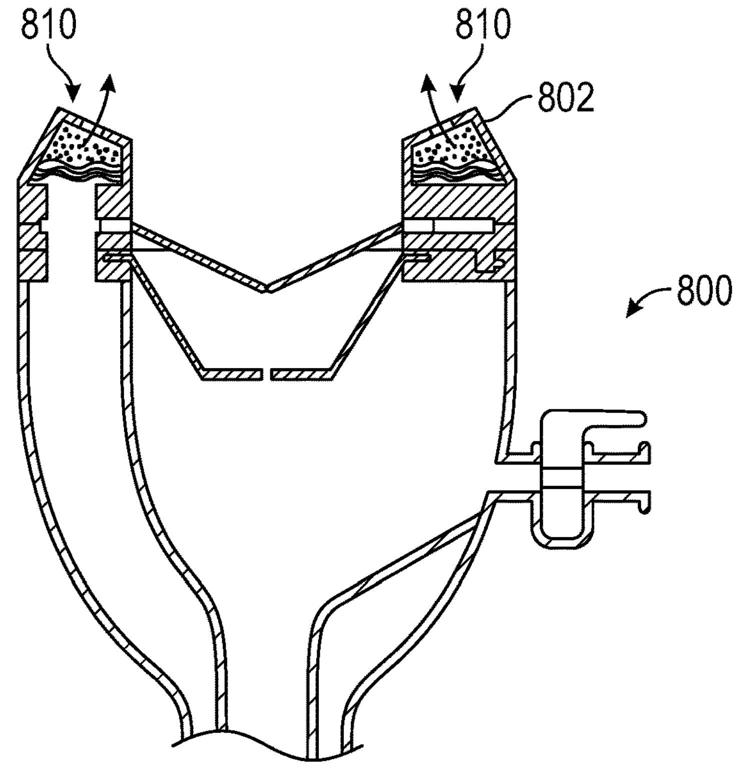
FIGS. 8A-8D illustrate additional mechanical/passive venting embodiments that can be included in venting cannulas, and may or may not include valves.
Figure 8B:
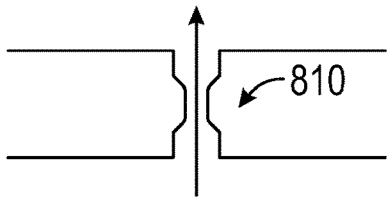
Figure 8C:
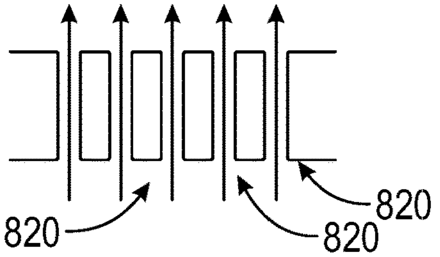
Figure 8D:
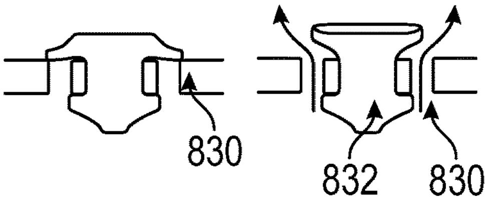

FIGS. 8A-8D illustrate additional mechanical/passive venting embodiments that can be included in venting cannulas, and may or may not include valves. The venting elements 810 can be positioned at or proximate the proximal end 802 of the cannula 800, as shown in FIG. 8A. FIG. 8B illustrates a venting element comprising only a single restriction orifice 810. FIG. 8C illustrate a venting element comprising a plurality of small spaced-apart orifices 820, such as 2, 3, 4, 5, 6, 7, 8, 9, 10, or more orifices 820. FIG. 8D illustrates a venting element that comprises an umbrella pressure relief valve 830. As shown on the left hand side of FIG. 8D, the valve 830 can "snap" and return to a closed state when no pressure is applied. As shown in the right hand side of FIG. 8D, a flexible seal 832 made of rubber or another material can open once a pressure greater than a predetermined value is applied by gases flow within the flow path.

Figure 9A:
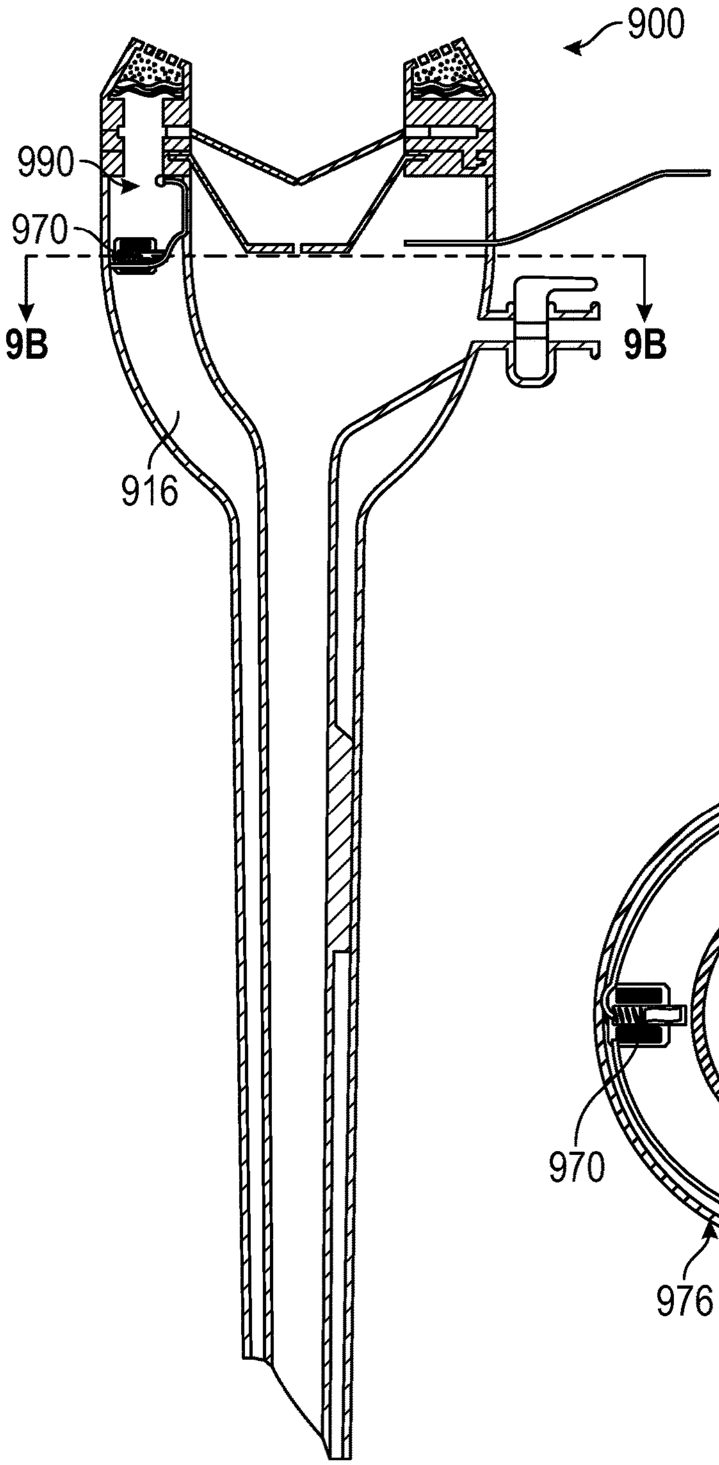
FIGS. 9A-9B illustrate various views of an embodiment of a venting cannula that can include electrical venting features.
Figure 9B:
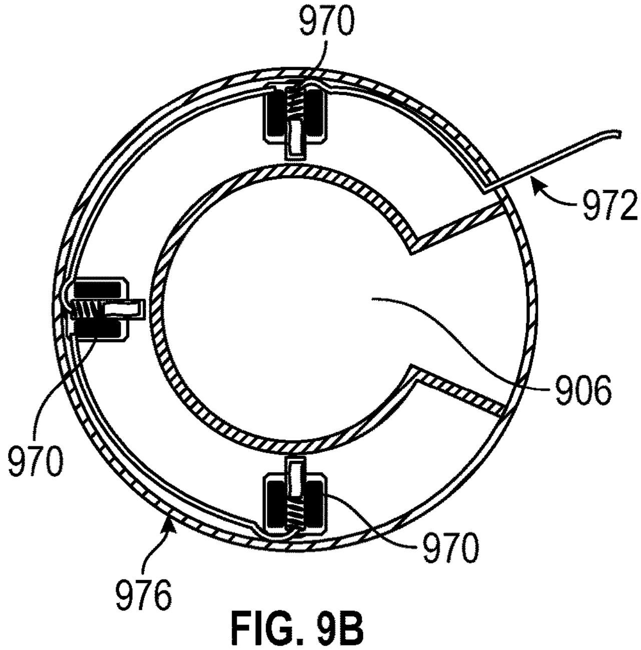

FIGS. 9A-9B illustrate an embodiment of a venting cannula 900 that can include electrical venting features. As shown in the longitudinal cross-sectional view of FIG. 9A, one or more sensors 990 can be present in the lumen configured to carry gases from the surgical cavity for filtering and venting (e.g., outer lumen 916). The sensor 990 can be configured to detect, for example, smoke and other noxious agents, particulates, carbon monoxide, and the like, and/or other gas parameters such as pressure, temperature, humidity, and/or flow for example. The sensor 990 can take continuous or intermittent sampling measurements as the gases are being vented. The sensor 990 can be molded or otherwise attached in place within the cannula 900 and be in wired or wireless communication with a controller. FIG. 9B is a cross-sectional view through line 9B-9B of FIG. 9A. Shown are valves 970, which can be solenoid gate valves actuatable via a controller integrated in the cannula or located elsewhere within the surgical insufflation and/or humidification system. A wire 972 can extend from the controller for the sensor 990 and solenoid valves 970 to control the venting gas flow. The wire 972 can be overmoulded in some cases in a cannula sidewall at 976 in order to seal the gas exit pathway. When the sensor 990 detects that a gas parameter meets or exceeds a predetermined or calculated threshold, the controller, receiving the data from the sensor 990, can signal the solenoid gate valve 970 (such as via wire 972 for example) to open and close to control venting of the gases.

Figure 10A:
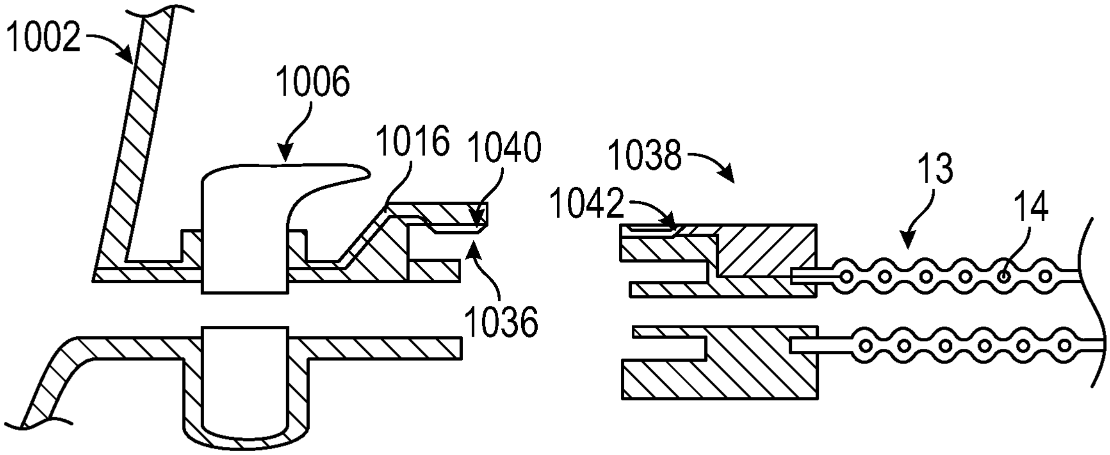
FIGS. 10A-10B illustrate disconnected and connected configurations of an additional example of a power supply to electrical elements of a venting cannula.
Figure 10B:
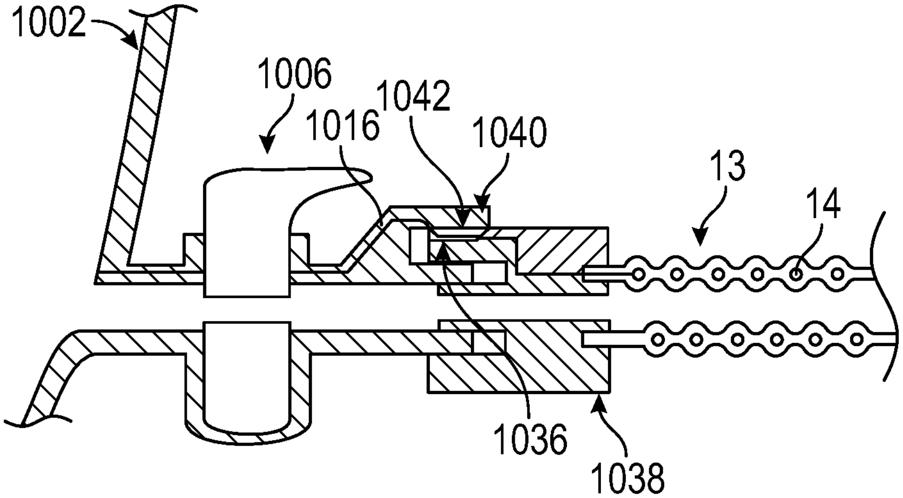

The example cannulas disclosed herein can also include a socket connection (e.g., delivered by tube set) for supplying power to the heating element via the one or more electrical wires. As shown in FIGS. 10A-10B, the gases inlet 1006 of the cannula can include an electrical connector 1036. The electrical connector 1036 can be in electrical communication with the one or more electrical wires 1016. The one or more electrical wires 1016 can be embedded within (for example, overmoulded in) the wall of a partial length of the cannula upper housing 1002 and also optionally the wall of a partial length of the elongate shaft, extending between the heating element in the cannula and the electrical connector 1036.

The electrical connector 1036 can be configured to couple to a corresponding connector 1038 (for example, a socket connector) on a gases delivery tube 13 of a surgical system (such as an insufflation system, or any of the surgical systems disclosed herein for example) to supply power to the heating element. The gases delivery tube 13 can include a helically wound tube that is moulded into the corresponding connector 1038, which can include a hard plastic material. The socket connection can secure the gases delivery tube 13 to the cannula. As shown in FIGS. 10A and 10B, the electrical connector 1036 can include a pin 1040 configured to be coupled to a PCB edge connector 1042 of the corresponding connector 1038 to establish electrical communication between the heating element and the heater wire circuit 14 of the gases delivery tube 13.

Figure 11A:
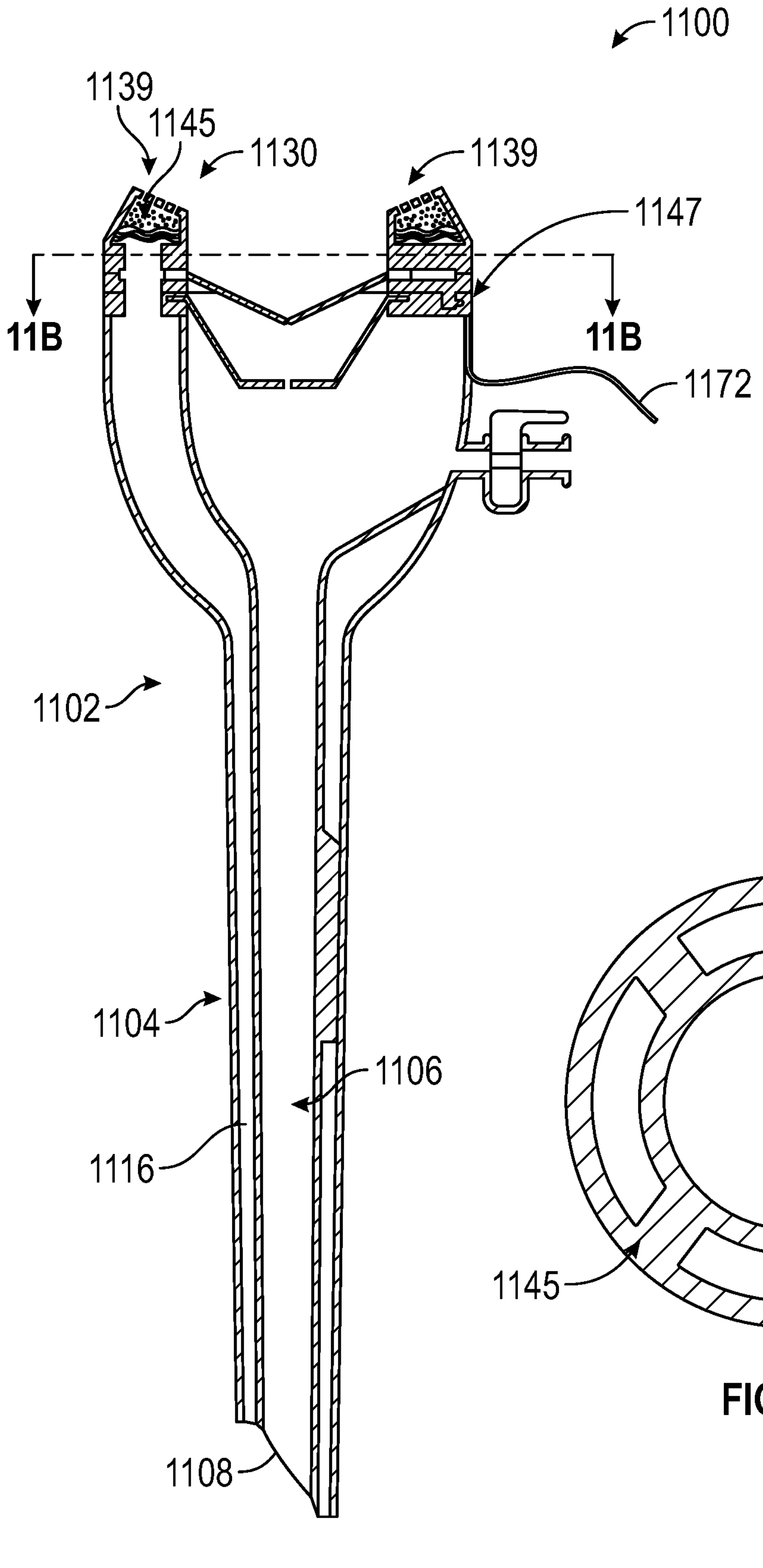
FIGS. 11A-11B illustrate sectional views of an embodiment of a dual lumen venting cannula 1100.
Figure 11B:
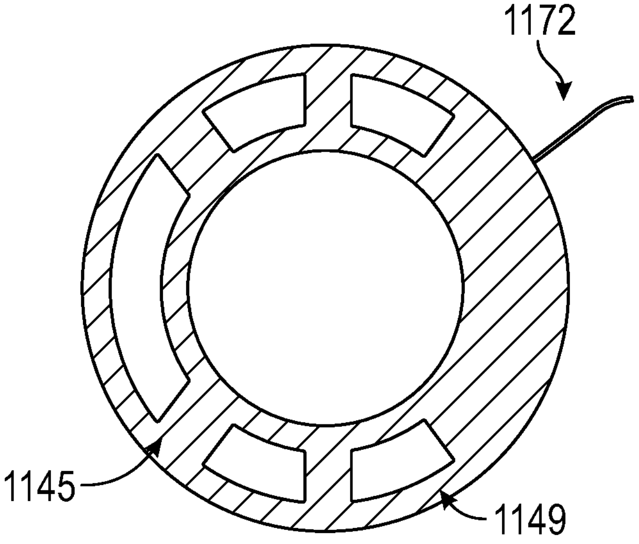

FIGS. 11A-11B illustrate sectional views of an embodiment of a dual lumen venting cannula 1100 that can include features as previously described, including cannula upper housing 1102, cannula elongate shaft 1104 configured to house a first lumen 1106 and second lumen 1116 therethrough, and the distal end 1108 of elongate shaft 1104 of the cannula 1100. Also shown is the seal housing 1130 which can include a heating element 1145 within the gas flow path of the seal housing 1130 and distal to the venting apertures 1139.

The heating element 1145 could include a printed circuit board (PCB) heater, heater wire which can include an insulated copper alloy resistance wire, other types of resistance wire, or other heater element, and/or be made of any other appropriate material. In some cases, the PCB could be flexible, or rigid and pre-shaped to an arcuate shape for example. A heater wire can be a straight wire or a helically wound element. The heating element 1145 can advantageously heat the gases to be vented sufficiently to prevent the gases from condensing and as such clogging the filter. In some embodiments, the heating element 1145 is configured to heat the gases to be vented to at least about 70, 80, 90, 100, 110, or more degrees Celsius, or ranges including any two of the aforementioned values, and/or above the dew point of the gases in some embodiments. An electrical connection to the PCB heater can be made in the filter compartment of the seal housing 1130, via electrical pins positioned between different layers of the cannula. FIG. 11B is a cross-section through line 11B-11B of FIG. 11A. As shown, the power to the PCB heater is provided, for example, by a wire connection 1172 to a power source in a connected surgical humidification system. In other embodiments, the power source could be directly connected to the cannula, or wireless. The PCB heater 1145 can be positioned within the cannula and configured such that the PCB 1149 does not come into direct contact with the gas flow path to avoid any contamination with the PCB itself.

A heating element can be embedded in a wall of the cannula upper housing in some cases. The heating element and/or other heating elements in this disclosure can be attached and/or disposed on an inner wall of the cannula (for example, the inner wall of the upper housing and/or the inner wall of the shaft). Alternatively the heating element examples may be wrapped around the outer surface of the cannula shaft. The heating element can be moulded into the wall of the cannula upper housing.

Figure 12A:
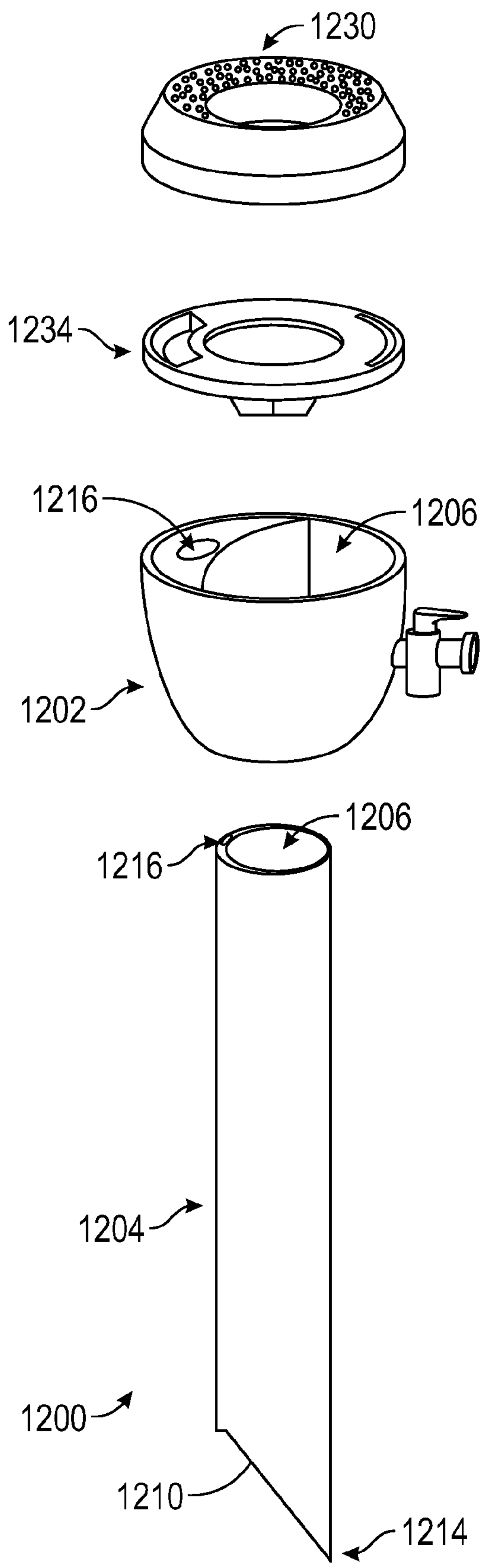
FIGS. 12A-12B illustrate an exploded view of another embodiment of a cannula including a venting element including a removable filter and seal.
Figure 12B:
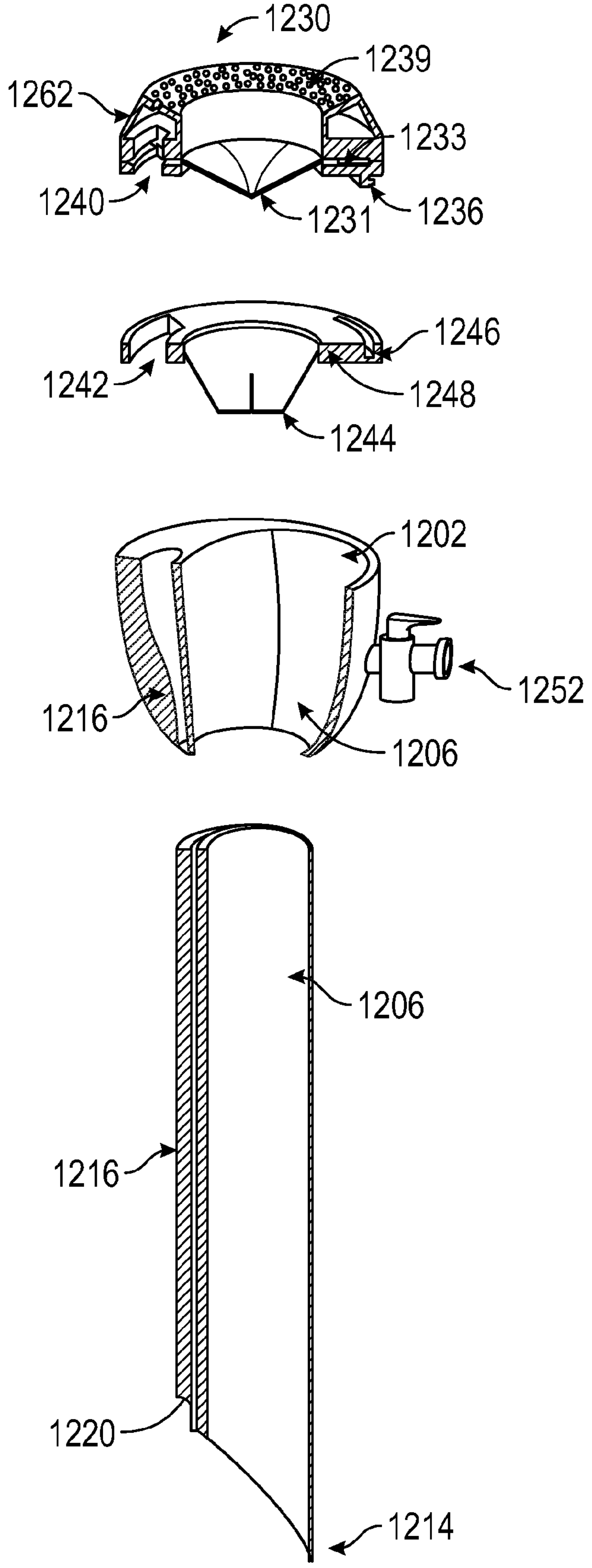

FIGS. 12A-12B illustrate an exploded view of another embodiment of a cannula 1200 including a seal housing 1230 including a removable or integrated filter and seal 1231. The filters can include multiple filter elements that can be positioned in series as described elsewhere herein. FIG. 12B illustrates cross-sectional view of the exploded view embodiment of the cannula 1200 of FIG. 12A. Cannula 1200 can incorporate any of the features of cannulas as described elsewhere herein, except the cannula 1200 includes a plurality of offset lumens (e.g., two or more lumens adjacent to each other, which are not nested or concentric with respect to each other). In some embodiments as shown, the first lumen 1206 is configured to receive gases through gas entry port 1252 in the cannula upper housing 1202 and deliver the insufflation gases from an outlet 1210 proximate a distal end 1214 of the elongate shaft 1204 and into a surgical cavity. The second lumen 1216 can transport gases from the surgical cavity via inlet 1220 and vent the gases through the venting apertures 1239 in the seal housing 1230 outside the surgical cavity. In some embodiments, the first lumen 1206 can have a diameter that is greater than the diameter of the second lumen 1216, such as at least about, about, or no more than about 10%, 25%, 50%, 75%, 100%, or more greater than the diameter of the second lumen 1216. In some embodiments, the first lumen 1206 can have a diameter that is the same, or less than that of the second lumen 1216. The seal 1231 of the seal housing 1230 can be overmoulded in hard plastic 1233 or other material as previously described. Also illustrated distal to the seal housing 1230 can be a removably or permanently attachable retaining ring 1234, which can include venting slots 1242 to allow gas to reach the filter and be vented, and a duckbill seal 1245 for medical instruments. Also illustrated are venting slots 1240, pocket 1262 configured to house gas filters as previously, seal 1231 for medical instruments, seal overmoulded component 1233, locking mechanism 1236 for connecting the seal housing 1230 to a complementary locking mechanism 1246 on the retaining ring 1234 with venting slots 1242 (for reversibly attachable embodiments), first seal 1231 and second seal 1244 that can all be as previously described.

Figure 13:
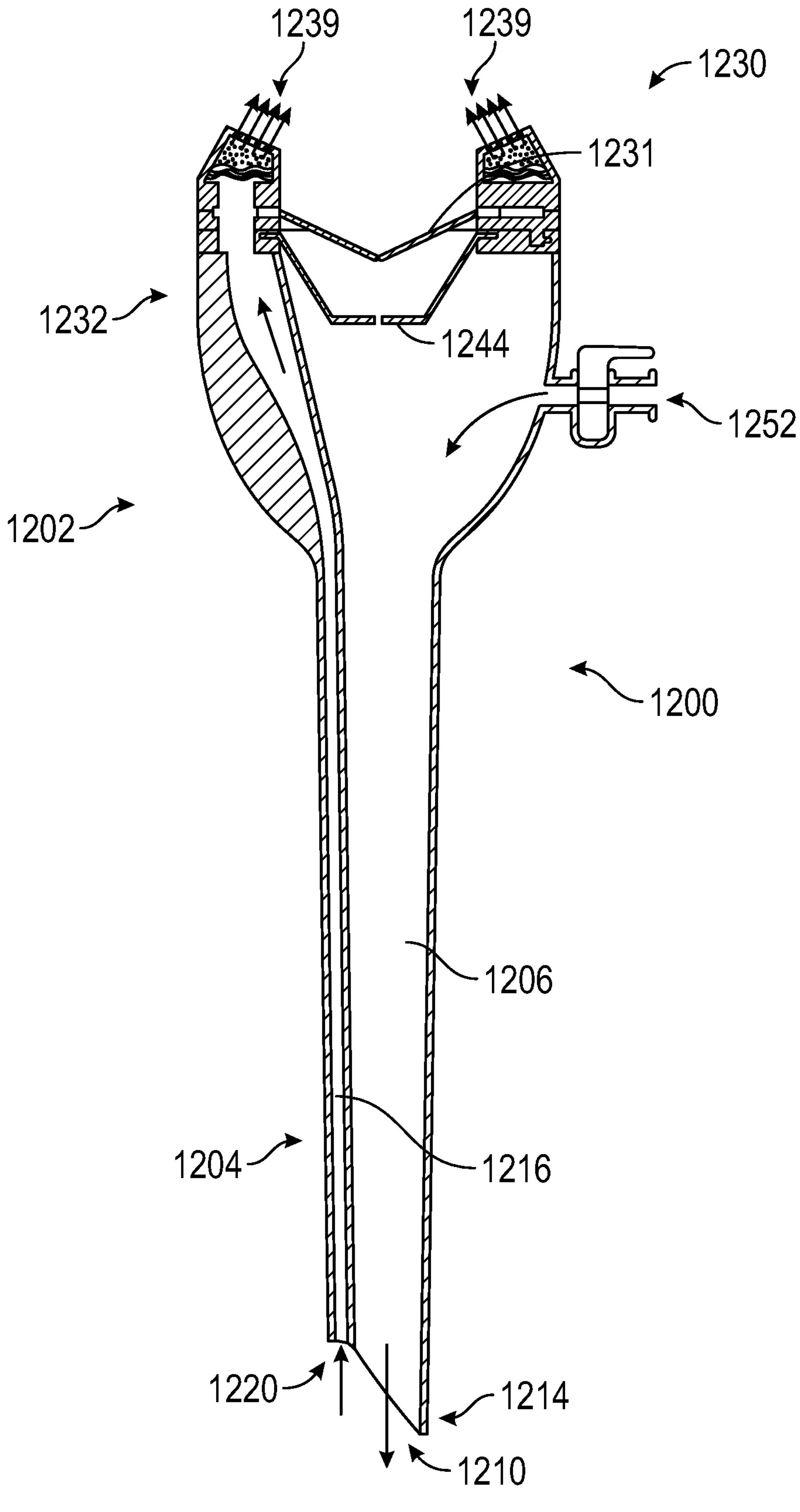
FIG. 13 illustrates a non-exploded longitudinal cross-sectional view of the venting cannula embodiment including double offset non-concentric lumens as illustrated in FIGS. 12A and 12B.

FIG. 13 illustrates a non-exploded longitudinal cross-sectional view of the venting cannula 1200 embodiment including double offset non-concentric lumens as illustrated in FIGS. 12A and 12B. As shown, insufflation gases can enter the cannula 1200 via gas entry port 1252 and into the first lumen (e.g., lumen 1206 in the direction of arrows, and through the outlet 1210 at the distal end 1214 of the elongate shaft of the cannula 1200 and into the surgical cavity. Gases from the surgical cavity can enter the second lumen 1216 of the cannula 1200, flowing proximally through the cannula 1200, through a filter in the seal housing 1230 with seal 1231, and out the venting apertures 1239 into the environment. Also shown are seals 1231, 124 which can be as previously described.

Figure 14:
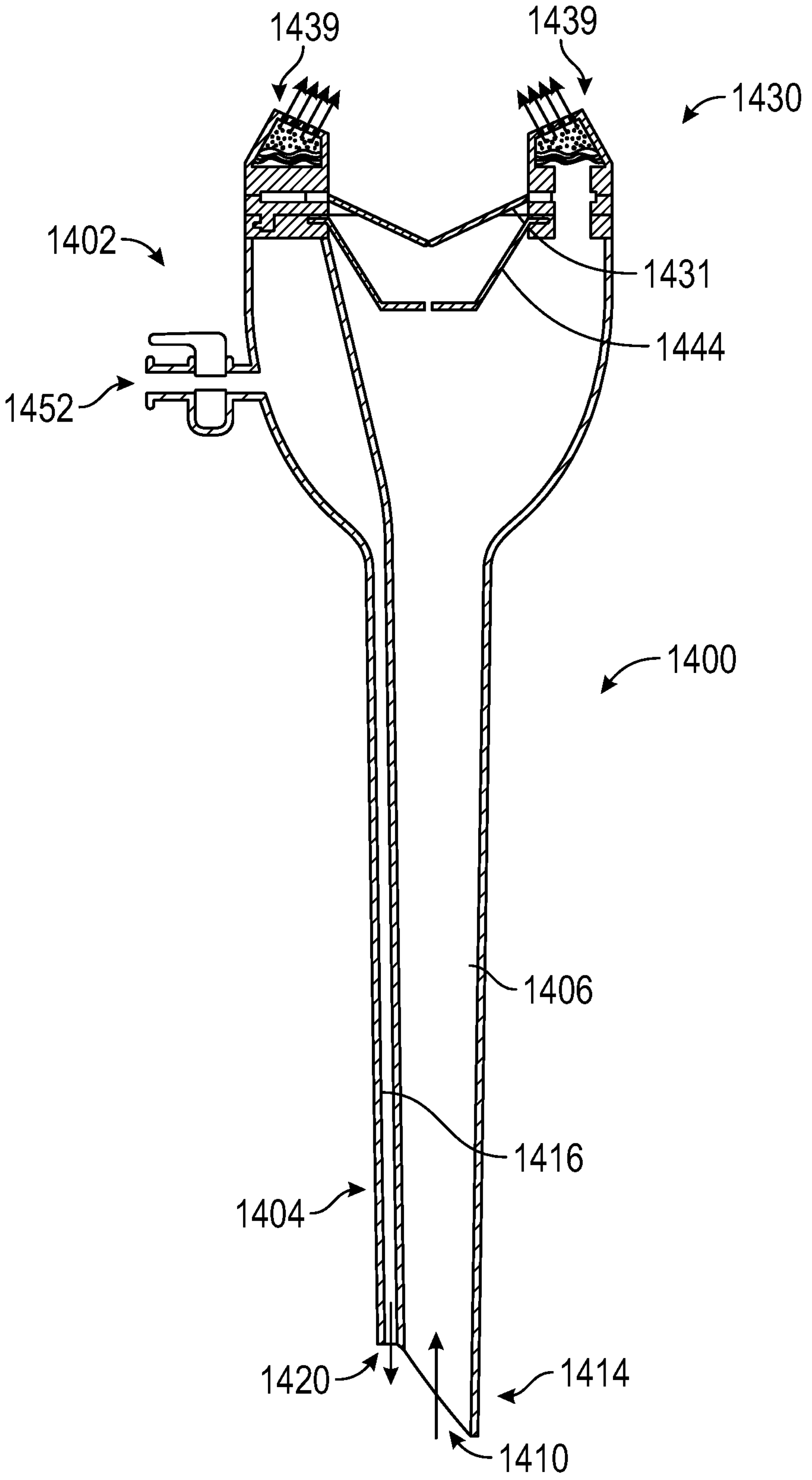
FIG. 14 illustrates a non-exploded longitudinal cross-sectional view of another embodiment of a double offset non-concentric lumen cannula.

FIG. 14 illustrates a non-exploded longitudinal cross-sectional view of another embodiment of a double offset non-concentric lumen cannula 1400 including a seal housing 1430 including a removable or integrated filter and seal 1431. Cannula 1400 can incorporate any of the features of cannula 1300 (or other cannula embodiments) except that the function of the first and second lumens can be reversed. In some embodiments as shown, the first (e.g., larger diameter) lumen 1406 is configured to receive gases through the first lumen inlet 1410 from the surgical cavity (in contrast to sending gases into the surgical cavity as with FIGS. 12A-13) and vent the gases through the venting apertures 1439 in the venting element 1430 outside the surgical cavity, while the second (e.g., smaller diameter) lumen 1416 can be configured to receive insufflation gases delivered from a gas entry port 1452 in the cannula upper housing 1402 and deliver the insufflation gases from an outlet 1420 proximate a distal end 1414 of the elongate shaft 1404 and into a surgical cavity. The second lumen 1416 can be in fluid communication with a source of the insufflation gases, such as gas entry port 1452 that can include a valve as previously described for example. Also illustrated are seals 1431, 1444 that can be as previously described.

Figure 14A:
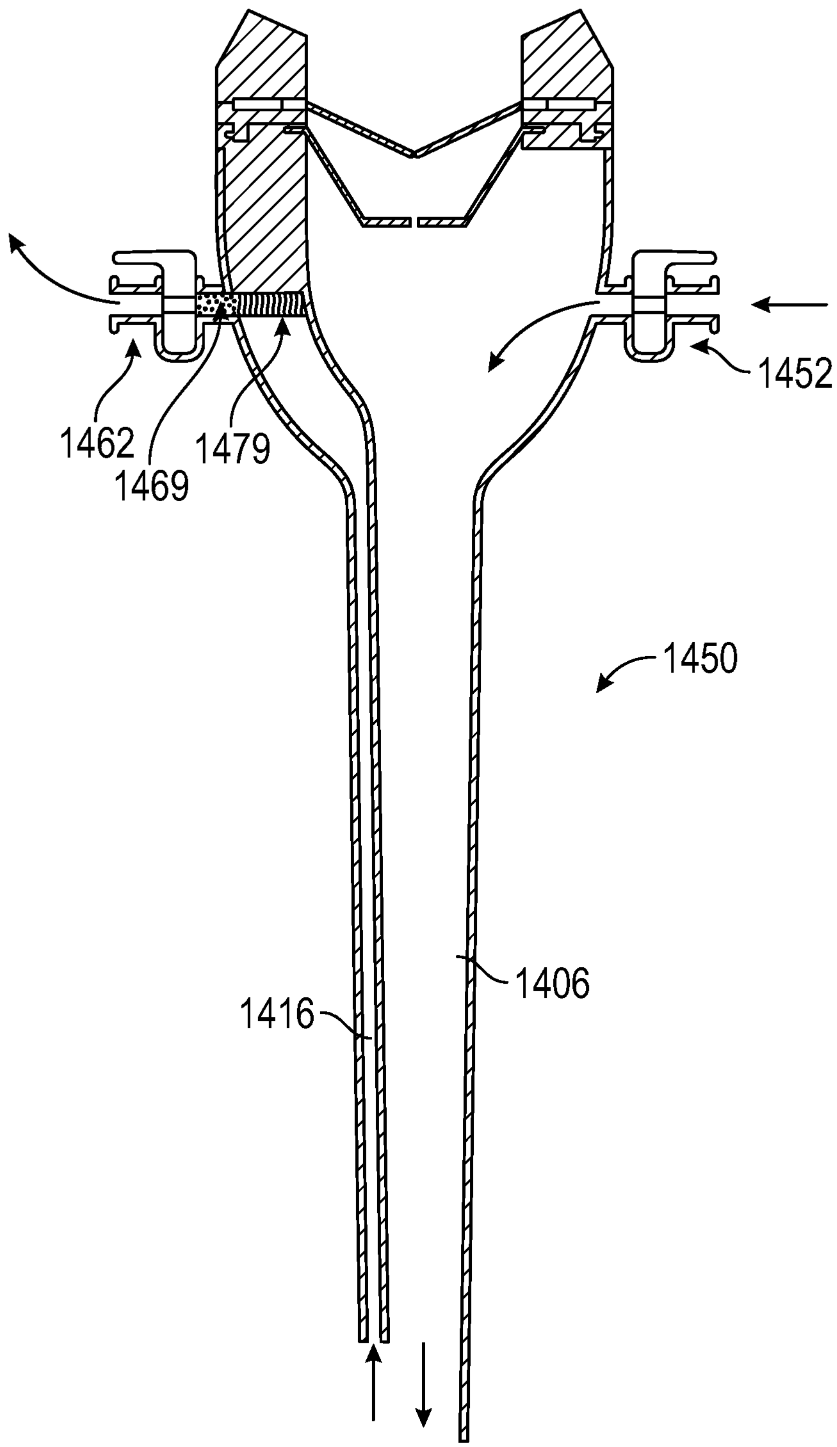
FIG. 14A illustrates a longitudinal cross-sectional view of another embodiment of a double offset non-concentric lumen cannula that can include a first port and a second port.

FIG. 14A illustrates a longitudinal cross-sectional view of another embodiment of a double offset non-concentric lumen cannula 1450 that can include any number of the features described in FIGS. 13 and 14, except that cannula 1450 can include a first port 1452 and a second port 1462. The first port 1452 can be a gas entry port as previously described in fluid communication with first lumen 1406. The second port 1462 can be a gas exit port configured to vent gases from the surgical cavity via second lumen 1416, and include one or more filters 1469, 1479 such as a carbon and ULPA filter, for example, or other filters as described elsewhere herein. The second port 1462 can substantially on the same axial level as the first port 1452 as illustrated, or axially offset in other embodiments. Such embodiments can advantageously control venting and insufflation via flow control through the ports 1452, 1462.

Figure 14B:
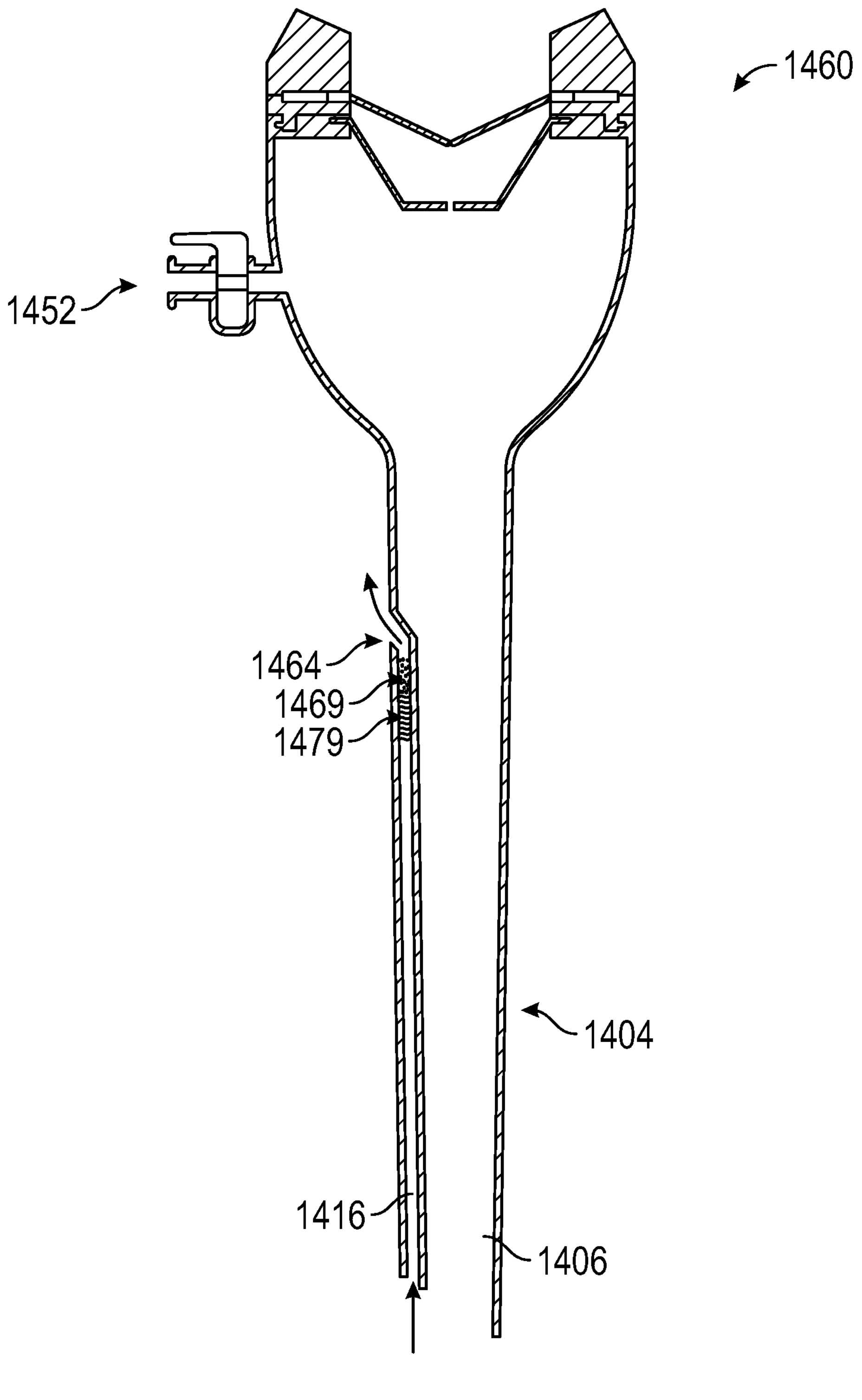
FIG. 14B illustrates a longitudinal cross-sectional view of another embodiment of a double offset non-concentric lumen cannula that can include a first port and a second port in the sidewall of the cannula elongate shaft.

FIG. 14B illustrates a longitudinal cross-sectional view of another embodiment of a double offset non-concentric lumen cannula 1460 that can include any number of features described in FIGS. 13 and 14, except that cannula 1460 can include a first port 1452 and a second port 1464 in the sidewall of, for example, the cannula elongate shaft 1404. The first port 1452 can be a gas entry port as previously described in fluid communication with first lumen 1406. The second sidewall port 1464 can be a gas exit port configured to vent gases from the surgical cavity via second lumen 1416, and include one or more filters 1469, 1479 such as a carbon and ULPA filter, for example, or other filters as described elsewhere herein. The second sidewall port 1464 can be distal on the cannula 1460 with respect to the first port 1452 as illustrated.

Figure 15A:
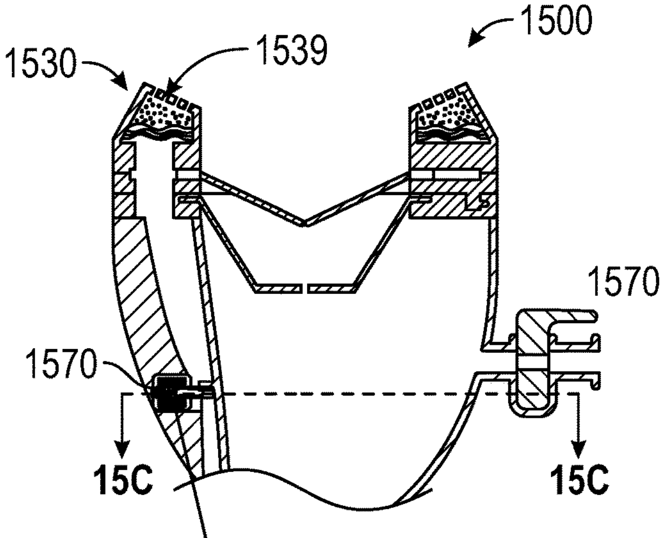
FIG. 15A illustrates the proximal end of a cannula including venting element with venting valves.
Figure 15C:
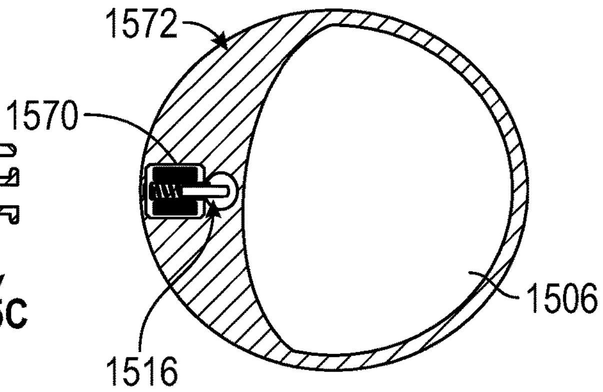
FIG. 15C is a cross-section through line 15C-15C of FIG. 15A.
Figure 15B:
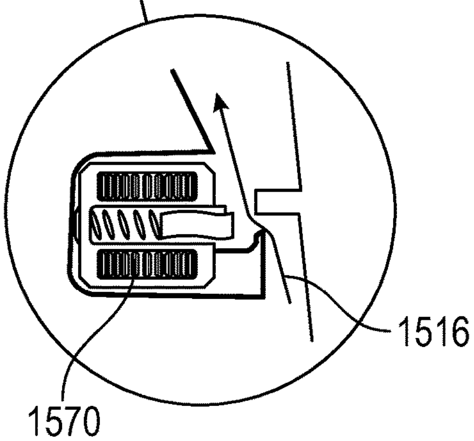
FIG. 15B is a close-up view of FIG. 15A, illustrating valve relative to the flow path of the second lumen across the valve.

FIG. 15A illustrates the proximal end of a cannula 1500 including seal housing 1530 with venting apertures 1539 as previously described. Valves 1570 can be present in the flow path of the lumen configured to vent gas from the surgical cavity, e.g., second lumen 1516 prior to reaching the seal housing 1530 with venting apertures 1539 as previously described. FIG. 15B is a close-up view of FIG. 15A, illustrating valve 1570 relative to the flow path of the second lumen 1516 across the valve. FIG. 15C is a cross-section through line 15C-15C of FIG. 15A, illustrating a valve configuration including one, two, or more solenoid valves 1570, or other types of valves some of which are described elsewhere herein. A single valve 1570 is illustrated moulded in the wall 1572 of the cannula 1500. The wall 1572 of the cannula 1500 can enclose the offset second lumen 1516 and hold the valve 1570 in place. A small venting hole within the second lumen 1516 can be controlled by the valve 1570 to selectively allow gases to pass through the filter. Offset first lumen 1506 is also shown. In some embodiments, the valve could include diaphragm pressure release valves, solenoid activated relief valves, and/or pressure relief valves as described elsewhere herein.

Figure 16:
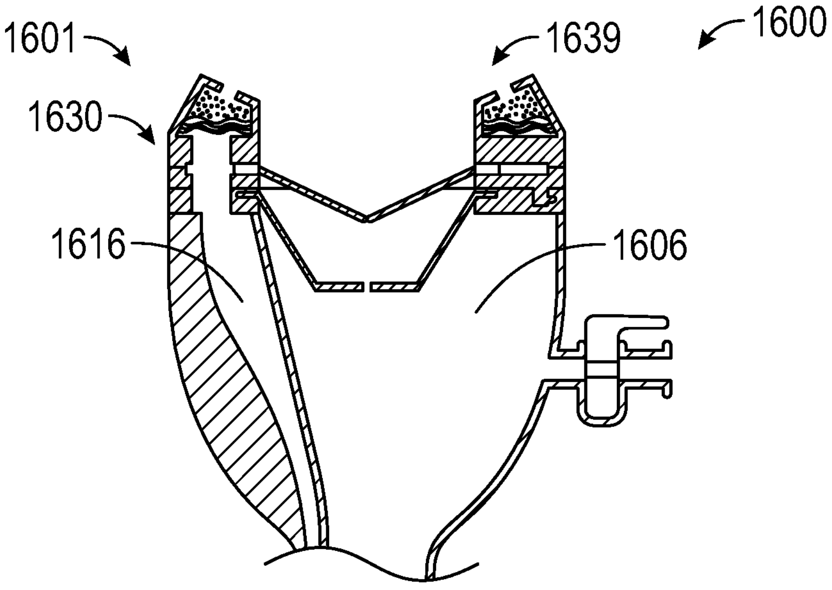
FIG. 16 schematically illustrates additional mechanical/passive venting embodiments that can be included in venting cannulas.

FIG. 16 schematically illustrates additional mechanical/passive venting embodiments that can be included in venting cannulas including those in connection with FIGS. 12A-13, for example, and may or may not include valves. The venting apertures 1639 of the seal housing 1630 can be positioned at or proximate the proximal end 1601 of the cannula 1600, and could comprise a single restriction orifice, a plurality of small spaced-apart orifices, an umbrella pressure relief valve, or other natural venting options as previously described herein.

Figure 17A:
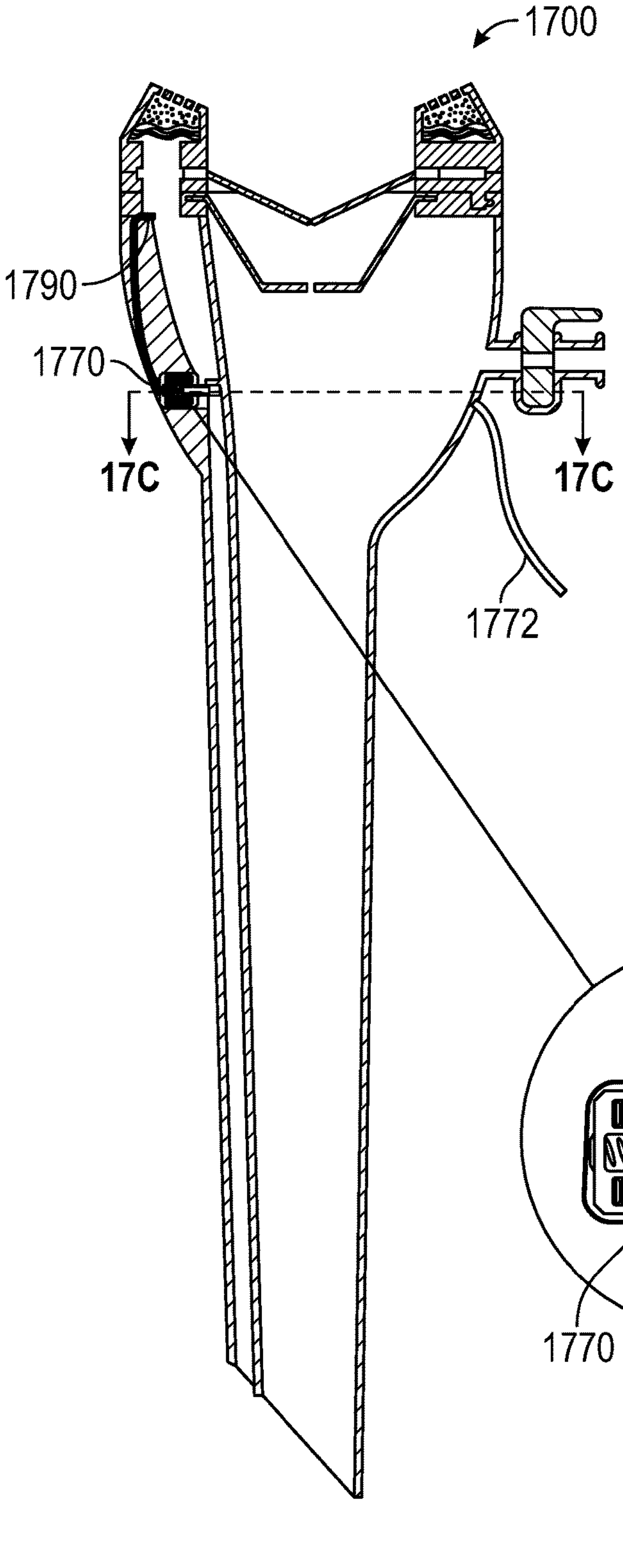
FIGS. 17A-17C illustrate an embodiment of a venting cannula that can include electrical venting features.
Figure 17C:
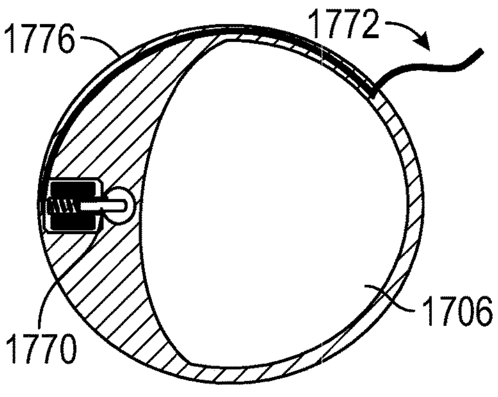
Figure 17B:
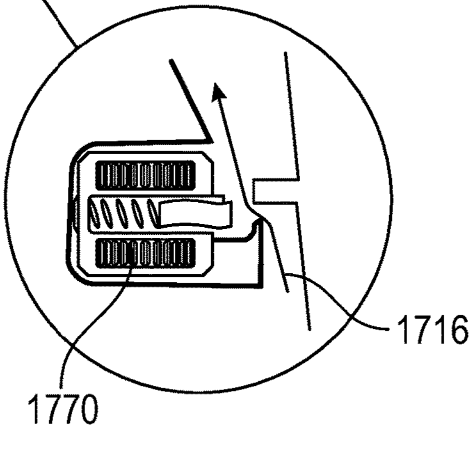

FIGS. 17A-17C illustrate an embodiment of a venting cannula 1700 that can include electrical venting features. As shown in the longitudinal cross-sectional view of FIG. 17A, one or more sensors 1790 can be present in the lumen configured to carry gases from the surgical cavity for filtering and venting (e.g., second lumen 1716). The sensors 1790 can be configured to detect, for example, smoke and other noxious agents, particulates, carbon monoxide, and the like, and/or other gas parameters such as pressure or flow as previously described for example. The sensor 1790 can be molded or otherwise attached in place within the cannula 1700 also as previously described. In some embodiments, the one, two, or more sensors may provide feedback to a controller operably connected to a humidifier or a gases supply (e.g. insufflator). The venting lumen may fluidly couple to a gas evacuation system e.g., a vacuum. The sensor outputs can control the gas evacuation system. Furthermore, the sensor output may control the output valves to control the venting rate in some embodiments. FIG. 17B is a close-up view of FIG. 17A, illustrating valve 1770 relative to the flow path of the second lumen 1716 across the valve.

FIG. 17C is a cross-sectional view through line 17C-17C of FIG. 17A. Shown are valve 1770, which can be solenoid gate valves actuatable via a controller integrated in the cannula or located elsewhere within the surgical insufflation and/or humidification system as previously described. A wire 1772 can extend from the controller for the sensor 1790 and solenoid valves 1770 to control the venting gas flow. The wire 1772 can be overmoulded in some cases in a cannula sidewall at 1776 in order to seal the gas exit pathway as previously described. In some embodiments, the cannula 1700 can also include a socket connection (e.g., delivered by tube set) for supplying power to the heating element via the one or more electrical wires as previously described and illustrated in connection with FIGS. 10A-10B.

Figure 18:
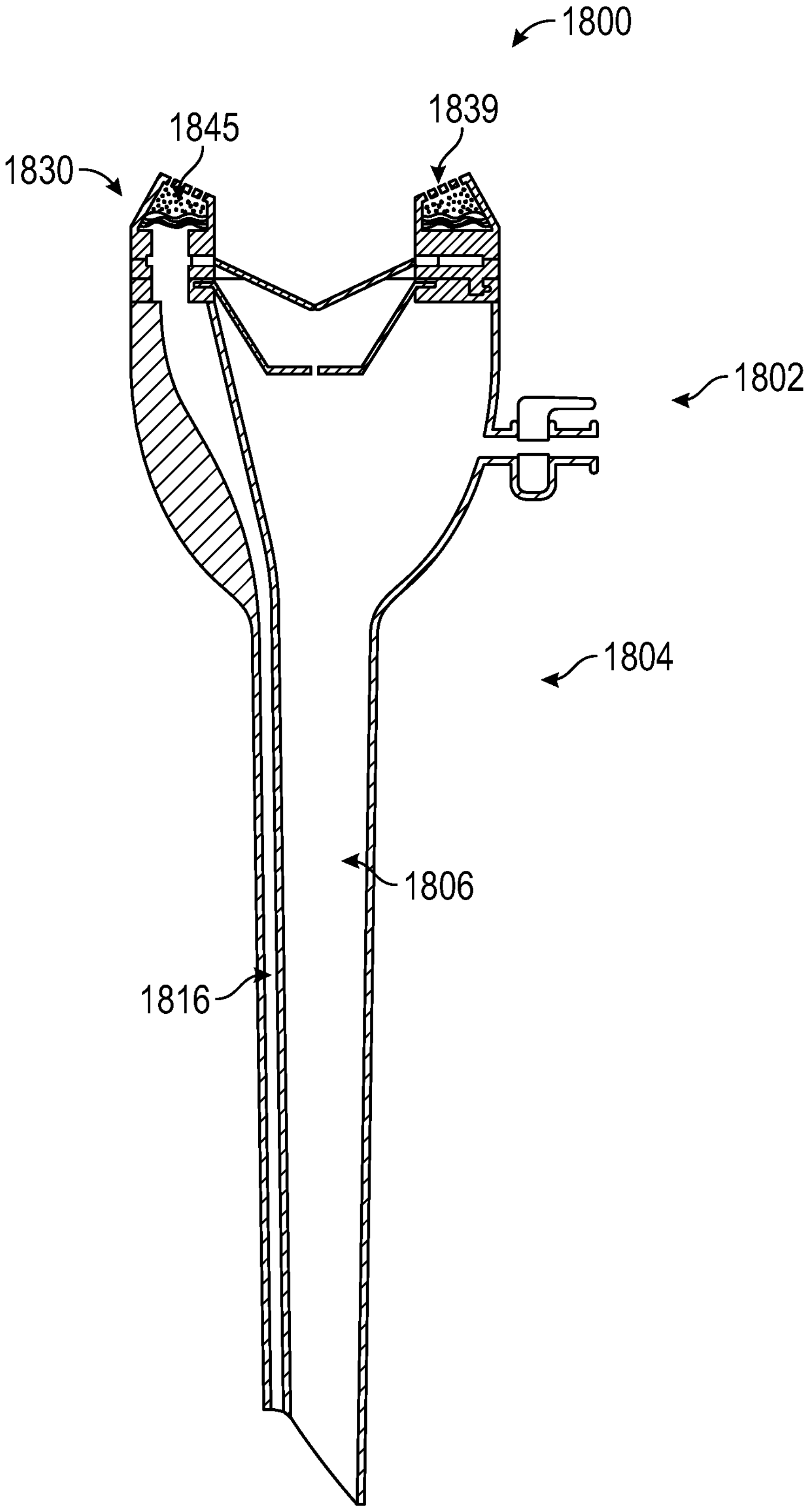
FIG. 18 illustrates a longitudinal sectional view of an embodiment of an offset dual lumen venting cannula.

FIG. 18 illustrates a longitudinal sectional view of an embodiment of an offset dual lumen venting cannula 1800 that can include features as previously described, such as in connection with FIGS. 12A-13 including cannula upper housing 1802, cannula elongate shaft 1804 configured to house a first lumen 1806 and second lumen 1816 therethrough. Also shown are venting element 1830 which can include a heating element 1845 within the gas flow path of the venting element 1130 and distal to the venting apertures 1139. The heating element 1145 could include a printed circuit board (PCB) heater, and can advantageously heat the gases to be vented sufficiently to prevent the gases from condensing and as such clogging the filter. Other aspects of the heating element 1145 can be as described, for example, in connection with FIGS. 11A-11B above.

Figure 19A:
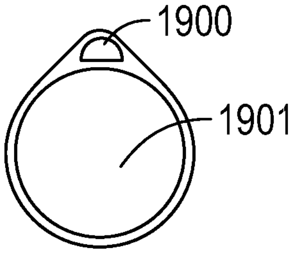
FIGS. 19A-20D illustrate various non-limiting embodiments of offset lumen shapes and/or cannula taper configurations.
Figure 19B:
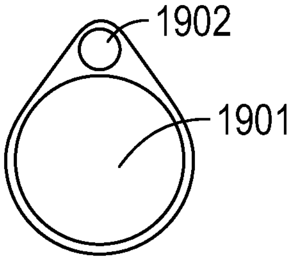
Figure 19C:
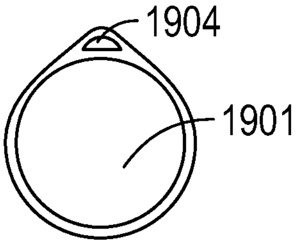
Figure 20A:
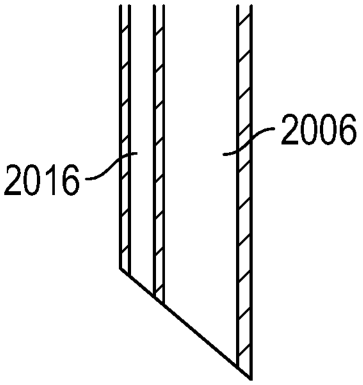
Figure 20B:
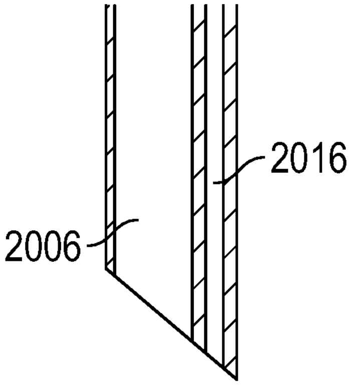
Figure 20C:
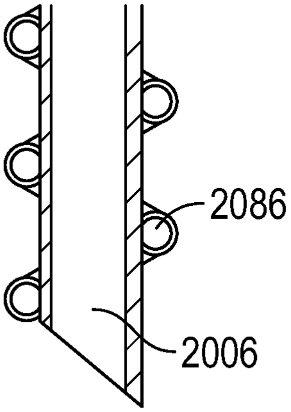
Figure 20D:
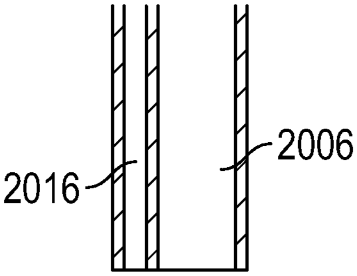

FIGS. 19A-20D illustrate various non-limiting embodiments of offset lumen shapes and/or cannula taper configurations. FIG. 19A illustrates a cross-sectional view of a cannula with an arcuate larger diameter first (main) lumen (e.g. circular main lumen 1901) and a smaller diameter second (offset) lumen 1900 comprising a half-moon/semi-circular cross-sectional shape. FIG. 19B illustrates an embodiment similar to FIG. 19A, except the second lumen 1900 comprises a circular cross-sectional shape. FIG. 19C illustrates another embodiment with the second lumen 1904 comprising a crescent shape. FIG. 20A illustrates the distal end of an elongate shaft of a cannula with first main lumen 2006 and second offset lumen 2016, with a distal taper toward the first main lumen 2006 (e.g., first main lumen 2006 has a longer length than the second offset lumen 2016). FIG. 20B illustrates an embodiment with a taper toward the offset second lumen 2016, in contrast to FIG. 20A. FIG. 20C illustrates an embodiment with a spirally offset second lumen 2086 that forms revolutions around and at least partially circumscribes the larger diameter main first lumen 2006. FIG. 20D illustrates an embodiment with a flat bottom distal end (no taper) between the first lumen 2006 and the second lumen 2016.

Figure 21A:
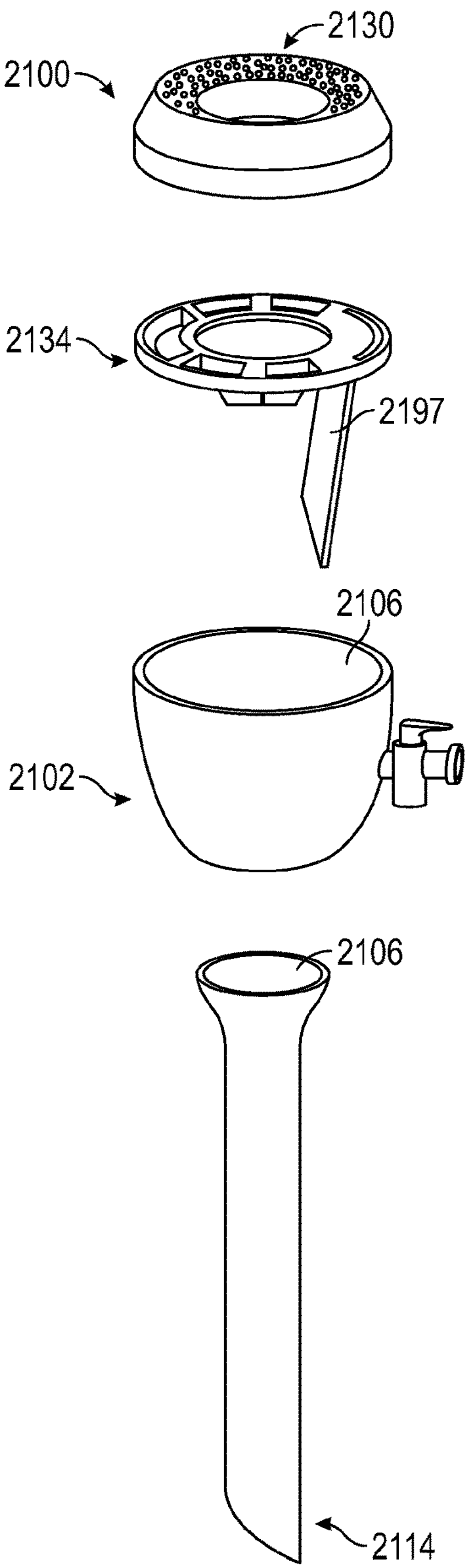
FIGS. 21A-21B illustrate exploded views of another embodiment of a cannula including a venting element including a removable filter and seal.
Figure 21B:
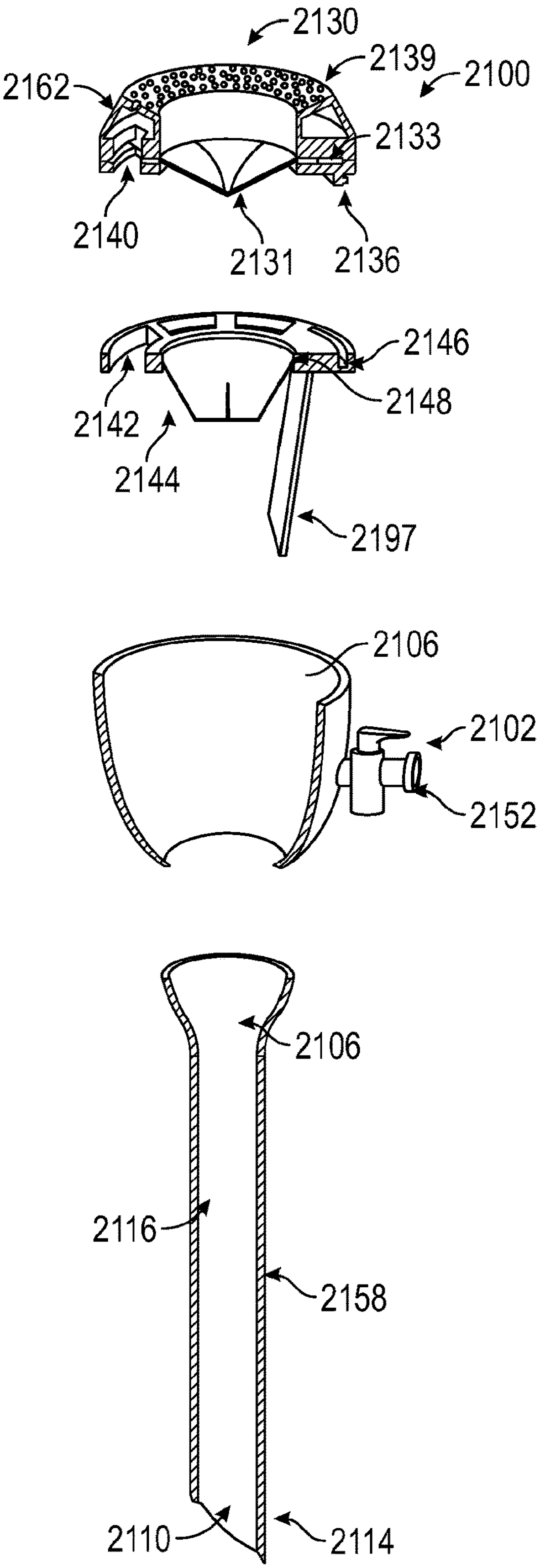

FIGS. 21A-21B illustrate exploded views of another embodiment of a cannula 2100 including a seal housing 2130 including a removable or integrated filter and seal 2131. FIG. 21B illustrates cross-sectional view of the exploded view embodiment of the cannula 2100 of FIG. 21A. Cannula 2100 can incorporate any of the features of cannulas as described elsewhere herein, except the cannula 2100 includes only a single lumen configured to function as both the insufflation gas supply lumen as well as the venting gas lumen. In some embodiments as shown, the sole gas lumen 2106 is configured to receive gases through gas entry port 2152 in the cannula upper housing 2102 and deliver the insufflation gases from a common inlet/outlet 2110 proximate a distal end 2114 of the elongate shaft 2104 and into a surgical cavity. One or more fins 2197 can be operably attached proximally at 2148 to the cannula 2100, such as in the retaining ring 2134 for example, and have an elongate body and a distal free end. A fixed or movable wall or fin 2197 can advantageously be configured to guide insufflation gas entering the cannula 2100 from the gas entry port 2152 in a distal direction down the sole gas lumen 2106, and effectively can divide the sole gas lumen 2106 only partially along its length into a first passage for providing insufflation gases into the surgical cavity, and a second passage for filtering and venting surgical cavity gases outside of the patient. In some embodiments, the first passage and the second passage can be concentric, or offset with respect to each other. The sole lumen 2106 can also be configured to transport gases from the surgical cavity into common inlet/outlet 2110 and vent the gases through the venting apertures 2139 in the seal housing 2130 outside the surgical cavity. The seal 2131 of the venting element 2130 can be overmoulded in hard plastic 2133 or other material as previously described. Also illustrated distal to the seal 2131 can be a retaining ring 2134, which can include venting slots 2142 to allow gas to reach the filter and be vented, and a second seal 2144 for medical instruments. Also illustrated are venting slots 2140, pocket 2162 configured to house gas filters, seal overmoulded component 2133, locking mechanism 2136 (for removable embodiments, not required for integrated seal housing-retaining ring integrated embodiments) for connecting the seal housing 2130 to a complementary locking mechanism 2146 on the retaining ring 2134 with venting slots 2142 that can all be as previously described.

Figure 22:
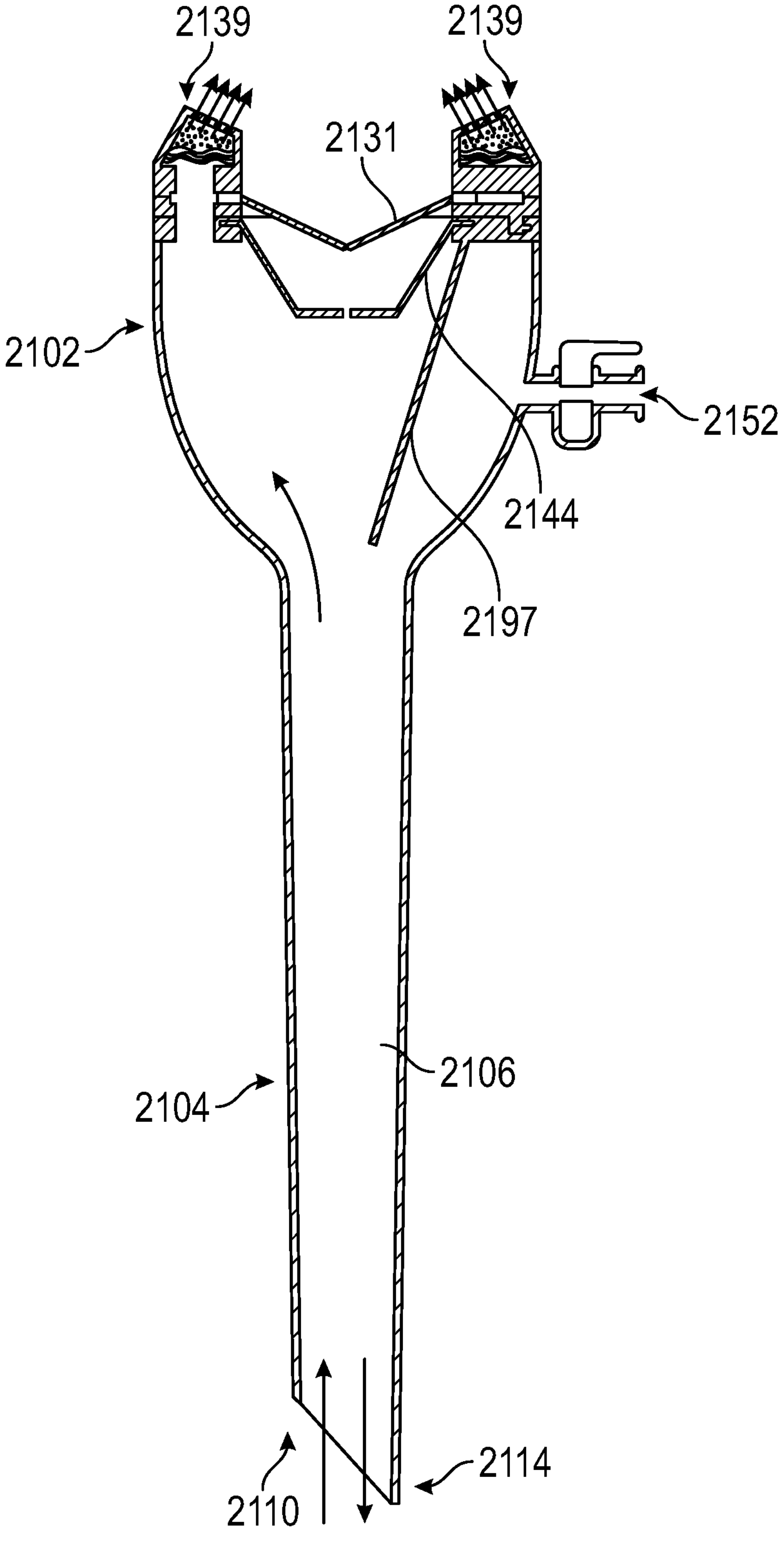
FIG. 22 illustrates a non-exploded longitudinal cross-sectional view of the venting cannula embodiment illustrated in FIGS. 21A and 21B.

FIG. 22 illustrates a non-exploded longitudinal cross-sectional view of the venting cannula 2100 embodiment including a cannula upper housing 2102 and elongate shaft 2103 and single gas lumen 2106 as illustrated in FIGS. 21A and 21B. As shown, insufflation gases can enter the cannula 2100 via gas entry port 2152 and into the single lumen 2106, guided distally by fin 2197, and through the common inlet/outlet 1210 at the distal end 2114 of the elongate shaft 2103 of the cannula 2100 and into the surgical cavity. Gases from the surgical cavity can enter the single gas lumen 2106 of the cannula 2100, flowing proximally through the cannula 2100, through filter in seal housing 2130, and out venting apertures 2139 into the environment. Also shown are seals 2131, 2144 which can be as previously described.

Figure 23A:
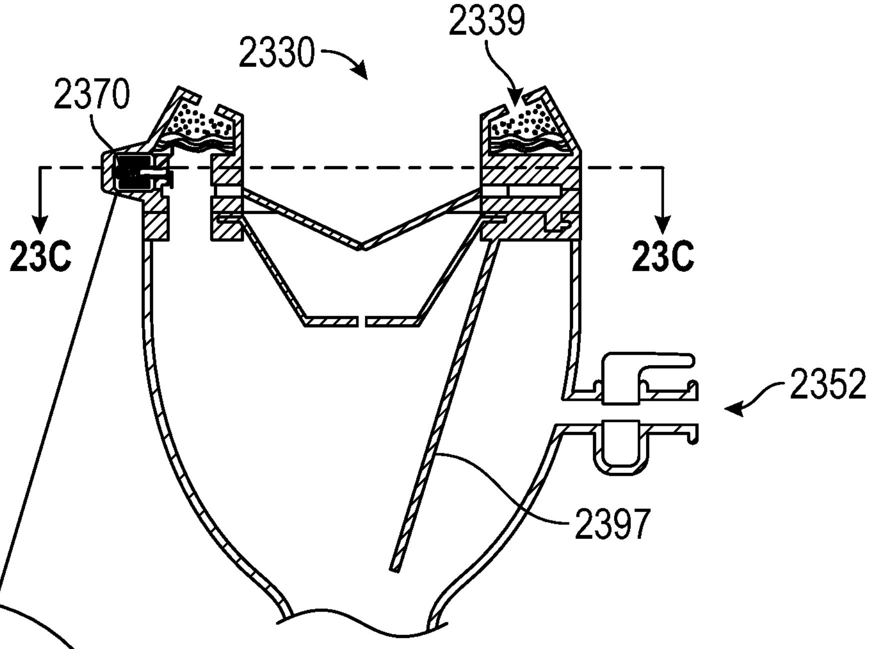
FIG. 23A illustrates the proximal end of a cannula including venting element with venting apertures as previously described.
Figure 23B:
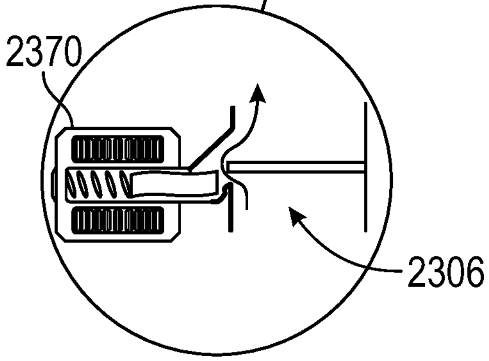
FIG. 23B is a close-up view of FIG. 23A.
Figure 23C:
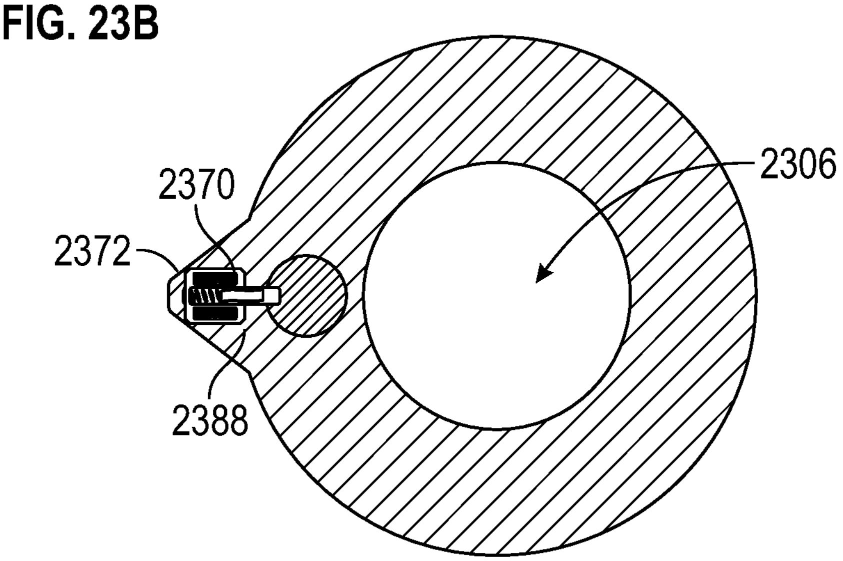
FIG. 23C is a cross-section through line 23C-23C of FIG. 23A.

FIG. 23A illustrates the proximal end of a cannula 2300 including seal housing 2330 with venting apertures 2339 as previously described. Valves 2370 can be present in the flow path of the lumen configured to vent gas from the surgical cavity, e.g., in sole lumen 2306 prior to reaching the seal housing 2330, with venting apertures 2339; gas inlet port 2352, fin 2397, and other features that can be as previously described. FIG. 23B is a close-up view of FIG. 23A, illustrating valve 2370 relative to the flow path of the sole lumen 2306 across the valve. FIG. 23C is a cross-section through line 23C-23C of FIG. 23A, illustrating a valve configuration including one, two, or more solenoid valves 2370, or other types of valves some of which are described elsewhere herein. A single valve 2370 is illustrated moulded in the wall 2372 of the cannula 2300. The wall 2372 of the cannula 2300 can hold the valve 1570 in place. A small venting hole 2388 offset from the longitudinal axis of the cannula and in fluid communication with the sole lumen 2306 when the valve 2370 is open can be controlled by the valve 2370 to selectively allow gases to pass through the filter as described elsewhere herein. In some embodiments, the valve could include diaphragm pressure release valves, solenoid activated relief valves, and/or pressure relief valves as described elsewhere herein.

Figure 24:
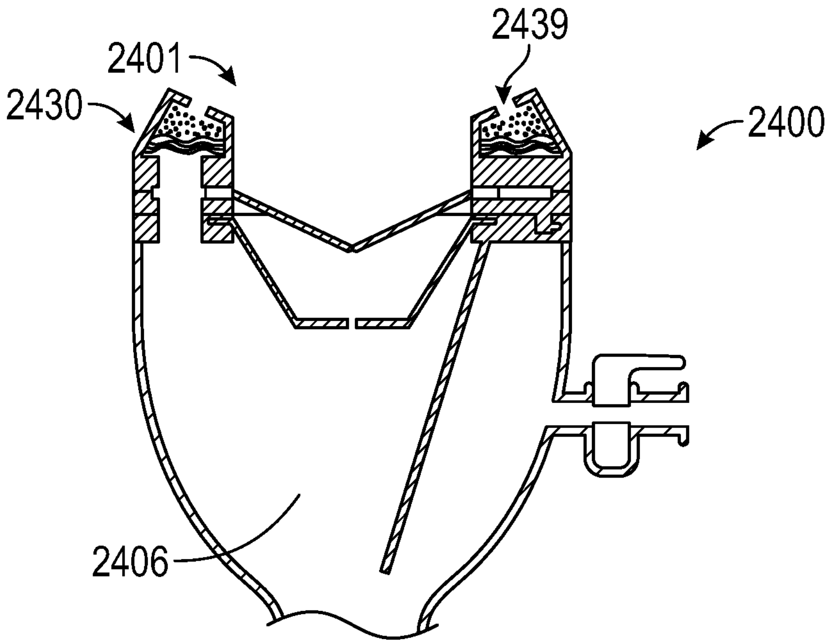
FIG. 24 schematically illustrates additional mechanical/passive venting embodiments that can be included in venting cannulas.

FIG. 24 schematically illustrates additional mechanical/passive venting embodiments that can be included in venting cannulas including those in connection with FIGS. 21A-22, for example, and may or may not include valves. The venting apertures 2439 within venting elements 2430 can be positioned proximal to the filter and at or proximate the proximal end 2401 of the cannula 2400 to receive gases from the surgical cavity via lumen 2406, and could comprise a single restriction orifice, a plurality of small spaced-apart orifices, an umbrella pressure relief valve, or other natural venting options as previously described herein.

Figure 25A:
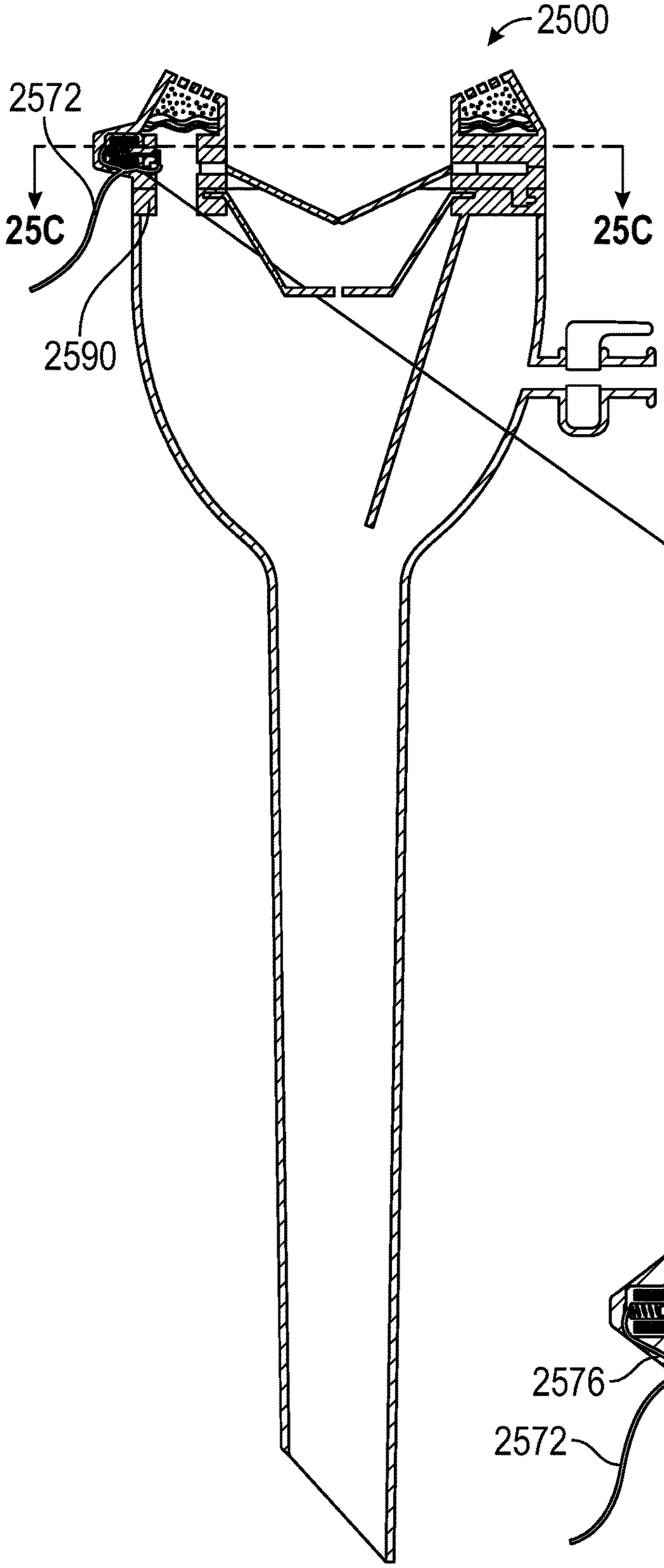
FIGS. 25A-25C illustrate an embodiment of a single lumen venting cannula that can include electrical venting features.
Figure 25B:
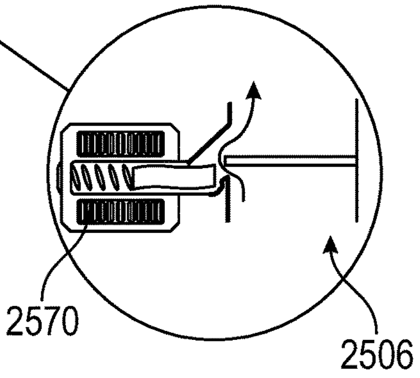
Figure 25C:
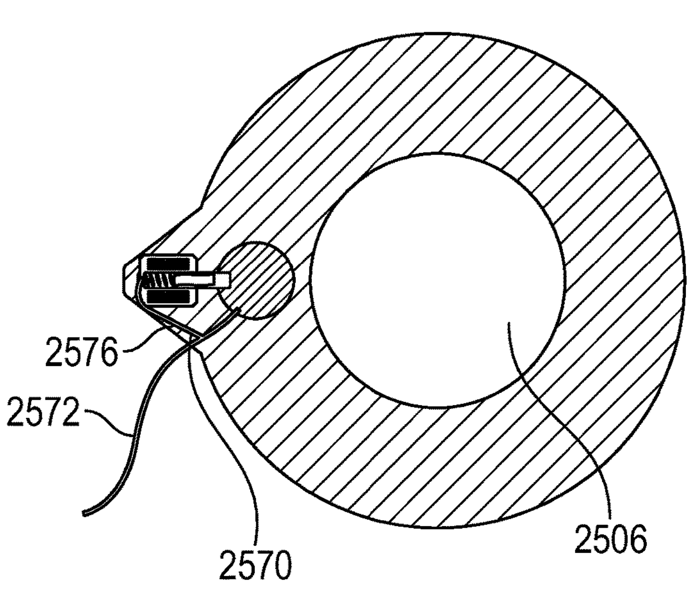

FIGS. 25A-25C illustrate an embodiment of a single lumen venting cannula 2500 that can include features as described, for example, in connection with FIGS. 20A-21, and also include electrical venting features. As shown in the longitudinal cross-sectional view of FIG. 25A, one or more sensors 2590 can be present in the single lumen 2506 configured to carry gases from the surgical cavity for filtering and venting. The sensor 2590 can be configured to detect, for example, smoke and other noxious agents, particulates, carbon monoxide, and the like, and/or other gas parameters such as pressure or flow as previously described for example. The sensor 2590 can be molded or otherwise attached in place within the cannula 2500 also as previously described. FIG. 25B is a close-up view of FIG. 25A, illustrating valve 2570 relative to the flow path of the lumen 2506 across the valve.

FIG. 25C is a cross-sectional view through line 25C-25C of FIG. 25A. Shown are valve 2570, which can be solenoid gate valves actuatable via a controller integrated in the cannula or located elsewhere within the surgical insufflation and/or humidification system as previously described. A wire 2572 can extend from the controller for the sensor 2590 and solenoid valves 2570 to control the venting gas flow. The wire 2572 can be overmoulded in some cases in a cannula sidewall at 2576 in order to seal the gas exit pathway as previously described. In some embodiments, the cannula 2500 can also include a socket connection (e.g., delivered by tube set) for supplying power to the heating element via the one or more electrical wires as previously described and illustrated in connection with FIGS. 10A-10B.

The example cannulas disclosed herein can also include a socket connection (e.g., delivered by tube set) for supplying power to the heating element via the one or more electrical wires as previously described, for example, in connection with FIGS. 10A-10B.

Figure 26A:
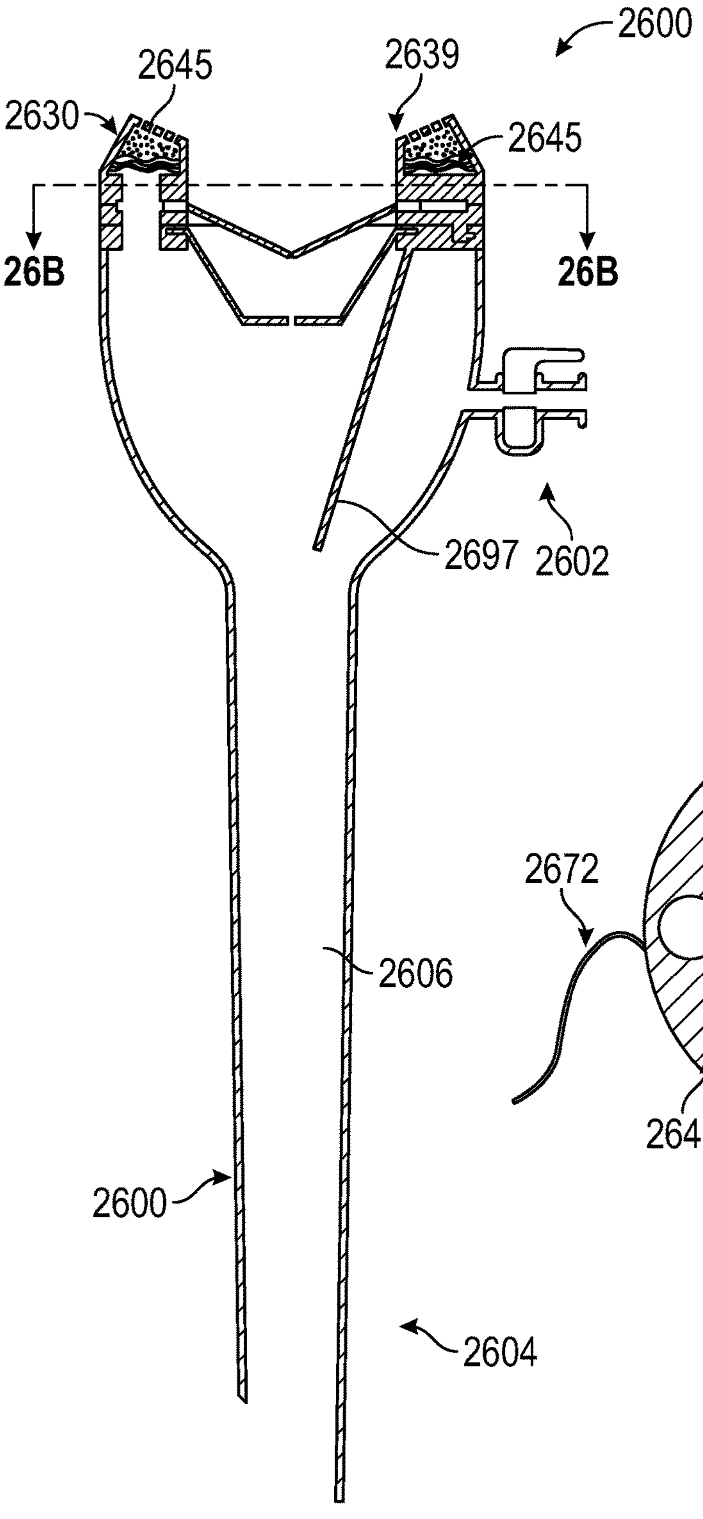
FIGS. 26A-26B illustrate sectional views of an embodiment of a dual lumen venting cannula.
Figure 26B:
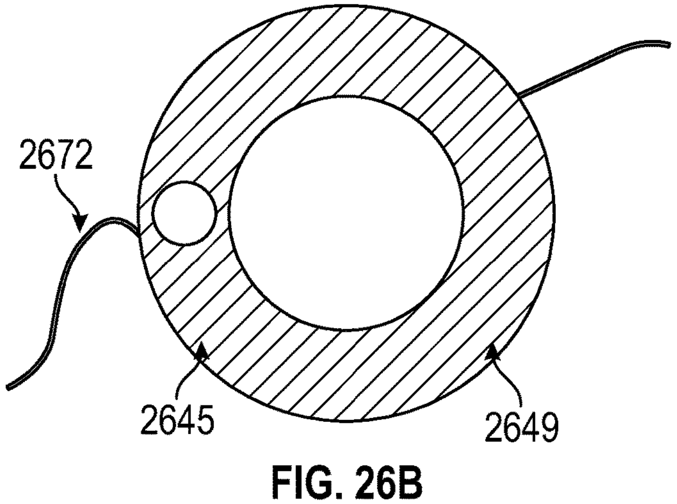

FIGS. 26A-26B illustrate sectional views of an embodiment of a single lumen venting cannula 2600, with fin 2697 creating a partition between a gases inflow path and a gases outflow path, that can include any number of features as previously described, such as in connection with FIGS. 20A-21 including cannula upper housing 2602, cannula elongate shaft 2604 configured to house a single lumen 2606 therethrough. Also shown are seal housing 2630 which can include a heating element 2645 within the gas flow path of the venting element 2630 and distal to the venting apertures 2639. The heating element 2645 could include a printed circuit board (PCB) heater, and can advantageously heat the gases to be vented sufficiently to prevent the gases from condensing and as such clogging the filter. Other aspects of the heating element 2645 can be as described, for example, in connection with FIGS. 11A-11B above. FIG. 26B is a cross-section through line 26B-26B of FIG. 26A. As shown, the power to the PCB heater is provided, for example, by a wire connection 2672 to a power source in a connected surgical humidification system. The PCB heater 2645 can be positioned within the cannula and configured such that the PCB 2649 does not come into direct contact with the gas flow path to avoid any contamination with the PCB itself as previously described.

Figure 27A:
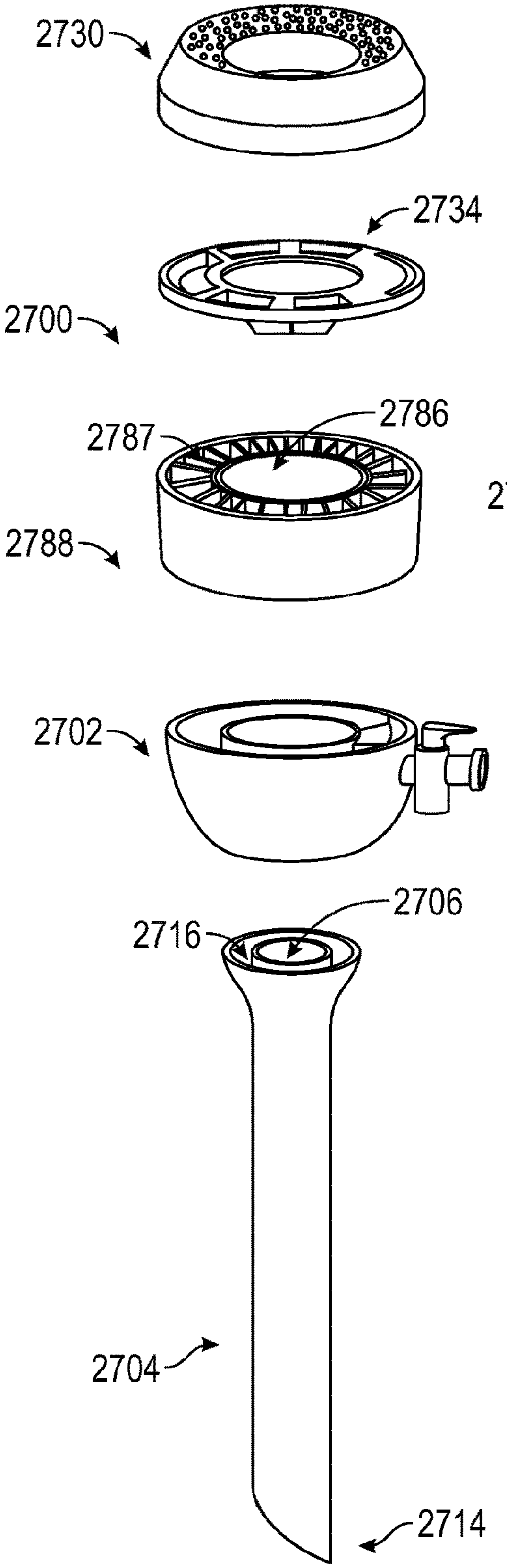
FIGS. 27A-27C are views of another embodiment of a venting cannula including a blower unit.
Figure 27B:
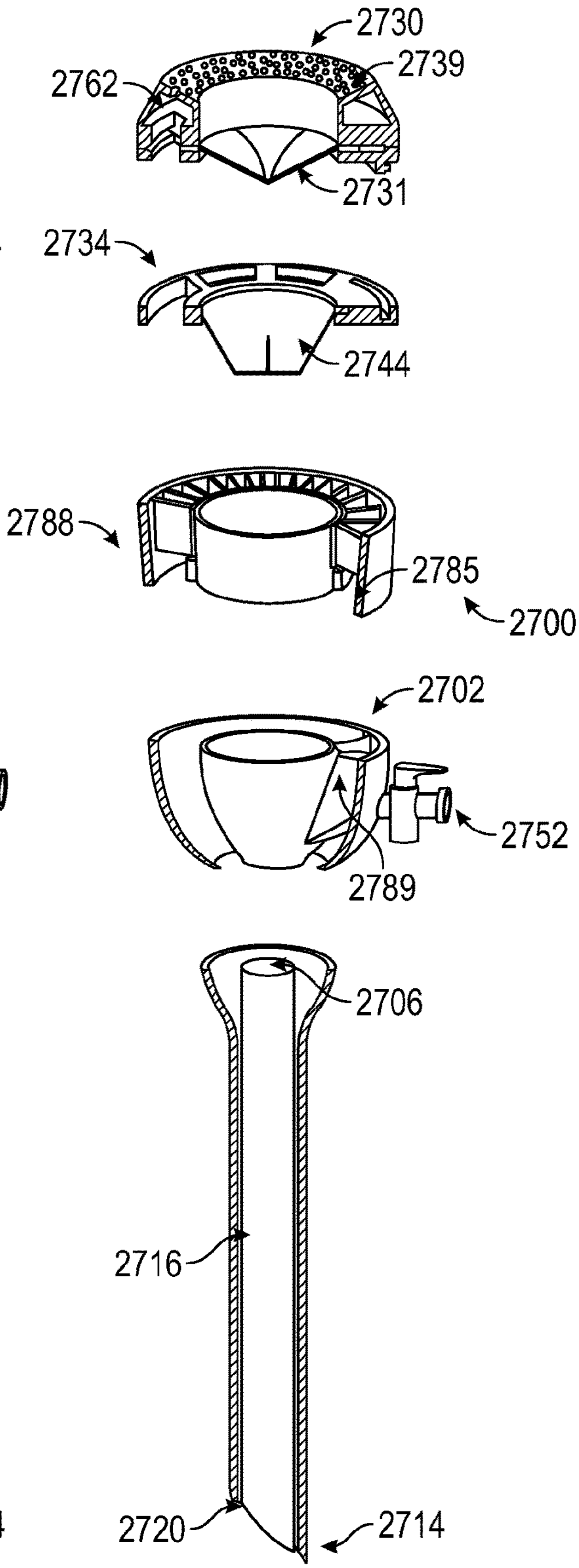

FIGS. 27A-27B are exploded views of another embodiment of a cannula 2700 including a seal housing 2730 including a removable or integrated filter and seal 2731. Multiple filters can be disposed, e.g., in series within the seal housing 2730, such as multiple-stage filters for example as previously described. Also shown in between retaining ring 2734 and cannula upper housing 2702 is blower unit 2788 including one or more blower fans 2787 in fluid communication with outer lumen 2716 and outer lumen inlet 2720 proximate the distal end 2714 of the elongate shaft 2704, the outer lumen 2716 configured to allow inflow of gases, smoke, and other unwanted material from the surgical cavity. The blower unit can include an opening, e.g., central opening 2786 as illustrated in fluid communication with the inner lumen 2706 to allow for normal use of the cannula, e.g., to house a medical instrument therethrough. The blower unit 2788 can be removably or permanently attached to other features of the cannula 2700 (e.g., the retaining ring 2734 and cannula upper housing 2702 as previously described. FIG. 27B illustrates a cross-sectional view of the exploded view embodiment of the cannula 2700 of FIG. 27A, also illustrating venting apertures 2739, pocket 2762 configured to house filters, first seal 2731, second seal 2744 on retaining ring 2734, gas inlet port 2752. Also shown is a blower drive unit, which can be a magnetic circular ring 2785 configured to drive (e.g., rotate) the blower fan 2787 sufficient to suck smoke out of the surgical cavity pneumo. The magnetic circular ring 2785 can be connected to a wired connection (or wirelessly in other embodiments) operably connected to the insufflation line of the gas inlet port 2752.

Figure 27C:
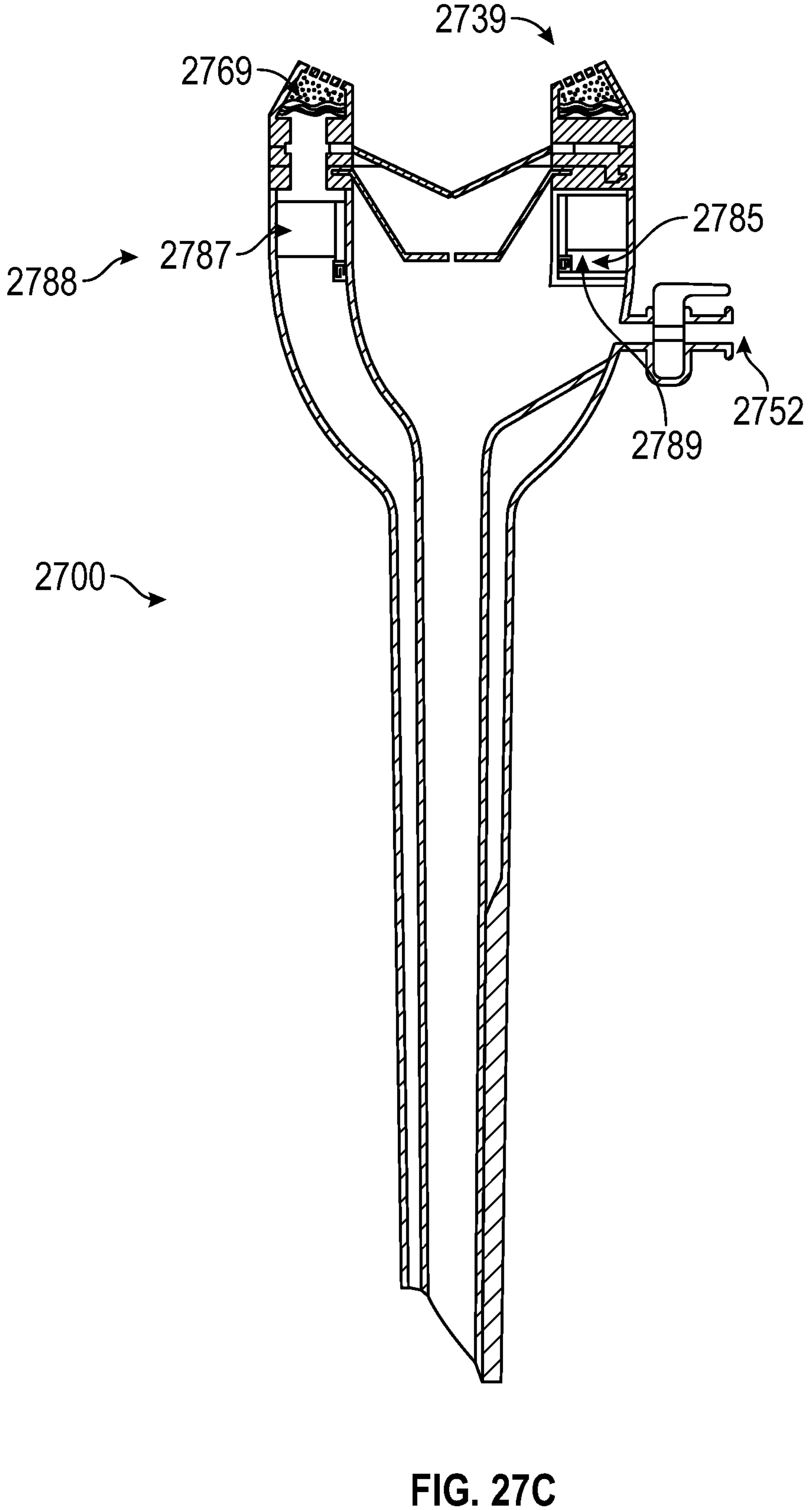

FIG. 27C is a non-exploded longitudinal sectional view of the cannula 2700 including a blower unit 2788 as illustrated in FIGS. 27A-27B, illustrating blower fan blades to provide suction for smoke in the venting lumen, blower drive unit including a magnetic circular ring 2785 configured to drive the blower fan 2787. Also illustrated are venting apertures 2739 and one more removable or integrated filters 2769 for venting smoke that can be as described elsewhere herein.

Figure 28:
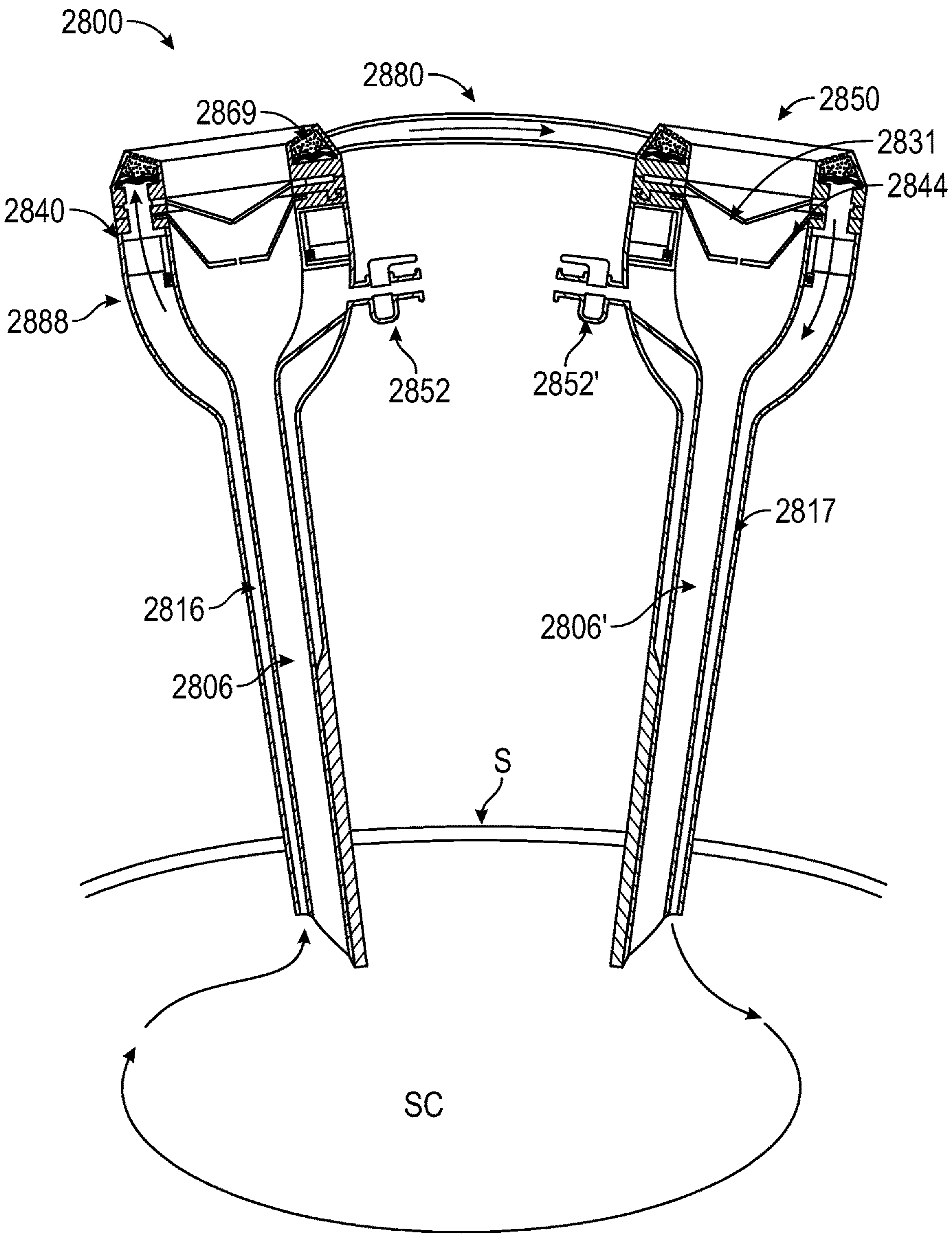
FIG. 28 is a longitudinal sectional view of an embodiment of a multi-cannula system configured to recirculate clean insufflation gases, e.g., carbon dioxide, through a secondary cannula.

FIG. 28 is a longitudinal sectional view of an embodiment of a multi-cannula system 2800 configured to recirculate clean insufflation gases, e.g., carbon dioxide, through a secondary cannula. Illustrated are a first cannula 2840 and a second cannula 2850 fluidly connectable via conduit 2880. Cannulas 2840, 2850 are shown positioned under the skin S and within a surgical cavity SC pneumoperitoneum. Gases, smoke, and other unwanted material from the surgical cavity SC can be suctioned into venting lumen 2816 of the first cannula 2840 by activation of blower unit 2888 as previously described. The gases can circulate in the direction of arrows and be filtered out via one or more filters 2869. The filtered insufflation gases, instead of venting to the outside environment as with certain other embodiments described herein, can instead remain in the closed system and travel via conduit 2880 into lumen 2817 of the second cannula 2850 configured such that recirculated insufflation gases can re-enter the surgical cavity SC. Additional insufflation gases can be added at any time through gas inlet ports 2852, 2852' if needed, and automatically in some embodiments via a controller receiving sensor data as described elsewhere herein. The first cannula 2840 and second cannula 2850 can each have lumens, e.g., inner lumens 2806, 2806' configured to facilitate passages of medical instruments (not shown) therethrough as previously described, and seals 2831, 2844 as previously described that when closed can advantageously maintain the closed nature of the multi-cannula insufflation gas recirculation system.

Figure 29:
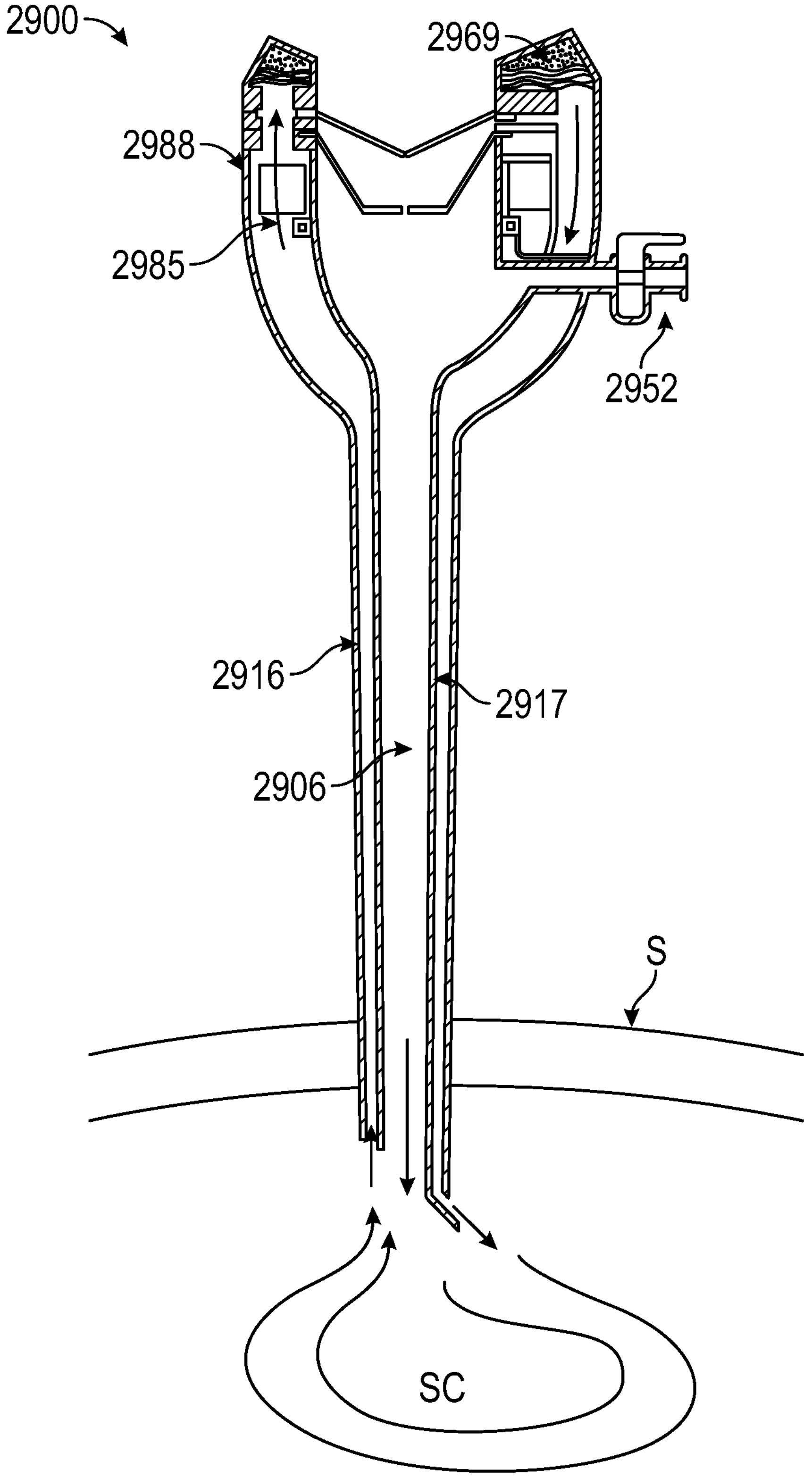
FIG. 29 is a longitudinal sectional view of an embodiment of a cannula system configured to recirculate clean insufflation gases via a single cannula.

FIG. 29 is a longitudinal sectional view of an embodiment of a cannula system 2900 configured to recirculate clean insufflation gases, e.g., carbon dioxide, similar to that of FIG. 28, except using only a single cannula 2900. Cannula 2900 is shown positioned under the skin S and within a surgical cavity SC pneumoperitoneum. Gases, smoke, and other unwanted material from the surgical cavity SC can be suctioned into venting lumen 2916 of cannula 2900 by activation of blower unit 2988 via blower drive unit, e.g., rotating magnetic ring 2985 as previously described. The gases can circulate in the direction of arrows and be filtered out via one or more filters 2969. The filtered insufflation gases, instead of venting to the outside environment as with certain other embodiments described herein, can instead remain in the closed system and travel into lumen 2917 spaced apart from lumen 2916 configured such that recirculated insufflation gases can re-enter the surgical cavity SC. Additional insufflation gases can be added at any time through gas inlet port 2952 if needed, and automatically in some embodiments via a controller receiving sensor data as described elsewhere herein. The cannula can include a lumen 2906, e.g., inner lumen, configured to facilitate passages of medical instruments (not shown) therethrough, and seals as previously described that when closed can advantageously maintain the closed nature of the single cannula insufflation gas recirculation system.

Figure 30A:
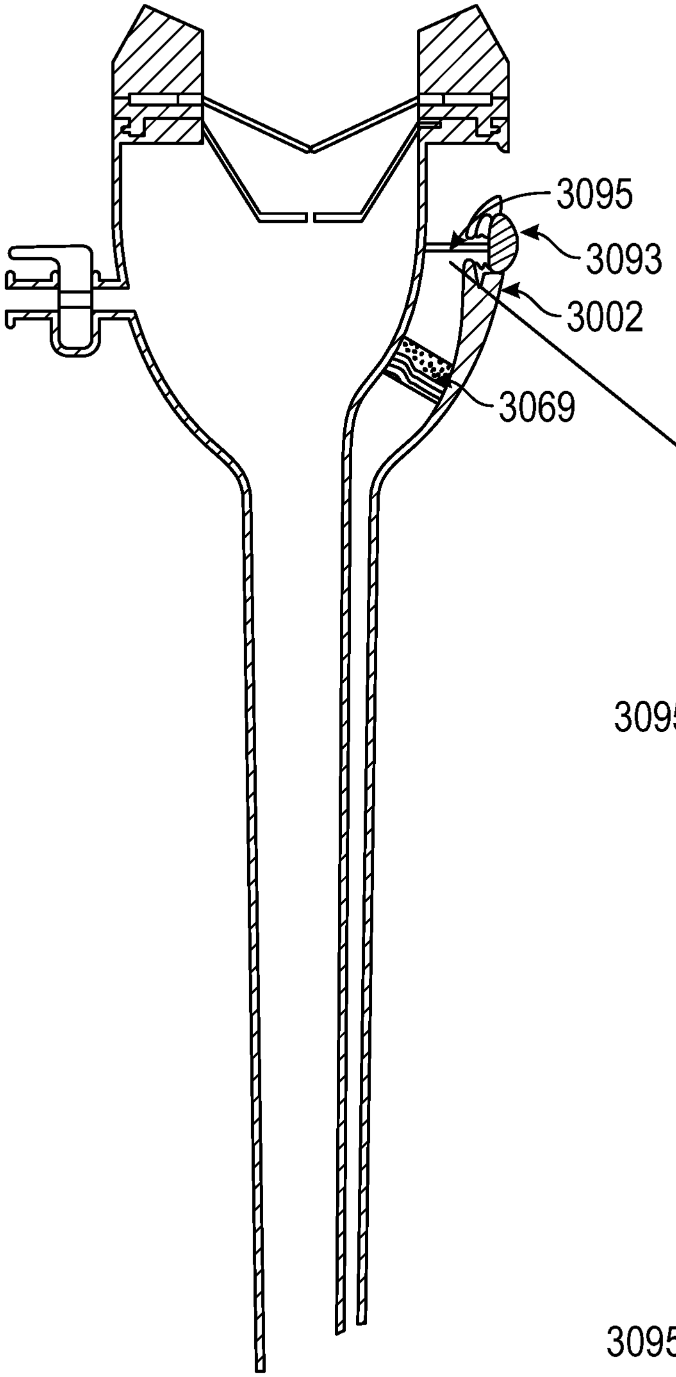
FIGS. 30A-30C illustrate various cross-sectional views of an embodiment of a cannula including a plunger feature configured to remove smoke upon activation of the plunger.
Figure 30B:
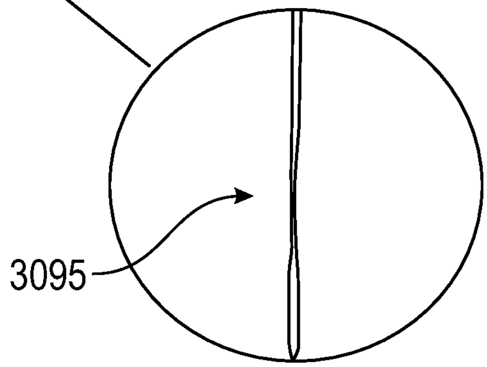
Figure 30C:
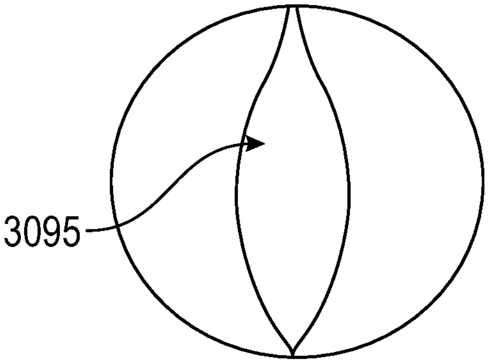
Figure 31A:
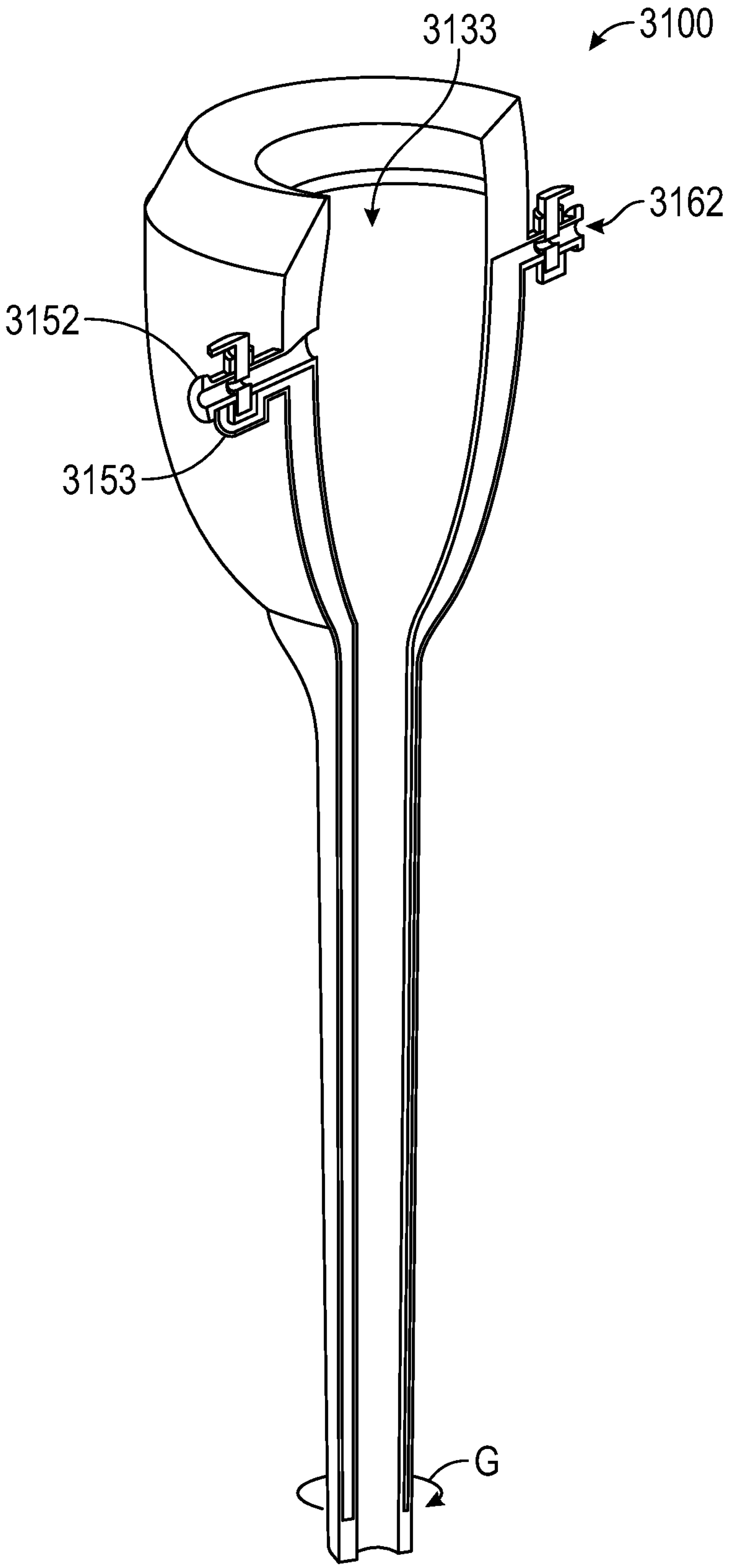
FIG. 31A illustrates a partial cut-away perspective view of a cannula configured for high pressure Venturi venting of gases, smoke, and other unwanted materials from a surgical pneumo cavity.
Figure 31B:
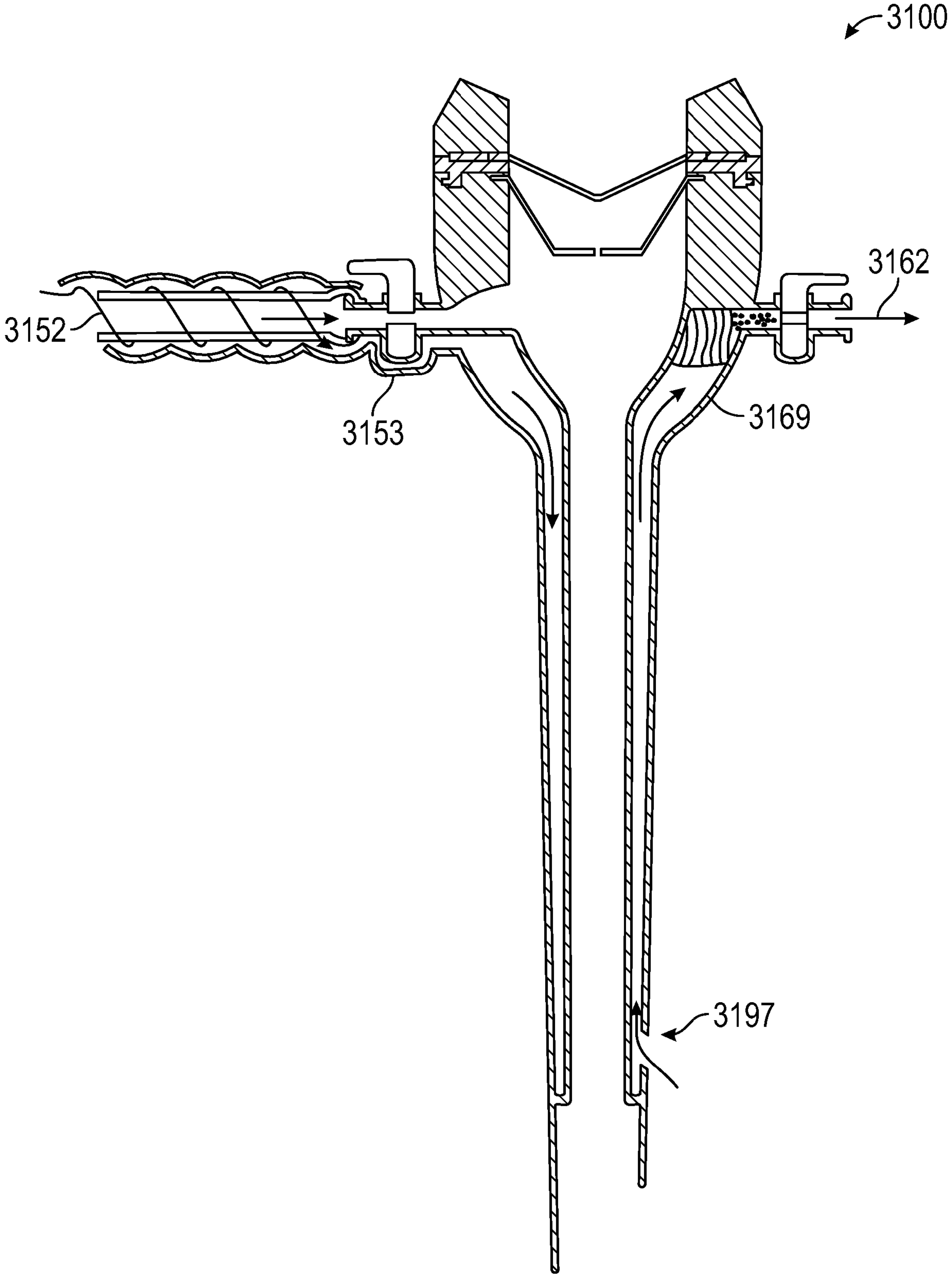
FIG. 31B is a longitudinal sectional view of the cannula of FIG. 31A.

FIGS. 30A-30C illustrate various cross-sectional views of an embodiment of a cannula 3000 including a plunger feature configured to remove smoke upon activation of the plunger. The cannula 3000 can include one or more filters 3069 as previously described, and a control 3093 such as a button on a spring and operably connected to a seal 3095 for example. The control 3093 can be present on the upper cannula housing 3002, or other locations such as on the cannula shaft, retaining ring, or seal housing for example. Actuation of the control 3093 (e.g., depressing the button) can cause the seal 3095 to open, allowing smoke or other gases from the surgical cavity to vent into the outside environment. FIG. 30B illustrates a close-up view of the seal 3095 in a resting closed position. FIG. 30C illustrates the close-view of the seal 3095 of FIG. 30B after actuation of the control, with the seal 3095 in the open position to allow vented gas to leave the cannula 3000. The seal 3095 could be made of silicone, rubber, or other materials as described for example elsewhere herein. FIG. 31A illustrates a partial cut-away perspective view of a cannula 3100 configured for high pressure Venturi venting of gases, smoke, and other unwanted materials from a surgical pneumo cavity, according to some embodiments of the invention. While features of other cannulas as described herein can be incorporated into cannula 3100, several internal cannula components are not shown for simplicity. Illustrated are inlet 3133 configured to fit medical instruments therethrough, insufflation lumen 3152 for delivery of fresh insufflation gases, e.g., carbon dioxide, and additional high pressure insufflation gases line 3153 configured to create a pressure differential to vent smoke out via the exit port of the venting lumen 3162. Gases G can flow around the cannula wall as shown, and then flow into the venting lumen to draw smoke and other surgical cavity gases into the venting lumen. FIG. 31B is a longitudinal sectional view of the cannula 3100 of FIG. 31A, additionally illustrating sidewall inlet opening 3197 in communicating with the venting lumen 3162, as well as one or more filters 3169 in line with the venting lumen 3162 that can be as described elsewhere herein.

Figure 32A:
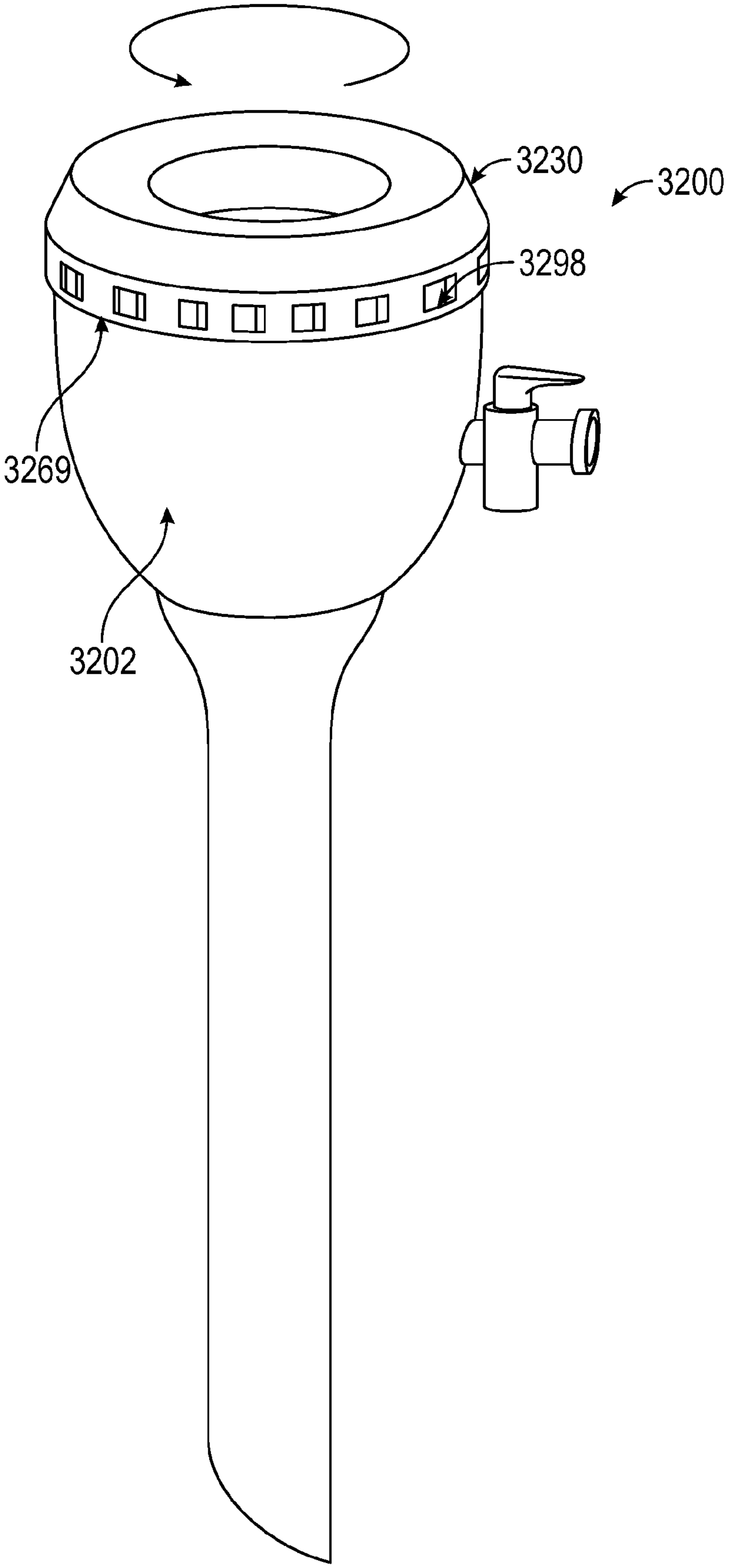
FIGS. 32A-32B illustrate an isometric and cross-sectional view, respectively, of a venting cannula with a venting control feature.
Figure 32B:
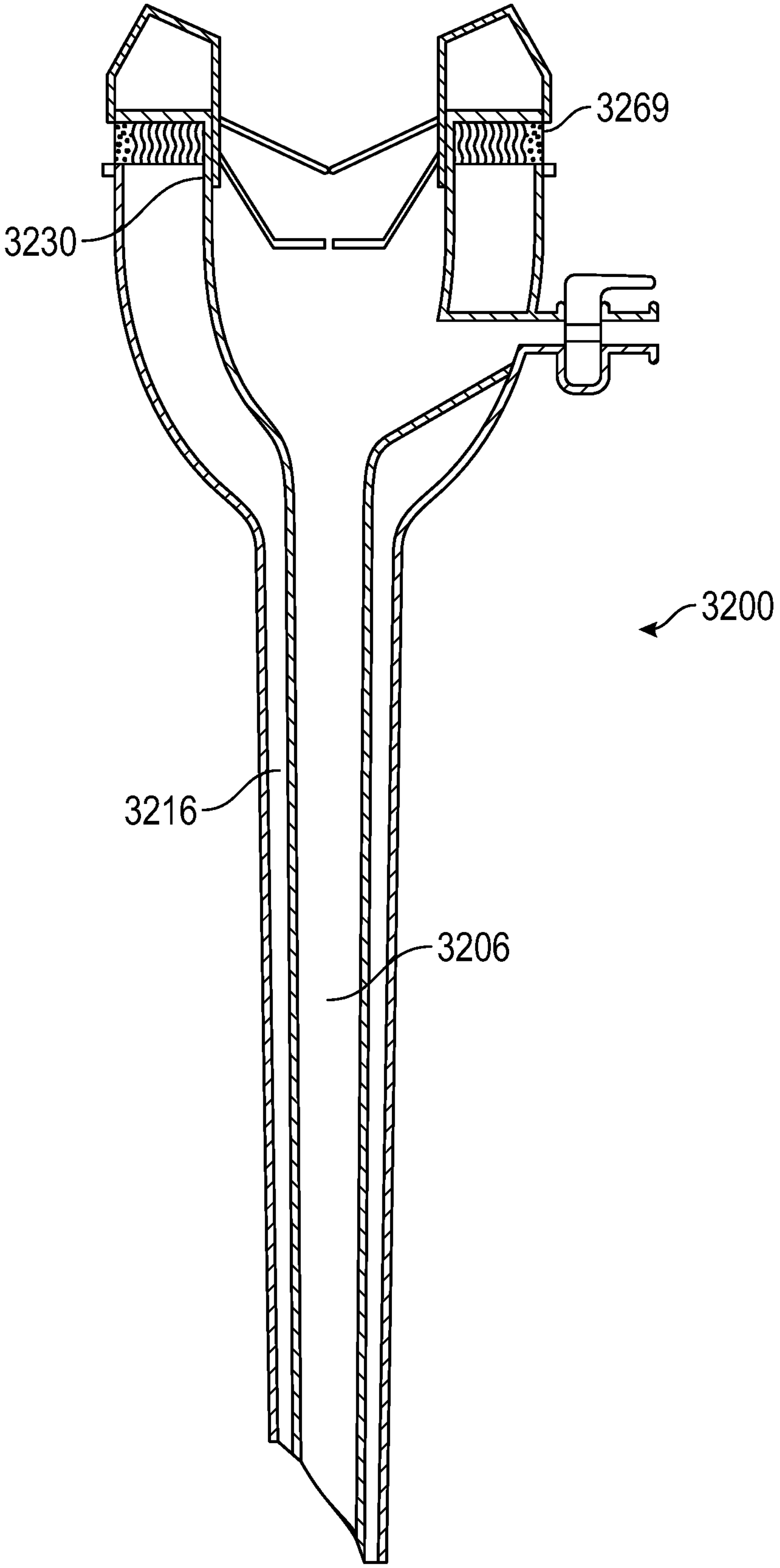

FIGS. 32A-32B illustrate an isometric and cross-sectional view, respectively, of a venting cannula 3200 with a venting control feature, such as a series of small holes or perforations for example, which only allows the gas to pass through while withholding particulate matter. The cannula 3200 can include a rotatable proximal cap 3230 that can be rotated/twisted in an appropriate direction (e.g., utilizing a threaded internal surface in some cases) such as in the direction of the arrow for example, to either open or close the vents by having a series of circumferentially-aligned venting slots 3298 on the cap 3230 to partially or completely line up with, or block venting apertures including one or more filter materials 3269 that can be within the cannula upper housing 3202. FIG. 32A illustrates the vents in a half open position, with the filter material 3269 visible in the half open zone. Manipulating the degree in which the slots 3298 overlap with the vents can control the rate of venting. Also shown in FIG. 32B is venting lumen 3216 in fluid communication with the apertures 3299, and insufflation lumen 3206 that can be as previously described. While the venting cannula 3200 illustrates a double concentric lumen configuration, it will be appreciated that the venting control feature can be used or modified for use with other cannula luminal geometries as disclosed elsewhere herein, for example.

In some embodiments, a filter such as those described and illustrated herein can comprise multiple filter elements. The multiple filter elements can be arranged in fluid communication with the venting passage/venting lumen. The filter elements can be placed within a venting gases path. The filter elements can be arranged in series such that the vented gases/smoke travels through two or more filter elements. Different types of filters can be used in the multi-filter elements. For example, a carbon filter and a UPLA filter can be used to filter out particulate matter and any potentially harmful substances in the vented gases.

In some embodiments, a venting gases cannula such as those described and illustrated herein may include one or more heating elements. The heating elements may be located within one, two, or more lumens. The heating elements may extend a partial length or the entire length of the lumens. The heating elements are configured to heat the gases being delivered to the surgical cavity to maintain the temperature of the cavity at a desired value. Further heating the gases prevents condensation of the insufflation gases and vented gases. Further heating the gases can also reduce fogging on any instruments e.g., scopes. Furthermore, one or more heating elements can be in communication or in contact with one or more filter elements to heat the filter elements. Heating the filter elements prevents clogging and condensation in the filter. Additionally the heating elements may also be structured and configured to heat one or more valves in order to heat the vents or valves. Heating these portions reduces condensation forming in the vents and clogging the vents.

Figure 33A:
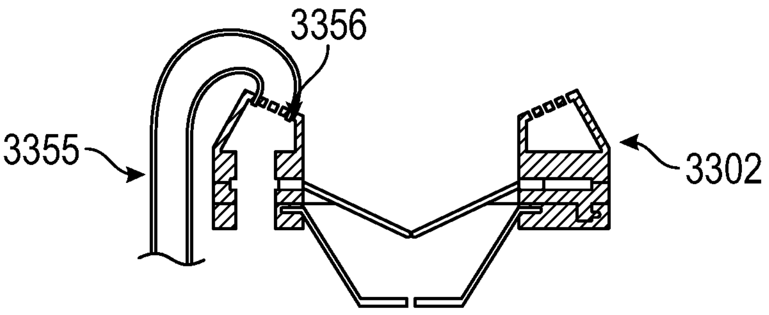
FIGS. 33A-33D illustrate embodiments of filter elements which need not necessarily be integrated in the cannula itself, but rather can be present in a conduit proximal to the proximal end of the cannula upper housing of the cannula.
Figure 33B:
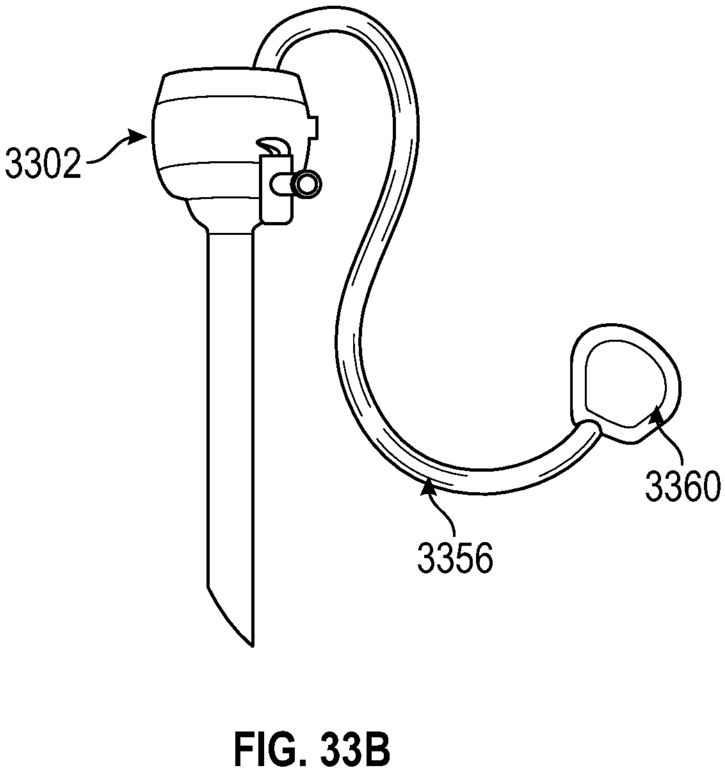
Figure 33C:
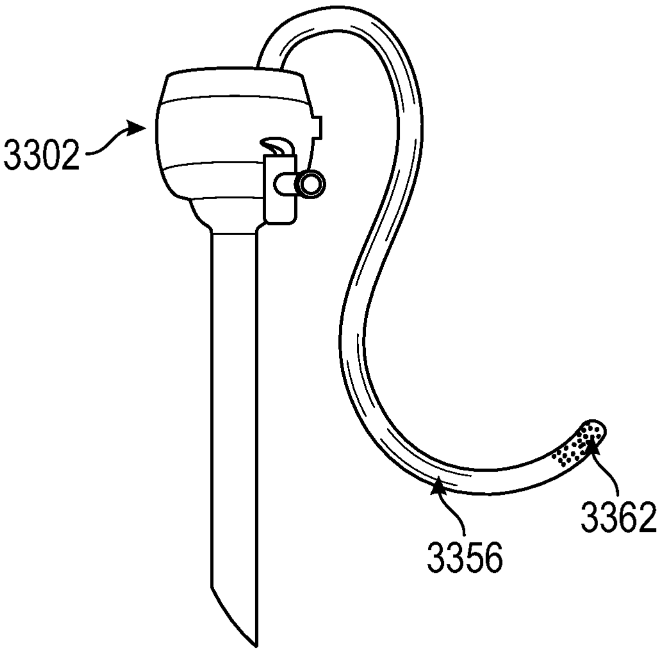
Figure 33D:
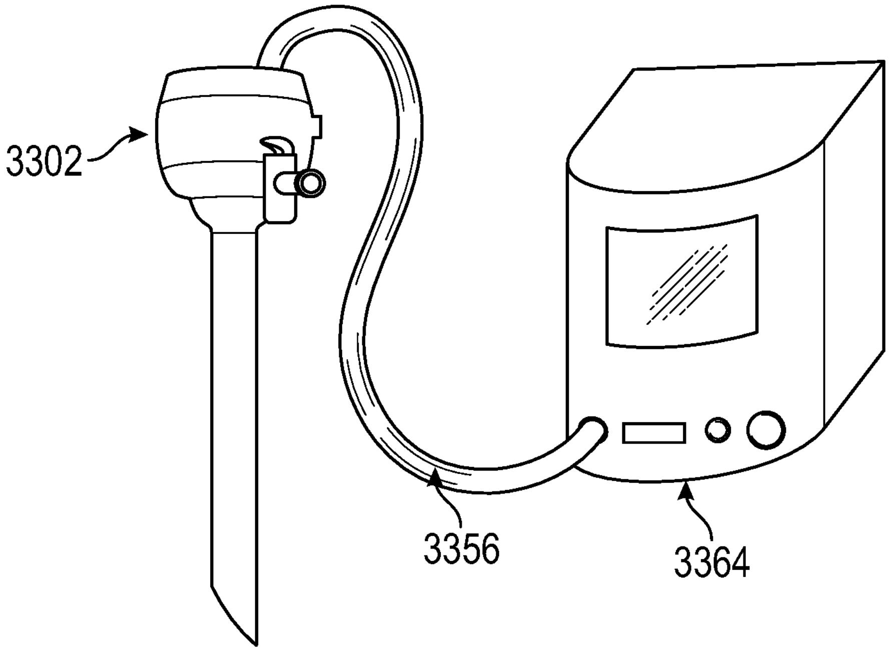

A variety of filter embodiments have been described herein. In some embodiments, the filter elements configured to filter gases, smoke, etc. from the surgical cavity need not necessarily be integrated in the cannula itself, but rather can be present in a conduit proximal to the proximal end of the cannula upper housing 3302 of the cannula. As illustrated schematically in the cross-sectional view of FIG. 33A, a conduit 3355 can be operably attached, such as overmoulded to a proximal portion 3356 of the cannula upper housing 3302 for example. FIG. 33B schematically illustrates an embodiment of a teabag filter 3360 fluidly connected to the proximal end of cannula upper housing 3302 of the cannula via conduit 3356. FIG. 33C schematically illustrates an embodiment of a snake filter 3362 fluidly connected to the proximal end of cannula upper housing 3302 of the cannula via conduit 3356, where the filter 3362 can be present in the terminal end of the conduit 3356 furthest away from the proximal end of the cannula upper housing 3302. FIG. 33D schematically illustrates an embodiment of a box filter 3364 that can include an active filter, electronics, a control, and other features, and fluidly connected to the proximal end of cannula upper housing 3302 of the cannula via conduit 3356, where the filter 3364 can be present in a device or housing connected to the terminal end of the conduit 3356 furthest away from the proximal end of the cannula upper housing 3302.

Figure 34A:
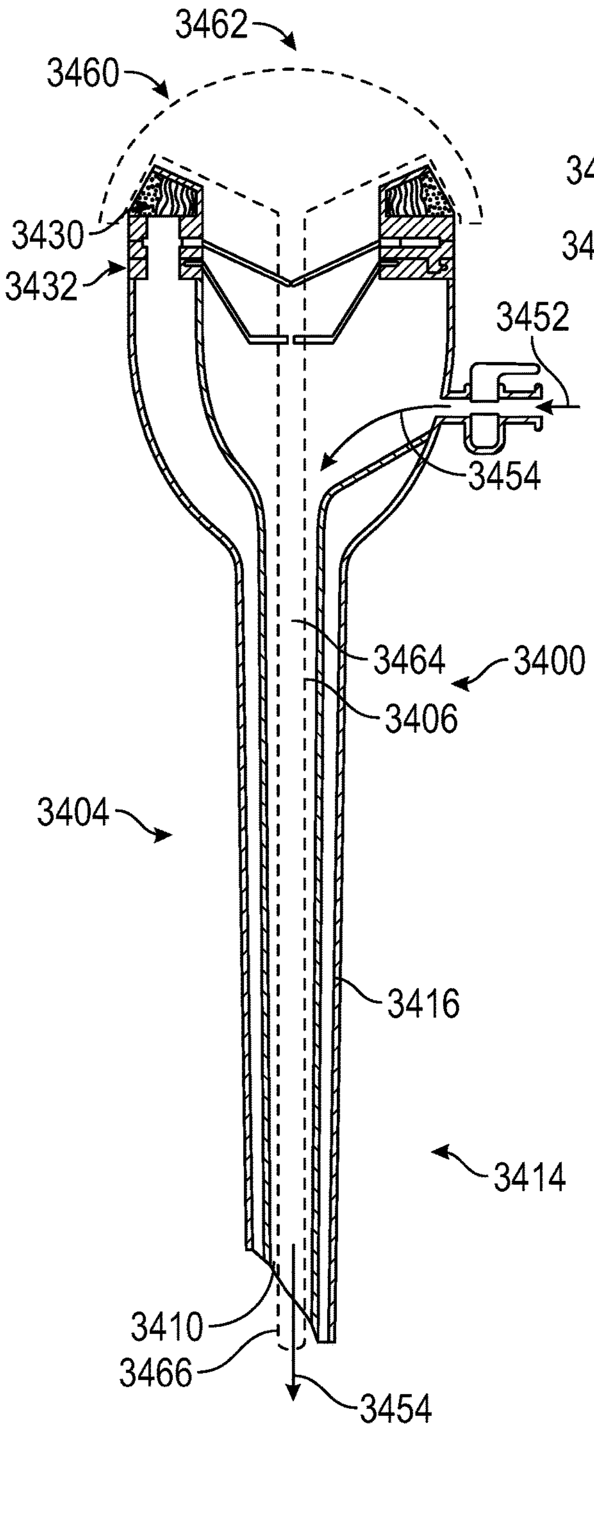
FIG. 34A illustrates a non-exploded cross-sectional view of the venting cannula embodiment and obturator.
Figure 34B:
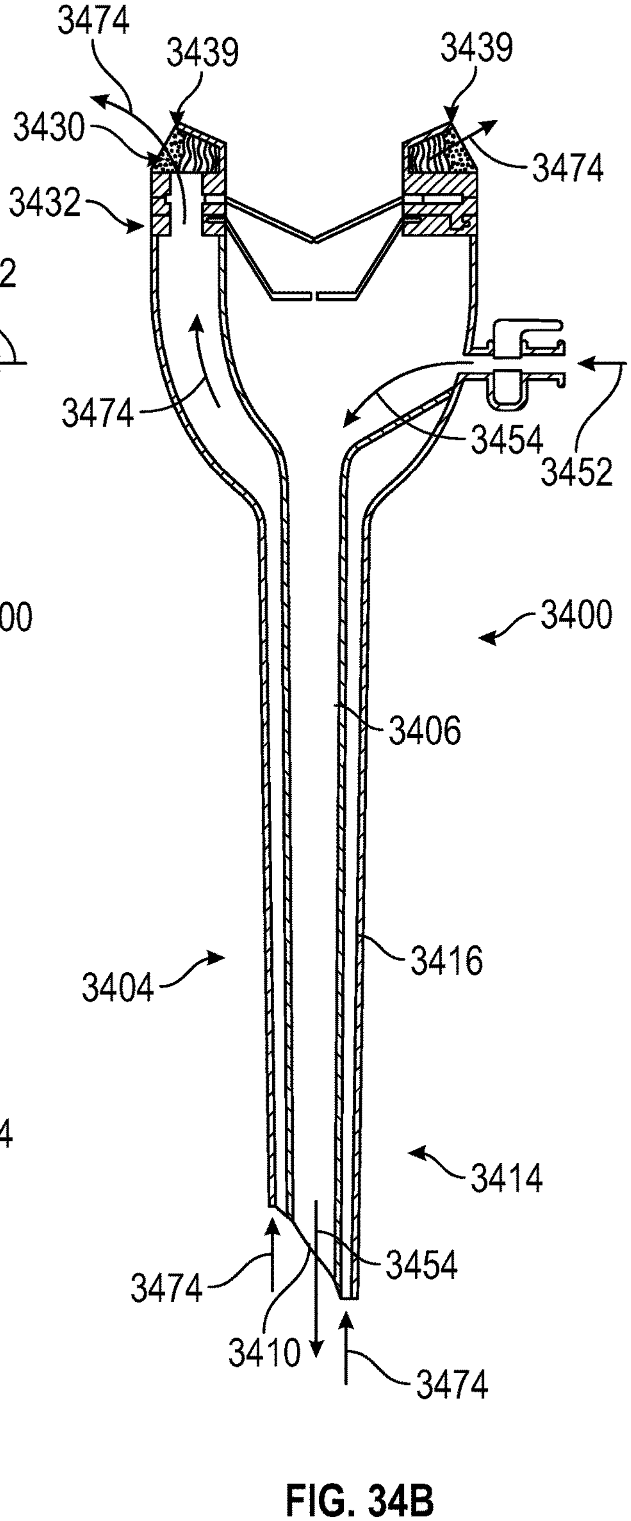
FIG. 34B illustrates a non-exploded cross-sectional view of the venting cannula embodiment of FIG. 34A with the obturator removed.

FIGS. 34A-34B illustrate sectional views of an embodiment of a dual lumen venting cannula 3400 that can include features as previously described, including cannula upper housing 3432, cannula elongate shaft 3404 configured to house a first lumen 3406 and second lumen 3416 therethrough. As shown, insufflation gases can enter the cannula 3400 via gas entry port 3452 and into the first (e.g., central) lumen 3406 in the direction of arrows 3454, and through the outlet 3410 at the distal end 3414 of the elongate shaft 3404 of the cannula 3400 into the surgical cavity. With reference to FIG. 34A, the obturator 3460 can be positioned within the first lumen 3406 of the cannula 3400. The obturator 3460 can be configured to seal the venting regions 3439 of the seal housing 3430. The obturator 3460 can be configured to seal the first (e.g. inner) lumen 3406. The obturator 3460 may include a proximal end or cap portion 3462 that is configured to seal the venting regions 3439 of the seal housing 3430, such as the venting apertures 3439 positioned on the proximal end of the seal housing 3430 for example. The elongate shaft 3464 of the obturator 3460 can be configured to be positioned within the first lumen 3406 of the cannula 3400, such that insufflation gases may pass between the exterior of the obturator shaft 3464 and the interior of the first lumen 3406 of the cannula 3400 and out the distal end 3410 of the cannula 3400. This can be achieved for example when the outer diameter of the obturator shaft 3464 is smaller than the inner diameter of the first lumen 3406. Additionally, the elongate shaft 3464 of the obturator 3460 can include a lumen, positioned, for example, concentrically with the first lumen 3406 of the cannula 3400. The obturator lumen can also be configured to allow insufflation gases into the gas entry port 3452 through the distal end 3466 of the obturator 3460 into the surgical cavity.

With reference to FIG. 34B, when the obturator 3460 is removed (and not shown in FIG. 34B), gases can flow in the direction of arrows 3474, from the surgical cavity, entering the second (e.g., outer) lumen 3416 of the cannula 3400, flowing proximally through the cannula 3400, through filter in seal housing 3430, and out venting apertures 3439 in the seal housing 3430 and into the environment outside of the surgical cavity. Similar to the flow of gas described in FIG. 34A, when the obturator 3460 is removed (and not shown in FIG. 34B), gases can flow in the direction of arrows 3454, such that the first lumen 3406 can be configured to receive insufflation gases delivered from a gas entry port 3452 in the cannula upper housing 3432 and deliver the insufflation gases from an outlet 3410 proximate a distal end 3414 of the elongate shaft 3404 and into a surgical cavity.

Figure 35B:
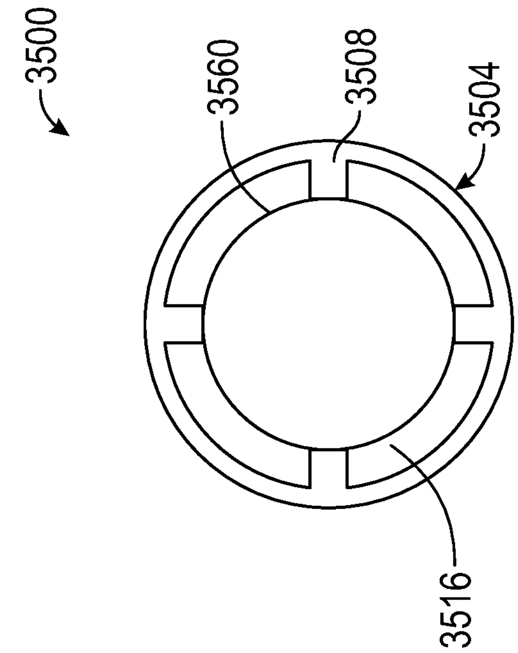
FIGS. 35A-B illustrate a cross-sectional view of a venting cannula configured to receive a surgical instrument to form part of the inner lumen wall of a multiple lumen cannula.
Figure 35A:
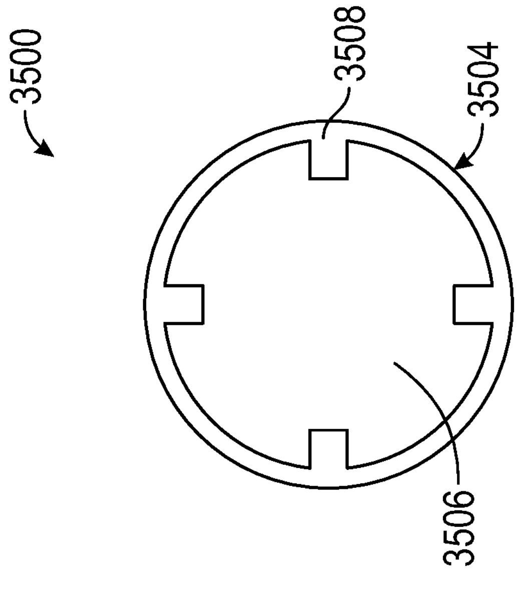

FIGS. 35A-35B illustrate cross-sectional views of an embodiment of a multiple lumen venting cannula 3500. The scope or other medical instrument 3560 is not shown in FIG. 35A, but is shown in FIG. 35B for clarity. The lumens 3516 illustrated in FIG. 35B) are created when a scope or other medical instrument 3560 is positioned within the central lumen 3506 of the elongate shaft 3504 of the cannula 3500, such that one or more walls of the medical instrument 3560 defines at least part of a sidewall of one or more of the lumens 3516. The ribs 3508 are configured to extend inward, for example radially inward, from the inner surface of the elongate shaft 3504 to the outer surface of the medical instrument such as a scope 3560 positioned within the lumen 3506 of the elongate shaft 3504 of the cannula 3500. The lumens 3516 can be formed by ribs 3508 configured to be placed around the medical instrument 3560 to secure the position of the medical instrument 3560. Depending on the number of ribs 3508 present, there may be a plurality of lumens 3516 formed when the medical instrument 3560 is placed in the cannula 3500. The one or more lumens 3516 may be a lumen that vents gas. However, any combination of lumens 3506, 3516 can be used to vent gas or supply insufflation gas. In other embodiments, all lumens 3506, 3516 are used for venting. In some embodiments, the cannula 3500 does not supply any insufflation gas. In some embodiments, about or at least about 1, 2, 3, 4, 5, 6, 7, or 8 or more ribs 3508 can be present. The plurality of ribs 3508 can be configured to be spaced apart from each other and sufficiently thin to ensure that gas venting flow is not disrupted. In some embodiments, the ribs 3508 can have a thickness that is less than about, for example, 25%, 20%, 15%, 10%, 5%, or less of the inner diameter of the respective lumen containing the ribs 3508 or ranges including any two of the foregoing values. In some embodiments, the ribs 3508 are integrally formed with an inner wall of the elongate shaft 3504, or otherwise attached. The ribs 3508 can create a partition between a gases inflow path (the lumen 3506 of the elongate shaft 3504) and a gases outflow path (the outer lumen 3516 to the vents).

FIG. 35B is a cross-section of FIG. 35A with a scope or other medical instrument 3560 positioned in the cannula 3500. As shown, the medical instrument, e.g., scope 3560, can be configured to form part of the inner lumen wall. Rather than a separate inner lumen forming the wall to create the multiple lumen cannula (such as the cannula 300 shown in FIG. 4 for example), the outer lumens 3516 as illustrated can be formed by the inner surface of the elongate shaft 3504, the ribs 3508 and a portion of the outside surface of the medical instrument 3560 (which is inserted into the elongate shaft 3504). The inner lumen 3506 can be formed by the scope 3560 inserted in the elongate shaft 3504 of the cannula 3500.

Terminology

Examples of medical gases delivery systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate the principles and details regarding divisions of modules or systems have been provided for ease of description rather than attempting to delineate separate physical embodiments. The examples and figures are intended to illustrate and not to limit the scope of the inventions described herein. For example, the principles herein may be applied to a surgical humidifier as well as other types of humidification systems, including respiratory humidifiers. However, the humidification systems and methods may also optionally not involve a patient's respiratory system and may not be placed within a portion of the respiratory tract (for example, nose, mouth, trachea, and/or bronchi).

As used herein, the term "processor" refers broadly to any suitable device, logical block, module, circuit, or combination of elements for executing instructions. For example, the controller 8 can include any conventional general purpose single- or multi-chip microprocessor such as a Pentium® processor, a MIPS® processor, a Power PC® processor, AMD® processor, ARM® processor, or an ALPHA® processor for example. In addition, the controller 122 can include any conventional special purpose microprocessor such as a digital signal processor or a microcontroller for example. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein, or can be a pure software in the main processor. For example, logic module can be a software-implemented function block which does not utilize any additional and/or specialized hardware elements. Controller can be implemented as a combination of computing devices, e.g., a combination of a DSP and a microprocessor, a combination of a microcontroller and a microprocessor, a plurality of microprocessors, one or more microprocessors in conjunction with a DSP core, or any other such configuration.

Data storage can refer to electronic circuitry that allows data to be stored and retrieved by a processor. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller. Other types of data storage include bubble memory and core memory. Data storage can be physical hardware configured to store data in a non-transitory medium.

Although certain embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments. As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is otherwise understood with the context as used in general to convey that an item, term, etc. may be either X, Y or Z. Thus, such conjunctive language is not generally intended to imply that certain embodiments require at least one of X, at least one of Y and at least one of Z each to be present. As used herein, the words "about" or "approximately" can mean a value is within ±10%, within ±5%, or within ±1% of the stated value.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A surgical cannula for providing insufflation gases to a surgical cavity and for venting gases from the surgical cavity, the surgical cannula comprising:
- a cannula upper housing comprising:
  - a gas entry port; and
  - an opening for receiving a medical instrument;
- at least one venting slot;
- an elongate shaft extending from the cannula upper housing;
- a first lumen extending through the cannula upper housing and the elongate shaft, the first lumen comprising a first lumen inlet and a first lumen outlet, the first lumen configured to receive the insufflation gases from the gas entry port and deliver the insufflation gases from the first lumen outlet proximate a distal end of the elongate shaft and into the surgical cavity, wherein the first lumen inlet is in fluid communication with a source of the insufflation gases through the gas entry port, and wherein the first lumen is configured to receive the medical instrument therethrough; and
- a second lumen extending through the cannula upper housing and the elongate shaft, the second lumen comprising a second lumen inlet and a second lumen outlet, the second lumen outlet in fluid communication with the at least one venting slot, the second lumen configured to receive the gases through the second lumen inlet from the surgical cavity and vent the gases through the at least one venting slot and through a proximal-facing surface to outside the surgical cavity,
- wherein the first lumen is radially offset with respect to the second lumen,
- wherein the first lumen and the second lumen are non-concentric with respect to each other,
- wherein the first lumen is fluidly isolated from the second lumen such that gases can flow through the first lumen and the second lumen simultaneously,
- wherein the first lumen has a larger cross-sectional area than the second lumen, measured across the elongate shaft transverse to a longitudinal axis of the first lumen, and
- wherein the longitudinal axis of the first lumen intersects with the opening in the cannula upper housing.

2. The surgical cannula of claim 1, wherein the surgical cannula is configured to provide passive venting created by a pressure differential with respect to the surgical cavity.

3. The surgical cannula of claim 1, wherein one of the first lumen or the second lumen comprise one or more positioning ribs configured to locate and/or retain an other of the first lumen or the second lumen.

4. The surgical cannula of claim 1, wherein the second lumen comprises one of a semi-circular profile, a crescent profile, or an arcuate profile, and the first lumen comprises a circular profile, wherein the second lumen comprises a helical shape at least partially circumscribing the first lumen.

5. The surgical cannula of claim 1, further comprising a filter in fluid communication with the second lumen.

6. The surgical cannula of claim 5, wherein the filter is positioned within the elongate shaft.

7. The surgical cannula of claim 5, wherein the filter is positioned within the cannula upper housing.

8. The surgical cannula of claim 5, wherein the filter is operably connected to a conduit connected to a proximal end of the cannula upper housing.

9. The surgical cannula of claim 1, wherein the second lumen outlet is angled with respect to a longitudinal axis of the cannula upper housing.

10. The surgical cannula of claim 1, further comprising a first filter and a second filter in fluid communication with the second lumen, the second filter spaced distally apart from the first filter.

11. The surgical cannula of claim 10, wherein the first filter is positioned within the cannula upper housing, and at least one of:

the second filter is positioned distal to the first filter, or the second filter is positioned distal to the first filter and within the cannula upper housing.

12. The surgical cannula of claim 1, further comprising:

a seal housing removably coupled to the cannula upper housing, the seal housing comprising:

an instrument opening configured to receive the medical instrument, the instrument opening aligned with the opening in the cannula upper housing; and a seal positioned within the instrument opening.

13. The surgical cannula of claim 12, wherein the seal housing further comprises a plurality of venting apertures disposed around the instrument opening proximate to the at least one venting slot, the plurality of venting apertures in fluid communication with the at least one venting slot.

14. The surgical cannula of claim 13, further comprising a filter positioned between the at least one venting slot and the plurality of venting apertures.

15. The surgical cannula of claim 12, wherein the cannula upper housing further comprises a retaining ring configured to be removable from a main body of the cannula upper housing, the retaining ring disposed between the seal housing and the main body of the cannula upper housing.

16. The surgical cannula of claim 15, wherein the retaining ring includes the at least one venting slot, and wherein the at least one venting slot is aligned with the second lumen outlet.

17. The surgical cannula of claim 1, wherein the first lumen is separated from the second lumen in the cannula upper housing by an internal wall of the cannula upper housing.

18. The surgical cannula of claim 1, wherein the first lumen outlet is positioned distal to the second lumen inlet along the elongate shaft.

19. The surgical cannula of claim 1, wherein the cross-sectional area of the first lumen is at least 50% larger than a cross-sectional area of the second lumen, measured across the elongate shaft transverse to the longitudinal axis of the first lumen.

20. The surgical cannula of claim 1, wherein at least a portion of the second lumen is offset and not aligned with the opening in the cannula upper housing.

* * * * *